US006887890B2

(12) United States Patent
Fujiwara et al.

(10) Patent No.: US 6,887,890 B2
(45) Date of Patent: May 3, 2005

(54) COMPOUNDS EXHIBITING THROMBOPOIETIN-LIKE ACTIVITIES

(75) Inventors: Shinya Fujiwara, Gotenba (JP); Tomokazu Ozaki, Gotenba (JP); Toshiro Kozono, Gotenba (JP); Kunihiro Hattori, Gotenba (JP); Toru Esaki, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/296,638

(22) PCT Filed: May 30, 2001

(86) PCT No.: PCT/JP01/04561

§ 371 (c)(1),
(2), (4) Date: Nov. 27, 2002

(87) PCT Pub. No.: WO01/92211

PCT Pub. Date: Dec. 6, 2001

(65) Prior Publication Data

US 2003/0162724 A1 Aug. 28, 2003

(30) Foreign Application Priority Data

May 30, 2000 (JP) .................................. 2000-161036

(51) Int. Cl.$^7$ ...................... C07C 237/22; C07D 401/14
(52) U.S. Cl. ...................... 514/332; 514/415; 514/616; 546/255; 548/454; 564/155
(58) Field of Search ................. 514/332, 415, 514/616; 546/255; 548/454; 564/155

(56) References Cited

U.S. PATENT DOCUMENTS 4,695,405 A  9/1987  Harnisch et al. ............ 252/600

FOREIGN PATENT DOCUMENTS

| JP | 01261650 A | * 10/1989 | ......... C07C/237/22 |
|---|---|---|---|
| JP | 10-212289 | 8/1998 | |
| JP | 11-001477 | 1/1999 | |
| JP | 11-152276 | 6/1999 | |
| WO | WO 96/40750 | 12/1996 | |
| WO | WO 00/28987 | 5/2000 | |
| WO | WO 00/35446 | 6/2000 | |
| WO | WO 00/66112 | 11/2000 | |
| WO | WO 01/07423 A1 | 2/2001 | |
| WO | WO 01/17349 A1 | 3/2001 | |
| WO | WO 01/21180 A1 | 3/2001 | |
| WO | WO 01/34585 A1 | 5/2001 | |

OTHER PUBLICATIONS

T.D. Bartley, et al.; "Identification and Cloning of a Megakaryocyte Growth and Development Factor That Is a Ligand for the Cytokine Receptor Mpl"; CELL; vol. 77; pp. 1117–1124; Jul. 1, 1994.

Frederic J. de Sauvage, et al.; "Stimulation of megakaryocytopoiesis and thrombopoiesis by the c–Mpl ligand"; NATURE; vol. 369; pp. 533–538; Jun. 16, 1994.

Steven E. Cwirla, et al.; "Peptide Agonist of the Thrombopoietin Receptor as Potent as the Natural Cytokine"; SCIENCE; vol. 276; pp. 1696–1699; Jun. 13, 1997.

Tatsuya Kimura, et al.; "A non–peptide compound which can mimic the effect of thrombopoietin via c–Mpl"; FEBS Letters 428; pp. 250–254; Apr. 21, 1998.

A. Kraft and F. Osterod, "Self–association of branched and dendritic aromatic amides"; J. Chem. Soc. Perkin Trans. 1; (1998); No. 6; pp. 1019–1025.

* cited by examiner

Primary Examiner—Zinna Northington Davis
(74) Attorney, Agent, or Firm—Morgan, Lewis & Bockius LLP

(57) ABSTRACT

The compounds of the invention are compounds represented by the following general formula (1):

$$E - \left[ \underset{\underset{R^2}{|}}{\underset{|}{\bigcirc}} - N - W^1 - A - (X^1)_p - R^1 \right]_3 \quad (1)$$

wherein E represents one selected from the group consisting of a methylidyne group and a nitrilo group, $R^1$ represents one selected from the group consisting of optionally substituted aryl groups and optionally substituted heteroaryl groups, $R^2$ represents one selected from the group consisting of a hydrogen atom and alkyl groups, $W^1$ represents an amino acid residue, A represents one selected from the group consisting of a carbonyl group and a sulfonyl group, $X^1$ represents one selected from the group consisting of optionally substituted alkylene groups and optionally substituted alkenylene groups, and p represents 0 or 1;
and their pharmacologically acceptable salts, which exhibit thrombopoietin-like activity.

11 Claims, 7 Drawing Sheets

Scheme C

Step C1

Step C2    Step C3

Step C4

Step C5

Scheme E

COMPOUNDS EXHIBITING THROMBOPOIETIN-LIKE ACTIVITIES

TECHNICAL FIELD

The present invention relates to compounds with thrombopoietin-like activity, and more specifically it relates to compounds which exhibit a thrombopoietic effect and the like and are useful for medical purposes.

BACKGROUND ART

Platelets, which constitute one type of blood cell components with important significance for hemostasis and thrombogenesis in the body, are released into the blood by a process in which hematopoietic stem cells in the bone marrow differentiate to megakaryocyte precursor cells which in turn differentiate to megakaryoblasts, and these megakaryoblasts then undergo maturation.

Numerous factors are known to function in the course of platelet production, and it is thrombopoietin (TPO) which is believed to be the most physiologically important factor (Lok, S. et al., Cell, 77, 1117(1994)). Thrombopoietin functions by activating its receptor c-mpl to transmit a signal into the cell (de Sauvage, F. J. et al., Nature, 369, 533(1994)), and its recognition as a specific factor in the megakaryocyte/platelet system has led to expectations for its application as an agent for treatment of various forms of thrombocytopenia.

However, using a protein such as thrombopoietin for medical purposes requires complex steps of culturing, purification and the like during its production process, and even when recombinant DNA techniques are used, the cost is generally much higher than for common low molecular weight compounds. Moreover, administration of formulations containing such proteins to humans introduces the problem of their antigenicity.

It has developed that low molecular weight compounds which have thrombopoietic action similar to that of thrombopoietin and low antigenicity, and which can be obtained by simple and inexpensive production processes. For example, Cwirla et al. have reported a peptide composed of 14 amino acids which can substitute for the action of thrombopoietin (Cwirla, S. E. et al., Science, 276, 1696 (1997)). Even such compounds, however, fail to solve the problems alluded to above and are still inadequate for practical use as drug agents.

DISCLOSURE OF THE INVENTION

The present invention has been accomplished in light of the aforementioned problems of the prior art, and its object is to provide low molecular compounds which have excellent thrombopoietic action and sufficiently low antigenicity, and which can be produced in a simple and inexpensive manner, as well as methods for their production, and pharmaceutical compositions, thrombopoietic agents and thrombocytopenia treatment agents which comprise the low molecular weight compounds.

As a result of much diligent research directed toward achieving this object, the present inventors have completed the present invention upon discovering that compounds having a specific triphenyl structure exhibit an excellent thrombopoietic effect and acceptably low antigenicity, and that these compounds can be obtained in a simple and inexpensive manner by specific production processes.

Specifically, a compound according to the invention is a compound represented by the following general formula (1):

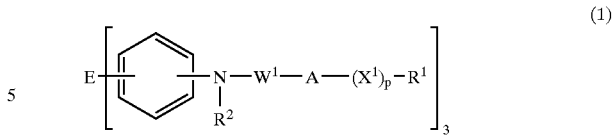

wherein E represents one selected from the group consisting of a methylidyne group and a nitrilo group, $R^1$ represents one selected from the group consisting of a hydrogen atom, a hydroxy group, a carboxy group, optionally substituted amino groups, optionally substituted aryl groups and optionally substituted heterocyclic groups, $R^2$ represents one selected from the group consisting of a hydrogen atom and alkyl groups, $W^1$ represents an amino acid residue, A represents one selected from the group consisting of a carbonyl group and a sulfonyl group, $X^t$ represents one selected from the group consisting of optionally substituted alkylene groups and optionally substituted alkenylene groups, and p represents 0 or 1.

The first production process for the compounds of the invention comprises a step of reacting a compound represented by the following general formula (2):

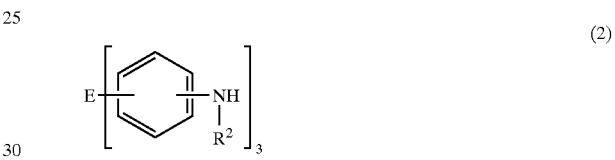

wherein E represents one selected from the group consisting of a methylidyne group and a nitrilo group and $R^2$ represents one selected from the group consisting of a hydrogen atom and alkyl groups, with at least one selected from the group consisting of $N^\alpha$-9-fluorenylmethoxycarbonylamino acid derivatives represented by the following general formula (3):

$$\text{Fmoc-W}^1 \quad (3)$$

wherein $W^1$ represents an amino acid residue and Fmoc represents a 9-fluorenylmethoxycarbonyl group bonded to the α-group of the amino acid residue, with the proviso that when the amino acid residue has a side chain functional group, the side chain functional group may be protected, and an Nα-t-butoxycarbonylamino acid derivative represented by the following general formula (4):

$$\text{Boc-W}^1 \quad (4)$$

wherein $W^1$ represents an amino acid residue and Boc represents a t-butoxycarbonyl group bonded to the α-amino group of the amino acid residue, with the proviso that when the amino acid residue has a side chain functional group, the side chain fictional group may be protected, in the presence of a condensation agent;

a second step of deprotecting the Fmoc group of Boc group of the compound obtained in the first step; and a third step of reacting the compound obtained in the second step with a compound represented by the following general formula (5):

$$R^1\text{—}(X^1)_p\text{—A—Z} \quad (5)$$

wherein $R^1$ represents one selected from the group consisting of a hydrogen atom, a hydroxy group, a carboxy group, optionally substituted amino groups, optionally substituted aryl groups and optionally substituted heterocyclic groups, $X^1$ represents one selected from the group consisting of optionally substituted alkylene groups and optionally substituted alkenylene groups, p represents 0 or 1, A represents one selected from the group consisting of a carbonyl group and a sulfonyl group, and Z represents one selected from the group consisting of a hydroxy group and halogen groups, in the presence of a condensation agent or a base, to obtain a compound represented by the following formula (1):

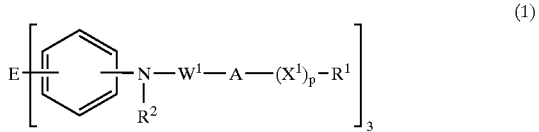

(1)

wherein E represents one selected from the group consisting of a methylidyne group and a nitrilo group, $R^1$ represents one selected from the group consisting of a hydrogen atom, a hydroxy group, a carboxy group, optionally substituted amino groups, optionally substituted aryl groups and optionally substituted heterocyclic groups, $R^2$ represents one selected from the group consisting of a hydrogen atom and alkyl groups, $W^1$ represents an amino acid residue, A represents one selected from the group consisting of a carbonyl group and a sulfonyl group, $X^1$ represents one selected from the group consisting of optionally substituted alkylene groups and optionally substituted alkenylene groups, and p represents 0 or 1.

The second production process for the compounds of the invention comprises a fourth step of reacting an amino acid derivative and a silylating agent;

a fifth step of reacting the compound obtained in the fourth step with a compound represented by the following general formula (5):

(5)

wherein $R^1$ represents selected from the group consisting of a hydrogen atom, a hydroxy group, a carboxy group, optionally substituted amino groups, optionally substituted aryl groups and optionally substituted heterocyclic groups, $X^1$ represents one selected from the group consisting of optionally substituted alkylene groups and optionally substituted alkenylene groups, p represents 0 or 1, A represents one selected from the group consisting of a carbonyl group and a sulfonyl group, and Z represents one selected from the group consisting of a hydroxy group and halogen groups; and a sixth step of reacting the compound obtained in the fifth step with a compound represented by the following general formula (2):

(2)

wherein E represents one selected from the group consisting of a methylidyne group and a nitril groups and $R^2$ represents one selected from the group consisting of a hydrogen atom and alkyl groups, in the presence of a condensation agent, to obtain a compound represented by the following formula (1):

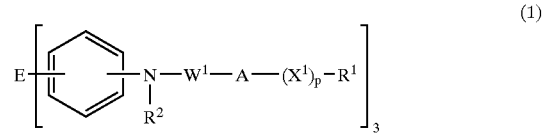

(1)

wherein E represents one selected from the group consisting of a methylidyne group and a nitrilo group, $R^1$ represents one selected from the group consisting of a hydrogen atom, a hydroxy group, a carboxy group, optionally substituted amino groups, optionally substituted aryl groups and optionally substituted heterocyclic groups, $R^2$ represents one selected from the group consisting of a hydrogen atom and alkyl groups, $W^1$ represents an amino acid residue, A represents one selected from the group consisting of a carbonyl group and a sulfonyl group, $X^1$ represents one selected from the group consisting of optionally substituted alkylene groups and optionally substituted alkenylene groups and p represents 0 or 1.

A pharmaceutical composition according to the invention comprises a compound according to the invention as described above or a pharmacologically acceptable salt thereof.

A thrombopoietic agent according to the invention also comprises a compound according to the invention as described above or a pharmacologically acceptable salt thereof.

A thrombocytopenia treatment agent according to the invention also comprises a compound according to the invention as described above or a pharmacologically acceptable salt thereof.

According to the invention, preferably $R^1$ in general formula (1) above is one selected from the group consisting of a hydrogen atom, a hydroxy group, a carboxy group, optionally substituted amino groups, optionally substituted aryl groups of 6–14 carbons and optionally substituted 5- to 14-membered heterocyclic groups, $R^2$ is one selected from the group consisting of a hydrogen atom and alkyl groups of 1–6 carbons, $W^1$ is an amino acid residue with a polar side chain, $X^1$ is one selected from the group consisting of optionally substituted alkylene groups of 1–6 carbons and optionally substituted alkenylene groups of 2–6 carbons, and p represents 0 or 1;

more preferably, $R^1$ in general formula (1) above is one selected from the group consisting of a hydrogen atom, optionally substituted monocyclic or fused ring aryl groups of 6–10 carbons and optionally substituted 5- to 9-membered monocyclic or fused ring heterocyclic groups, $R^2$ is one selected from the group consisting of an hydrogen atom and linear or branched alkyl groups of 1–6 carbons, $W^1$ is a basic amino acid residue, and $X^1$ is one selected from the group consisting of alkylene groups of 1–3 carbons and alkenylene groups of 2–4 carbons;

still more preferably, $R^1$ in general formula (1) above is one selected from the group consisting of optionally substituted monocyclic or fused ring aryl groups of 6–10 carbons and optionally substituted 5- to 9-membered monocyclic or fused ring heterocyclic groups, $R^2$ is one selected from the group consisting of a hydrogen atom and linear or branched alkyl groups of 1–6 carbons, $W^1$ is a basic amino acid residue, and $X^1$ is one selected from the group consisting of alkylene groups of 1–3 carbons and alkenylene groups of 2–4 carbons;

even more preferably, $W^1$ in general formula (1) above is an amino acid residue having on the side chain at least one selected from the group consisting of an amino group, a guanidyl group, alkylamino groups and alkylguanidyl groups of 1–6 carbons and dialkylamino groups of 2–12 carbons;

yet more preferably, A in general formula (1) above is carbonyl, $X^1$ is a methylene group and p is 0 or 1;

and most preferably, the triphenylmethane derivative is one selected from the group consisting of:

tris[4-[N-α-[2-(1H-indol-3-yl)acetyl]-L-lysyl]aminophenyl]methane hydrochloride,
tris[4-[N-α-[2-(5-methoxy-2-methyl-1H-indol-3-yl)acetyl]-L-lysyl]aminophenyl]methane hydrochloride,
tris[4-[N-α-[2-(2-methyl-1H-indol-3-yl)acetyl]-L-lysyl]aminophenyl]methane hydrochloride,
tris[4-(N-α-L-tryptophyl-L-lysyl)aminophenyl]methane hydrochloride,
tris[4-[N-α-[2-(thiophen-3-yl)acetyl]-L-lysyl]aminophenyl]methane hydrochloride,
tris[4-(N-α-L-phenylalanyl-L-lysyl)aminophenyl]methane hydrochloride,
tris[4-[N-α-(3-pyridylcarbonyl)-L-lysyl]aminophenyl]methane hydrochloride,
tris[4-[N-α-[2-(5-hydroxy-1H-indol-3-yl)acetyl]-L-lysyl]aminophenyl]methane hydrochloride,
tris[4-[N-α-[2-(4-hydroxyphenyl)acetyl]-L-lysyl]aminophenyl]methane hydrochloride,
tris(4-[N-α-[2-[2-methyl-1H-indol-3-yl)acetyl]-D-lysyl]aminophenyl]methane,
tris[4-[N-α-[2-(thiophen-3-yl)acetyl]-D-lysyl]aminophenyl]methane hydrochloride,
tris[4-[N-α-[2-(1H-indol-3-yl)acetyl]-N-ε-dimethyl-L-lysyl]aminophenyl]methane,
tris[4-[N-α-[2-(2-methyl-1H-indol-3-yl)acetyl]-N-ε-dimethyl-L-lysyl]aminophenyl]methane,
tris[4-[N-α-[2-(5-methoxy-2-methyl-1H-indol-3-yl)acetyl]-N-ε-dimethyl-L-lysyl]aminophenyl]methane,
tris[4-[N-α-[2-(thiophen-3-yl)acetyl]-N-ε-dimethyl-L-lysyl]aminophenyl]methane,
tris[4-[N-[2-(1H-indol-3-yl)acetyl]-S-(3-aminopropyl)-L-cystyl]aminophenyl]methane hydrochloride,
tris[4-[N-α-[2-(thiophen-3-yl)acetyl]-L-arginyl]aminophenyl]methane hydrochloride,
tris[4-[N-α-[2-(2-methyl-1H-indol-3-yl)acetyl]-D-arginyl]aminophenyl]methane hydrochloride,
tris[4-[N-α-[2-(thiophen-3-yl)acetyl]-D-arginyl]aminophenyl]methane hydrochloride,
tris[4-[β-aminomethyl-N-[2-(1H-indol-3-yl)acetyl]-L-alanyl]aminophenyl]methane trifluoroacetate,
tris[4-[β-aminomethyl-N-[2-(2-methyl-1H-indol-3-yl)acetyl]-L-alanyl]aminophenyl]methane trifluoroacetate,
tris[4-[β-aminomethyl-N-[2-(5-methoxy-2-methyl-1H-indol-3-yl)acetyl]-L-alanyl]aminophenyl]methane trifluoroacetate,
tris[4-[N-α-[2-(1H-indol-3-yl)acetyl]-L-ornithyl]aminophenyl]methane trifluoroacetate,
tris[4-[N-α-[2-(5-methoxy-2-methyl-1H-indol-3-yl)acetyl]-L-ornithyl]aminophenyl]methane trifluoroacetate,
tris[(4-[N-α-[2-(6-methoxy-2-methyl-1H-indol-3-yl)acetyl]-D-lysyl]aminophenyl]methane hydrochloride,
tris[4-[N-α-[2-(2-ethyl-1H-indol-3-yl)acetyl]-D-lysyl]aminophenyl]methane hydrochloride,
tris[4-[N-α-(5-hydroxy-1H-indol-2-yl)carbonyl-D-lysyl]aminophenyl]methane hydrochloride,
tris[4-[N-α-(1H-indol-4-yl)carbonyl-D-lysyl]aminophenyl]methane hydrochloride,
tris[4-[N-α-[2-(7-methyl-1H-indol-3-yl)acetyl]-D-lysyl]aminophenyl]methane hydrochloride,
tris[4-[N-α-(pyrazin-2-yl)carbonyl-D-lysyl]aminophenyl]methane hydrochloride,
tris[4-[N-α-[2-(3-hydroxyphenyl)acetyl]-D-lysyl]aminophenyl]methane hydrochloride,
tris[4-[N-α-(D-tyrosyl)-D-lysyl]aminophenyl]methane hydrochloride,
tris[4-[N-α-(D-tryptophyl)-D-lysyl]aminophenyl]methane hydrochloride,
tris[4-[N-α-[2-(thiophen-2-yl)acetyl]-D-lysyl]aminophenyl]methane hydrochloride,
tris[4-[N-α-[2-(pyridin-2-yl)acetyl]-D-lysyl]aminophenyl]methane hydrochloride,
tris[4-[N-α-[2-(pyridin-4-yl)acetyl]-D-lysyl]aminophenyl]methane hydrochloride,
tris[4-[N-α-(3-hydroxybenzoyl)-D-lysyl]aminophenyl]methane trifluoroacetate,
tris[4-[N-α-(2-phenylacetyl)-D-lysyl]aminophenyl]methane trifluoroacetate,
tris[4-[N-α-[2-(3,4-dihydroxyphenyl)acetyl]-D-lysyl]aminophenyl]methane trifluoroacetate,
tris[4-[N-α-(6-hydroxynaphthalen-1-yl)carbonyl-D-lysyl]aminophenyl]methane trifluoroacetate,
tris[4-(N-α-benzoyl-D-lysyl)aminophenyl]methane trifluoroacetate,
tris[4-(N-α-benzoyl-L-lysyl)aminophenyl]methane trifluoroacetate,
tris[4-[N-α-(2-phenylacetyl)-L-lysyl]aminophenyl]methane trifluoroacetate,
tris[4-[N-α-(6-hydroxynaphthalen-1-yl)carbonyl-L-lysyl]aminophenyl]methane trifluoroacetate, and
tris[4-[N-α-[2-(1H-indol-3-yl)acetyl]-D-lysyl]aminophenyl]amine trifluoroacetate.

BEST MODE FOR CARRYING OUT THE INVENTION

Figure 1:
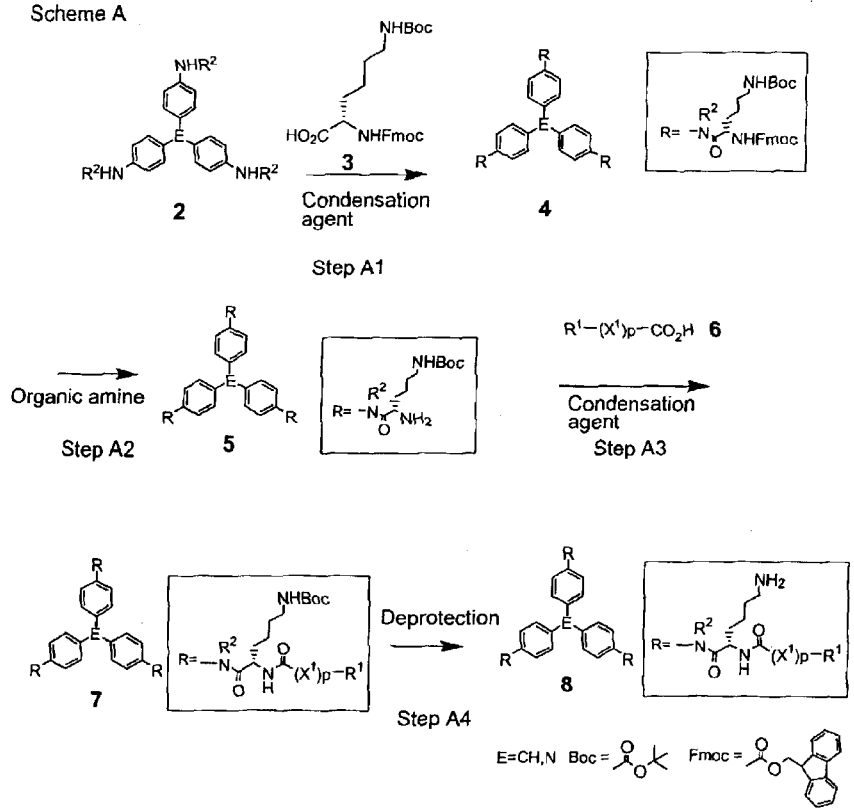
FIG. 1 is a reaction scheme diagram showing an example of the first production process for a compound according to the invention.

Preferred modes of the invention will now be explained in detail.

The compounds of the invention are compounds represented by the following general formula (1):

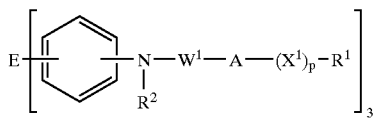

(1)

and their pharmacologically acceptable salts. The compounds of the invention exhibit activity similar to that exhibited by thrombopoietin for its receptor (thombopoietin-like activity), and therefore have a thrombopoietic effect.

Pharmacologically acceptable salts are salts which do not affect body function when administered, and these may be obtained by addition of conventional publicly known acids or bases to the compounds represented by general formula (1). As pharmacologically acceptable acid addition salts there may be specifically mentioned inorganic acid salts such as hydrochlorides, nitrates and phosphates, and organic acid salts such as acetates, lactates, oxalates, citrates, tartrates and p-toluenesulfonates. As pharmacologically acceptable base addition salts there may be specifically mentioned inorganic salts such as sodium salts, potassium salts, calcium salts, aluminum salts and ammonium salts, and organic amine salts. Hydrochloride and trifluoroacetate salts are preferred among these, with hydrochloride salts being particularly preferred.

In general formula (1), E is a methylidyne group or a nitrilo group. A methylidyne group according to the invention is a group represented by CH and having 3 bonds, while a nitrilo group is a group represented by N and having 3 bonds. That is, when E is a methylidyne group, the compound represented by general formula (1) is a triphenylmethane derivative. When E is a nitrilo group, the compound represented by general formula (1) is a triphenylamine derivative.

In general formula (1), $R^1$ represents one selected from the group consisting of a hydrogen atom, hydroxy, carboxy, optionally substituted amino, optionally substituted aryl and optionally substituted heterocyclic groups. As substituents on the aryl groups or heterocyclic groups there may be specifically mentioned halogen atoms, linear or branched alkyl groups of 1–6 carbons, linear or branched halogenated alkyl groups of 1–6 carbons, optionally substituted aryl groups, optionally substituted heterocyclic groups, hydroxy group, alkoxy groups, halogenated alkoxy groups, a carboxy group, alkylcarbonyl groups, arylcarbonyl groups, aralkyl groups, a thiol group, a cyano group, an isocyano group, optionally substituted amino groups, optionally substituted amide groups, a nitro group, or groups represented by the following formula:

(where n is 1 or 2, and $R^3$ represents a hydrogen atom, linear or branched alkyl groups of 1–3 carbons, amino groups optionally substituted with alkyl groups of 1–3 carbons, amino groups optionally substituted with aryl groups, or amino groups optionally substituted with heterocyclic groups).

When $R^1$ is an aryl group of 6–14 carbons or a 5- to 14-membered heterocyclic group, the substituents preferred among those mentioned above are hydroxyl, methyl, ethyl, isopropyl, optionally substituted phenyl, benzyloxy, methoxy, fluoro, bromo, chloro, trifluoromethyl, trifluoromethoxy, carboxy, amino, acetylamino and dimethylamino groups.

As the aryl groups of the optionally substituted aryl groups for $R^1$ in general formula (1) there may be specifically mentioned pheny, naphthalenyl, anthranyl, indenyl, fluorenyl and phenanthrenyl, among which aryl groups of 6–14 carbons are preferred, monocyclic or fused ring aryl groups of 6–10 carbons are more preferred, and phenyl and naphthalenyl are particularly preferred.

As the heterocyclic groups of the optionally substituted heterocyclic groups for $R^1$ in general formula (1) there may be specifically mentioned indolyl, pyridyl, pyrrole, benzothienyl, thienyl, pyrimidyl, furyl, thiazole, oxazole, imidazole, benzofuryl, benzimidazole, benzothiazole, benzoxazole, oxyindole, 2-thiantholenyl, tetrazole, 2H-pyran-3-yl, isobenzofuranyl, 2H-chromen-3-yl, xanthenyl, phenoxathienyl, 2H-pyrrol-3-yl, pyrazolyl, isothiazole, isoxazole, pyrazinyl, pyridazinyl, indolidinyl, isoindolyl, 3H-indol-2-yl, 1H-indazolyl, 8-purinyl, 4H-quinolidin-2-yl, isoquinolyl, quinolyl, acridinyl, perimidinyl, 1,7-phenanthrolin-3-yl, phenazinyl, phenarsazinyl, phenothiazinyl, furazanyl, phenoxazinyl, isochromanyl, chromanyl, pyrrolidinyl, 2-pyrrolin-3-yl, imidazolidinyl, 2-imidazolin-4-yl, pyrazolidinyl, 3-pyrazolin-2-yl, piperidyl, piperazinyl, indolinyl, isoindolinyl, quinuclidinyl, morpholinyl, pyrazolyl, 5-oxo-2-pyrazolyl, isooxazolyl, hydantoyl, uracil, pyrazyl, benzodioxanyl, rhodanyl, benzodioxan-2-yl and rhodanin-3-yl groups. Among these, 5- to 14-membered heterocyclic groups are preferred, 5- to 9-membered monocyclic or fused ring heterocyclic groups are more preferred, and indolyl, pyridyl, pyrrole, benzothienyl, thienyl, pyrimidyl, furyl, thiazole, oxazole, imidazole, benzofuryl, benzimidazole, benzothiazole, benzoxazole, pyrazolyl, 5-oxo-2-pyrazolyl, isooxazolyl, hydantoyl, uracil, pyrazyl, benzodioxanyl, rhodanyl, benzodioxan-2-yl, rhodanin-3-yl and oxyindole are particularly preferred. As hetero atoms on the same heterocyclic group there are preferred nitrogen, sulfur and/or oxygen atoms, and the number of hetero atoms on the same heterocyclic group is preferably 1 to 4.

In general formula (1), $R^2$ represents a hydrogen atom or alkyl groups. As alkyl groups there may be specifically mentioned methyl, ethyl, n-propyl, i-propyl, n-butyl, sec-butyl, t-butyl, pentyl, hexyl and heptyl. According to the invention, $R^2$ in general formula (1) is preferably a hydrogen atom or an alkyl group of 1–6 carbons, more preferably a hydrogen atom or an alkyl group of 1–3 carbons, and most preferably a hydrogen atom.

In general formula (1), $W^1$ represents an amino acid residue. Such an amino acid residue forms an amide bond with the adjacent nitrogen atom, and forms an amide bond or a sulfonamide bond with the group represented by A. As amino acid residues there may be specifically mentioned alanyl, arginyl, asparaginyl, α-aspartyl, β-aspartyl, cysteinyl, glutaminyl, α-glutamyl, γ-glutamyl, glycyl, histidyl, isoleucyl, leucyl, lysyl, methionyl, phenylalanyl, prolyl, seryl, threonyl, tryptophyl, tyrosyl, valyl, β-alanyl, ornithyl, tyronyl, sarcosyl, norvalyl, norleucyl, lanthionyl, homoseryl, cystyl, aspartoyl, glutamoyl, cystathionyl, 2,3-diaminopropionyl, 2,4-diaminobutyryl, 4-nitrophenylalanyl, 4-aminophenylalanyl, β-methylsulfonylmethylalanyl, citrullyl, β-(pyridin-2-yl)alanyl, β-(pyridin-4-yl)alanyl, O-benzylseryl, N-ε-acetyllysyl, N-τ-benzyloxymethylhistidyl, O-benzyltyrosyl, N-δ-(pyrazin-2-yl carbonylornithyl, N-δ-triphenylmethylglutaminyl, N-ε-dimethyllysyl and S-(3-aminopropyl)cystyl, among which amino acid residues with basic side chains are more preferred. As amino acid residues with basic side chains there may be specifically mentioned arginyl, ornithyl, histidyl, lysyl, 2,3-diaminopropionyl, 2,4-diaminobutyryl, 4-aminophenylalanyl, β-(pyridin-2-yl)alanyl, β-(pyridin4- yl)alanyl, N-δ-(pyrazin-2-yl)carbonylornithyl, N-ε-dimethyllysyl and S-(3-aminopropyl)cystyl groups, among which arginyl, ornithyl, lysyl, 2,4-diaminobutyryl and N-ε-dimethyllysyl are particularly preferred. Preferred amino acid residues also include those with amino, guanidyl, alkylamino of 1–6 carbons and dialkylamino of 2–12 carbons on the side chains. The preferred amino acid residues may be in the D-form, L-form or racemic form.

In general formula (1), $X^1$ represents an optionally substituted alkylene group or an optionally substituted alkenylene group, and p represents 0 or 1.

As substituents which may be present on the alkylene group or the alkenylene group represented by $X^1$ in general formula (1) there may be specifically mentioned a hydroxyl group, halogen atoms, linear or branched alkyl groups of 1–6 carbons, linear or branched halogenated alkyl groups of 1–6 carbons, alkoxy groups, carboxy group, thiol group, cyano group, isocyano group, optionally substituted amino groups, optionally substituted amide groups and a nitro group, and groups represented by the following formula:

where n is 1 or 2, and $R^3$ represents a hydrogen atom, a linear or branched alkyl group of 1–3 carbons, an amino group optionally substituted with an alkyl group of 1–3 carbons, an amino group optionally substituted with an aryl group or an amino group optionally substituted with a heterocyclic group, among which a hydroxyl group and an optionally substituted amino group are preferred.

As optionally substituted alkylene groups for $X^1$ in formula (1) above there may be specifically mentioned methylene, ethylene, propylene, butylene, pentylene, hexylene and heptylene, among which alkylene groups of 1–6 carbons such as methylene, ethylene, propylene, butylene, pentylene and hexylene are preferred, and linear alkylene groups of 1–3 carbons such as methylene, ethylene and propylene are more preferred. On the other hand, as optionally substituted alkenylene groups for $X^1$ in formula (1) above there may be specifically mentioned ethenylene, propenylene, butenylene, pentenylene and hexenylene, among which linear alkenylene groups of 2–4 carbons such as ethenylene, propenylene and butenylene are preferred, and ethenylene, propenylene and butenylene are especially preferred. Preferred among these alkylene groups and alkenylene groups are methylene, ethylene, propylene, butylene, pentylene and hexylene, with methylene, ethylene and propylene being particularly preferred.

The group represented by A in formula (1) is a carbonyl group or a sulfonyl group, and preferably a carbonyl group. When A is a carbonyl group, preferably p is 0 and $R^2$ is a hydrogen atom, or alternatively p is 1, $X^1$ is a methylene group and $R^2$ is a hydrogen atom.

Compounds of the invention having the structure described above exhibit a significantly high thrombopoietic effect, with acceptably controlled antigenicity, and can be produced in a simple and inexpensive manner. Especially preferred are compounds selected from the group consisting of:

tris[4-[N-α-[2-(1H-indol-3-yl)acetyl]-L-lysyl]aminophenyl]methane hydrochloride, tris[4-[N-α[2-(5-methoxy-2-methyl-1H-indol-3-yl)acetyl]-L-lysyl]aminophenyl]methane hydrochloride, tris[4-[N-α-[2-(2-methyl-1H-indol-3-yl)acetyl]-L-lysyl]aminophenyl]methane hydrochloride, tris[4-(N-α-L-tryptophyl-L-lysyl)aminophenyl]methane hydrochloride, tris[4-[N-α-[2-(thiophen-3-yl)acetyl]-L-lysyl]aminophenyl]methane hydrochloride, tris[4-(N-α-L-phenylalanyl-L-lysyl)aminophenyl]methane hydrochloride, tris[4-[N-α-(3-pyridylcarbonyl)-L-lysyl]aminophenyl]methane hydrochloride, tris[4-[N-α-[2-(5-hydroxy-1H-indol-3-yl)acetyl]-L-lysyl]aminophenyl]methane hydrochloride, tris[4-[N-α-[2-(4-hydroxyphenyl)acetyl]-L-lysyl]aminophenyl]methane hydrochloride, tris[4-[N-α-[2-(2-methyl-1H-indol-3-yl)acetyl]-D-lysyl]aminophenyl]methane, tris[4-[N-α-[2(thiophene-3-yl)acetyl]-D-lysyl]aminophenyl]methane hydrochloride, tris[4-[N-α-[2-(1H-indol-3-yl)acetyl]-N-ε-dimethyl-L-lysyl]aminophenyl]methane, tris[4-[N-α-[2(2-methyl-1H-indol-3-yl)acetyl]-N-ε-dimethyl-L-lysyl]aminophenyl]methane, tris[4-[N-α-(2-(5-methoxy-2-methyl-1H-indol-3-yl)acetyl)-N-ε-dimethyl-L-lysyl]aminophenyl]methane, tris[4-[N-α-[2-(thiophen-3-yl)acetyl]-N-ε-dimethyl-L-lysyl]aminophenyl]methane, tris[4-[N-[2-(1H-indol-3-yl)acetyl]-S-(3-aminopropyl)-L-cystyl]aminophenyl]methane hydrochloride, tris[4-[N-α-[2-(thiophen-3-yl)acetyl]-L-arginyl]aminophenyl]methane hydrochloride, tris(4-[N-α-[2-[2-methyl-1H-indol-3-yl)acetyl]-D-arginyl]aminophenyl]methane hydrochloride, tris[4-[N-α-[2-(thiophen-3-yl)acetyl]-D-arginyl]aminophenyl]methane hydrochloride, tris[4-[β-aminomethyl-N-[2-(1H-indol-3-yl)acetyl]-L-alanyl]aminophenyl]methane trifluoroacetate, tris[4-[β-aminomethyl-N-[2-(2-methyl-1H-indol-3-yl)acetyl]-L-alanyl]aminophenyl]methane trifluoroacetate, tris[4-[β-aminomethyl-N-[2-(5-methoxy-2-methyl-1H-indol-3-yl)acetyl]-L-alanyl]aminophenyl]methane trifluoroacetate, tris[4-[N-α-[2-(1H-indol-3-yl)acetyl]-L-ornithyl]aminophenyl]methane trifluoroacetate, tris[4-[N-α-[2-(5-methoxy-2-methyl-1H-indol-3-yl)acetyl]-L-ornithyl]aminophenyl]methane trifluoroacetate, tris[4-[N-α-[2-(6-methoxy-2-methyl-1H-indol-3-yl)acetyl]-D-lysyl]aminophenyl]methane hydrochloride, tris[4-[N-α-[2-(2-ethyl-1H-indol-3-yl)acetyl]-D-lysyl]aminophenyl]methane hydrochloride, tris[4-[N-α-(5-hydroxy-1H-indol-2-yl)carbonyl-D-lysyl]aminophenyl]methane hydrochloride, tris[4-[N-α-(1H-indol-4-yl)carbonyl-D-lysyl]aminophenyl]methane hydrochloride, tris[4-[N-α-[2-(7-methyl-1H-indol-3-yl)acetyl]-D-lysyl]aminophenyl]methane hydrochloride, tris[4-[N-α-(pyrazin-2-yl)carbonyl-D-lysyl]aminophenyl]methane hydrochloride, tris[4-[N-α[2-(3-hydroxyphenyl)acetyl]-D-lysyl]aminophenyl]methane hydrochloride, tris[4-[N-α-(D-tyrosyl)-D-lysyl]aminophenyl]methane hydrochloride, tris[4-[N-α-(D-tryptophyl)-D-lysyl]aminophenyl]methane hydrochloride, tris[4-[N-α-[2-(thiophen-2-yl)acetyl]-D-lysyl]aminophenyl]methane hydrochloride, tris[4-[N-α-[2-(pyridin-2-yl)acetyl]-D-lysyl]aminophenyl]methane hydrochloride, tris[4-[N-α-[2-(pyridin-4-yl)acetyl]-D-lysyl]aminophenyl]methane hydrochloride, tris[4-[N-α-(3-hydroxybenzoyl)-D-lysyl]aminophenyl]methane trifluoroacetate, tris[4-[N-α-(2-phenylacetyl)-D-lysyl]aminophenyl]methane trifluoroacetate, tris[4-[N-α-[2-(3,4-dihydroxyphenyl)acetyl]-D-lysyl]aminophenyl]methane trifluoroacetate, tris[4-[N-α-(6-hydroxynaphthalen-1-yl)carbonyl-D-lysyl]aminophenyl]methane trifluoroacetate, tris[4-(N-α-benzoyl-D-lysyl)aminophenyl]methane trifluoroacetate, tris[4-(N-α-benzoyl-L-lysyl)aminophenyl]methane trifluoroacetate, tris[4-[N-α-(2-phenylacetyl)-L-lysyl]aminophenyl]methane trifluoroacetate, tris[4-[N-α-(6-hydroxynaphthalen-1- yl)carbonyl-L-lysyl]aminophenyl]methane trifluoroacetate and tris[4[N-α-[2-(1H-indol-3-yl)acetyl]-D-lysyl] aminophenyl]amine trifluoroacetate.

Especially preferred are compounds selected from the group consisting of:
tris[4-[N-α-[2-(2-methyl-1H-indol-3-yl)acetyl]-D-lysyl] aminophenyl]methane, tris[4-[N-α-[2-(thiophen-3-yl) acetyl]-D-lysyl]aminophenyl]methane hydrochloride, tris[4-[N-α-[2-(1H-indol-3-yl)acetyl]-N-ε-dimethyl-L-lysyl]aminophenyl]methane, tris[4-[N-α-[2-(2-methyl-1H-indol-3-yl)acetyl]-N-ε-dimethyl-L-lysyl] aminophenyl]methane, tris[4-[N-α-[2-(5-methoxy-2-methyl-1H-indol-3-yl)acetyl]-N-ε-dimethyl-L-lysyl] aminophenyl]methane, tris[4-[N-α-[2-(thiophen-3-yl) acetyl]-N-ε-dimethyl-L-lysyl]aminophenyl]methane, tris[4-[N-α-[2-(thiophen-3-yl)acetyl]-L-arginyl] aminophenyl]methane hydrochloride, tris[4-[N-α-[2-(2-methyl-1H-indol-3-yl)acetyl]-D-arginyl] aminophenyl]methane hydrochloride, tris[4-[(N-α-[2-(thiophen-3-yl)acetyl]-D-arginyl]aminophenyl] methane hydrochloride, tris[4-[N-α-[2-(6-methoxy-2-methyl-1H-indol-3-yl)acetyl]-D-lysyl]aminophenyl] methane hydrochloride, tris[4-[N-α-[2-(2-ethyl-1H-indol-3-yl)acetyl]-D-lysyl]aminophenyl]methane hydrochloride, tris[4-[N-α-(1H-indol-4-yl)carbonyl-D-lysyl]aminophenyl]methane hydrochloride, tris[4-[N-α-[2-(7-methyl-1H-indol-3-yl)acetyl]-D-lysyl] aminophenyl]methane hydrochloride, tris[4-[N-α-(D-tryptophyl)-D-lysyl]aminophenyl]methane hydrochloride, tris[4-[N-α-(2-phenylacetyl)-D-lysyl] aminophenyl]methane trifluoroacetate, tris[4-[N-α-(6-hydroxynaphthalen-1-yl)carbonyl-D-lysyl] aminophenyl]methane trifluoroacetate, tris[4-(N-α-benzoyl-D-lysyl)aminophenyl]methane trifluoroacetate, tris[4-(N-α-benzoyl-L-lysyl) aminophenyl]methane trifluoroacetate, tris[4-[N-α-(2-phenylacetyl)-L-lysyl]aminophenyl]methane trifluoroacetate, tris[4-[N-α-(6-hydroxynaphthalen-1-yl)carbonyl-L-lysyl]aminophenyl]methane trifluoroacetate and tris[4-[N-α-[2-(1H-indol-3-yl)acetyl]-D-lysyl]aminophenyl]amine trifluoroacetate.

Processes for producing the compounds of the invention will now be explained.

The first production process for the compounds of the invention comprise a first step of reacting a compound represented by te following general formula (2):

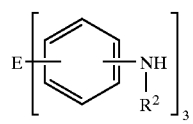

(2)

wherein E represents one selected from the group consisting of a methylidyne group and nitrilo group and $R^2$ represents one selected from the group consisting of hydrogen atom and alkyl groups,
with at least one selected from the group consisting of Nα-9-fluorenylmethoxycarbonylamino acid derivatives represented by the following general formula (3):

Fmoc-$W^1$ (3)

wherein $W^1$ represents amino acid residue and Fmoc represents 9-fluoroenylmethoxycarbonyl group bonded to the α-amino group of the amino acid residue, with the proviso that when the amino acid residue has a side chain functional group, the side chain functional group may be protected, and a Nα-t-butoxycarbonylamino acid derivative represented by the following general formula (4):

Boc-$W^1$ (4)

wherein $W^1$ represents a amino acid residue and Boc represents a t-butoxycabonyl group bonded to the α-amino group of the amino acid residue, with the proviso that when the amino acid residue has a side chain functional group, the side chain functional group may be protected,
in the presence of a condensation agent;
a second step of deprotecting the Fmoc group or Boc group of the compound obtained in the first step; and
a third step of reacting the compound obtained in the second step with a compound represented by the following general formula (5):

$R^1$—$(X^1)_p$—A—Z (5)

wherein $R^1$ represents one selected from the group consisting of a hydrogen atom, a hydroxy group, a carboxy group, optionally substituted amino groups, optionally substituted aryl groups and optionally substituted heterocyclic groups, $X^1$ represents one selected from the group consisting of optionally substituted alkylene groups and optionally substituted alkenylene groups, p represents 0 or 1, A represents one selected from the group consisting of a carbonyl group and a sulfonyl group, and Z represents a hydroxy group or a halogen group, in the presence of a condensation agent or a base, to obtain a compound represented by the following formula (1):

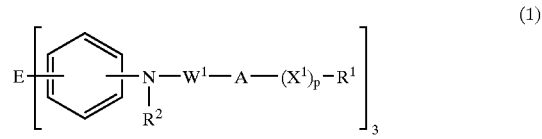

(1)

wherein E represents one selected from the group consisting of a methylidyne group and a nitrilo group, $R^1$ represents one selected from the group consisting of a hydrogen atom, a hydroxy group, a carboxy group, optionally substituted amino groups, optionally substituted aryl groups and optionally substituted heterocyclic groups, $R^2$ represents one selected from the group consisting of a hydrogen atom and alkyl groups, $W^1$ represents an amino acid residue, A represents one selected from the group consisting of a carbonyl group and a sulfonyl group, $X^1$ represents one selected from the group consisting of optionally substituted alkylene groups and optionally substituted alkenylene groups, and p represents 0 or 1.

In general formulas (2) to (5) above, E, $R^1$, $R^2$, $W^1$, A, $X^1$ and p may be the same specific groups as mentioned for E, $R^1$, $R^2$, $W^1$, A, $X^1$ and p in general formula (1), and the compounds represented by formulas (2) to (5) may be selected as appropriate based on the structure of the target compound.

FIG. 1 is a reaction scheme diagram showing an example of the first production process according to the invention. In FIG. 1, first Compound 2, which is a compound represented by general formula (2) (triphenylmethane derivative or triphenylamine derivative), is reacted with Compound 3, which is $N^α$-9-fluorenylmethoxycarbonylamino acid derivative, in an inert solvent in the presence of a condensation agent, to obtain Compound 4 (Step A1).

The compounds of the invention (triphenylmethane derivatives or triphenylamine derivatives represented by general formula (1)) include those with functional groups such as amino, carboxy, hydroxy and thiol groups substituted on the side chain of the amino acid residue ($W^1$), and for production of such a compound having a side chain functional group in the amino acid residue, it is preferred to use as the starting compound an $N^\alpha$-9-fluorenylmethoxycarbonylamino acid derivative 3 with the side chain functional group protected. Using an $N^\alpha$-9-fluorenylmethoxycarbonylamino acid derivative with the side chain functional group protected will tend to improve the selectivity in the reaction involving the α-amino group in the steps described below. As protecting groups for the side chain functional groups there may be specifically mentioned substituted sulfonyl groups such as p-toluenesulfonyl and 2,2,4,6,7-pentamethyl-dihydrobenzofuran-5-sulfonyl; optionally substituted alkyl groups such as methyl, methoxymethyl, ethoxyethyl, t-butyl and triphenylmethyl; substituted silyl groups such as trimethylsilyl, triethylsilyl, triisopropylsilyl, t-butyldimethylsilyl and t-butyldiphenylsilyl; substituted phenyl groups such as p-chlorophenyl, p-methoxyphenyl and 2,4-dinitrophenyl; optionally substituted benzyl groups such as benzyl, p-methoxybenzyl, 3,4-dimethoxybenzyl, o-nitrobenzyl, p-nitrobenzyl, p-chlorobenzyl, p-bromobenzyl, 2,6-dichlorobenzyl, 2,6-dimethylbenzyl, p-cyanobenzyl and p-phenylbenzyl; alkylcarbonyl groups such as formyl, acetyl, propionyl, butyryl, valeryl, levulinyl and pivaloyl; arylcarbonyl groups such as benzoyl, 4-nitrobenzoyl, 4-chlorobenzoyl, 2-iodobenzoyl, 4-methoxybenzoyl, p-phenylbenzoyl, 2,4,6-triphenylbenzoyl, o-(dibromomethyl)benzoyl, 2-(methylthiomethoxymethyl) benzoyl, o-(methoxycarbonyl)benzoyl, naphthoyl, toluoyl and 9-fluorenecarbonyl; and oxycarbonyl groups such as methoxycarbonyl, ethoxycarbonyl, t-butoxycarbonyl, benzyloxycarbonyl and 4-methoxybenzyloxycarbonyl. These protecting groups may be easily removed from the side chain functional groups by the methods described hereunder.

As condensation agents to be used in Step A1 there may be specifically mentioned O-(7-azabenzotriazol-1-yl)-1,1,3,3-tetramethyluronium hexafluorophosphate (HATU), 1-ethyl-3-(3-dimethylaminopropyl) carbodiimide (EDC), dicyclohexyl carbodiimide, diisopropyl carbodiimide, benzotriazol-1-yloxy-tris(dimethylamino)phosphonium hexafluorophosphate, diphenylphosphoryl azide and diphenylphosphoryl cyanide, among which O-(7-azabenzotriazol-1-yl)-1,1,3,3-tetramethyluronium hexafluorophosphate and 1-ethyl-3-(3-dimethylaminopropyl) carbodiimide are preferred for use.

There are no particular restrictions on the inert solvent used in Step A1 so long as it does not participate in the reaction, and specifically there may be mentioned hydrocarbons such as hexane, cyclohexane, benzene, toluene and xylene; halogenated hydrocarbons such as methylene chloride ($CH_2Cl_2$), chloroform, 1,2-dichlorethane and tetrachloromethane; ethers such as ether, tetrahydrofuran and dioxane; amides such as N,N-dimethylformamide (DMF), N,N-dimethylacetamide, N-methyl-2-pyrrolidone and hexamethylphosphoramide; sulfoxides such as dimethylsulfoxide; and mixed solvents comprising two or more of these. Among such solvents there are preferred halogenated hydrocarbons and/or amides, with N,N-dimethylformamide or mixed solvents of methylene chloride and N,N-dimethylformamide being especially preferred. When a mixed solvent of methylene chloride and N,N-dimethylformamide is used, the mixing ratio (volume ratio) will normally be methylene chloride:N,N-dimethylformamide=1:9–9:1, and preferably methylene chloride:N,N-dimethylformamide=5:5.

In Step A1 there are preferably also used additives including organic amines such as N-methylmorpholine (NMM) and 4-dimethylaminopyridine (DMAP), and N-hydroxy derivatives such as N-hydroxysuccinimide, 1-hydroxybenzotriazole and 3-hydroxy-4-oxo-3,4-dihydro-1,2,3-benzotriazine. Using such additives in Step A1 will tend to increase the reaction yield. Preferred of such additives are organic amines, among which N-methylmorpholine and 4-dimethylaminopyridine are especially preferred.

There are no particular restrictions on the reaction conditions for Step A1, but the reaction temperature will generally be between −20° C. and 100° C., and preferably 0–40° C. The reaction time for Step A1 will differ depending on the reaction temperature and other reaction conditions, but will usually be from 1 hour to 5 days, and preferably from 3 hours to 3 days.

Compound 4 obtained in Step A1 is then reacted with an organic amine in an inert solvent to obtain Compound 5 (Step A2). As organic amines to be used in Step A2 there may be mentioned piperidine, diethylamine, dimethylamine, diisopropylamine, dicyclohexylamine, piperazine and morpholine, among which piperidine and diethylamine are preferred.

The inert solvent to be used in Step A2 is not particularly restricted so long as it does not participate in the reaction, and specifically there may be mentioned hydrocarbons such as hexane, cyclohexane, benzene, toluene and xylene; halogenated hydrocarbons such as methylene chloride, chloroform, 1,2-dichloroethane and tetrachloromethane; ethers such as ether, tetrahydrofuran and dioxane; amides such as N,N-dimethylformamide, N,N-dimethylacetamide, N-methyl-2-pyrrolidone and hexamethylphosphoramide; sulfoxides such as dimethylsulfoxide; and mixed solvents comprising two or more of these, among which amides are preferred for use, and N,N-dimethylformamide is particularly preferred.

There are no particular restrictions on the reaction conditions for Step A2, but the reaction temperature will generally be between −20° C. and 100° C., and preferably 0–40° C. The reaction time for Step A2 will differ depending on the reaction temperature and other reaction conditions, but will usually be from 1 minute to 24 hours, and preferably from 10 minutes to 5 hours.

In FIG. 1, Compound 7 is obtained by reaction between Compound 5 obtained in Step A2 and a compound represented by general formula (5) (Compound 6) in an inert solvent in the presence of a condensation agent (Step A3). When the target compound (the triphenylmethane derivative or triphenylamine derivative represented by general formula (1)) has no side chain functional group, or when the side chain functional group is not protected, or when the protected form is the final target compound, Compound 7 obtained in Step A3 will be the final product.

The compounds of the invention (triphenylmethane derivatives or triphenylamine derivatives represented by general formula (1)) include those with functional groups such as amino, carboxy or hydroxy substituted on the substituent ($R^1$), and for production of such a compound having such a functional group on the substituent ($R^1$), it is preferred to use as the starting compound a compound represented by general formula (5) with the substituent ($R^1$) protected. Using a compound represented by general formula (5) with the substituent ($R^1$) protected will tend to improve the selectivity for the reaction involving the carboxylic acid in general formula (5) in Step A3. As protecting groups for the substituent ($R^1$) there may be specifically mentioned substituted sulfonyl groups such as p-toluenesulfonyl and 2,2,4,6,7-pentamethyl-dihydrobenzofuran-5-sulfonyl groups; optionally substituted alkyl groups such as methyl, methoxymethyl, ethoxyethyl, t-butyl and triphenylmethyl groups; substituted silyl groups such as trimethylsilyl, triethylsilyl, triisopropylsilyl, t-butyldimethylsilyl and t-butyldiphenylsilyl groups; substituted phenyl groups such as p-chlorophenyl, p-methoxyphenyl and 2,4-dinitrophenyl groups; optionally substituted benzyl groups such as benzyl, p-methoxybenzyl, 3,4-dimethoxybenzyl, o-nitrobenzyl, p-nitrobenzyl, p-chlorobenzyl, p-bromobenzyl, 2,6-dichlorobenzyl, 2,6-dimethylbenzyl, p-cyanobenzyl and p-phenylbenzyl groups; alkylcarbonyl groups such as formyl, acetyl, propionyl, butyryl, valeryl, levulinyl and pivaloyl groups; arylcarbonyl groups such as benzoyl, 4-nitrobenzoyl, 4-chlorobenzoyl, 2-iodobenzoyl, 4-methoxybenzoyl, p-phenylbenzoyl, 2,4,6-triphenylbenzoyl, o-(dibromomethyl)benzoyl, 2-(methylthiomethoxymethyl)benzoyl, o-(methoxycarbonyl)benzoyl, naphthoyl, toluoyl and 9-fluorenecarbonyl groups; and oxycarbonyl groups such as methoxycarbonyl, ethoxycarbonyl, t-butoxycarbonyl, benzyloxycarbonyl and 4-methoxybenzyloxycarbonyl groups. These protecting groups may be easily removed from the side chain functional groups by the methods described hereunder.

As condensation agents to be used in Step A3 there may be specifically mentioned O-(7-azabenzotriazol-1-yl)-1,1,3,3-tetramethyluronium hexafluorophosphate, 1-ethyl-3-(3-dimethylaminopropyl) carbodiimide, dicyclohexyl carbodiimide, diisopropyl carbodiimide, benzotriazol-1-yloxy-tris(dimethylamino)phosphonium hexafluorophosphate, diphenylphosphoryl azide and diphenylphosphoryl cyanide, among which O-(7-azabenzotriazol-1-yl)-1,1,3,3-tetramethyluronium hexafluorophosphate and 1-ethyl-3-(3-dimethylaminopropyl) carbodiimide are preferred for use.

The inert solvent to be used in Step A3 is not particularly restricted so long as it does not participate in the reaction, and specifically there may be mentioned hydrocarbons such as hexane, cyclohexane, benzene, toluene and xylene; halogenated hydrocarbons such as methylene chloride, chloroform, 1,2-dichloroethane and tetrachloromethane; ethers such as ether, tetrahydrofuran and dioxane; amides such as N,N-dimethylformamide, N,N-dimethylacetamide, N-methyl-2-pyrrolidone and hexamethylphosphoramide; sulfoxides such as dimethylsulfoxide; and mixed solvents comprising two or more of these. Among such solvents there are preferred halogenated hydrocarbons and/or amides, with N,N-dimethylformamide or mixed solvents of methylene chloride and N,N-dimethylformamide being especially preferred. When a mixed solvent of methylene chloride and N,N-dimethylformamide is used, the mixing ratio (volume ratio) will normally be methylene chloride:N,N-dimethylformamide=1:9–9:1, and preferably methylene chloride:N,N-dimethylformamide=5:5.

In Step A3 there is preferably also used an additive including an organic amine such as N-methylmorpholine or 4-dimethylaminopyridine, or an N-hydroxy derivative such as N-hydroxysuccinimide, 1-hydroxybenzotriazole or 3-hydroxy-4-oxo-3,4-dihydro-1,2,3-benzotriazine. Preferred of such additives are organic amines, among which N-methylmorpholine and 4-dimethylaminopyridine are especially preferred.

There are no particular restrictions on the reaction conditions for Step A3, but the reaction temperature will generally be between −20° C. and 100° C., and preferably 0–40° C. The reaction time for Step A3 will differ depending on the reaction temperature and other reaction conditions, but will usually be from 1 hour to 5 days, and preferably from 3 hours to 3 days.

When an $N^\alpha$-9-fluorenylmethoxycarbonylamino acid derivative with the side chain functional group protected is used in Step A1, and/or a compound represented by general formula (5) with the substituent ($R^1$) protected is used in Step A3, Compound 7 obtained in Step A3 is reacted under appropriate conditions to remove the protecting group and obtain the target Compound 8 (Step A4). When Compound 7 includes two or more different protected functional groups and the reaction conditions suitable for deprotection differ for each protecting group, Step A4 is carried out several times as necessary under the suitable reaction conditions.

When the side chain in Step A1 and/or the substituent ($R^1$) in Step A3 is, for example, amino group protected with t-butoxycarbonyl, triphenylmethyl group or 2,2,4,6,7-pentamethyl-dihydrobenzofuran-5-sulfonyl group, hydroxy group protected with guanidyl, t-butyl or triphenylmethyl group, or carboxylic acid protected as phenol or t-butylester, acid is preferably used as the protecting group in Step A4. As acids to be used in this case there may be mentioned inorganic acids such as hydrochloric acid and sulfuric acid or organic acids such as acetic acid and trifluoroacetic acid, among which trifluoroacetic acid and hydrochloric acid are especially preferred.

When the side chain in Step A1 and/or the substituent ($R^1$) in Step A3 is, for example, an amino group protected with a benzyloxycarbonyl group or a benzyl group, a hydroxy group protected with a benzyl group or carboxylic acid protected as phenol or benzylester, contact reduction in the presence of metal catalyst is preferred for deprotection in Step A4. The metal catalyst to be used in this case is not particularly restricted so long as it is conventionally used for contact reduction reactions, and specifically there may be mentioned palladium-carbon, Raney Nickel, platinum oxide, platinum black, rhodium-aluminum oxide, triphenylphosphine-rhodium chloride and palladiumbarium sulfate, among which palladium-carbon is preferred.

The inert solvent to be used for deprotection with an acid in Step A4 is not particularly restricted so long as it does not participate in the reaction, and specifically there may be mentioned hydrocarbons such as hexane, cyclohexane, benzene, toluene and xylene; halogenated hydrocarbons such as methylene chloride, chloroform, 1,2-dichloroethane and tetrachloromethane; ethers such as ether, tetrahydrofuran and dioxane; alcohols such as methanol, ethanol and isopropanol; sulfoxides such as dimethylsulfoxide; and mixed solvents comprising two or more of these. Alcohols are preferred when hydrochloric acid is used as the acid, with methanol being especially preferred. When trifluoroacetic acid is used as the acid, halogenated hydrocarbons are preferred, with methylene chloride being especially preferred.

There are no particular restrictions on the reaction conditions for deprotection with an acid in Step A4, but the reaction temperature will generally be between −20° C. and 100° C., and preferably 0–40° C. The reaction time for Step A4 will differ depending on the reaction temperature and other reaction conditions, but will usually be from 1 minute to 3 days, and preferably from 1–24 hours.

There are no particular restrictions on the inert solvent used for deprotection by contact reduction in Step A4 so long as it is one which is conventionally used for contact reduction reactions, and specifically there may be mentioned alcohols such as methanol, ethanol, 1-propanol and 2-propanol; ethers such as tetrahydrofuran, dioxane and diethyl ether; hydrocarbons such as benzene, toluene and cyclohexane; amides such as N,N-dimethylformamide and N,N-dimethylacetamide; esters such as methyl acetate and ethyl acetate; acids such as acetic acid and hydrochloric acid; water, or mixed solvents of two or more of these. Preferred of these are alcohols and amides, among which methanol, N,N-dimethylformamide or their mixtures are particularly preferred for use. When a mixed solvent of methanol and N,N-dimethylformamide is used, the mixing ratio (volume ratio) will normally be methanol:N,N-dimethylformamide=1:9–9:1, and preferably methanol:N,N-dimethylformamide=5:5.

There are no particular restrictions on the reaction conditions for deprotection by contact reduction in Step A4, but the hydrogen pressure in the reaction system will generally be 0.1–1.0 MPa (1–10 atmospheres) and preferably 0.1–0.3 MPa (1–3 atmospheres). The reaction temperature in Step A4 will generally be 0–80° C., and preferably 10–40° C. The reaction time for Step A4 will generally be 30 minutes to 7 days, and preferably 6 hours to 3 days.

Figure 2:
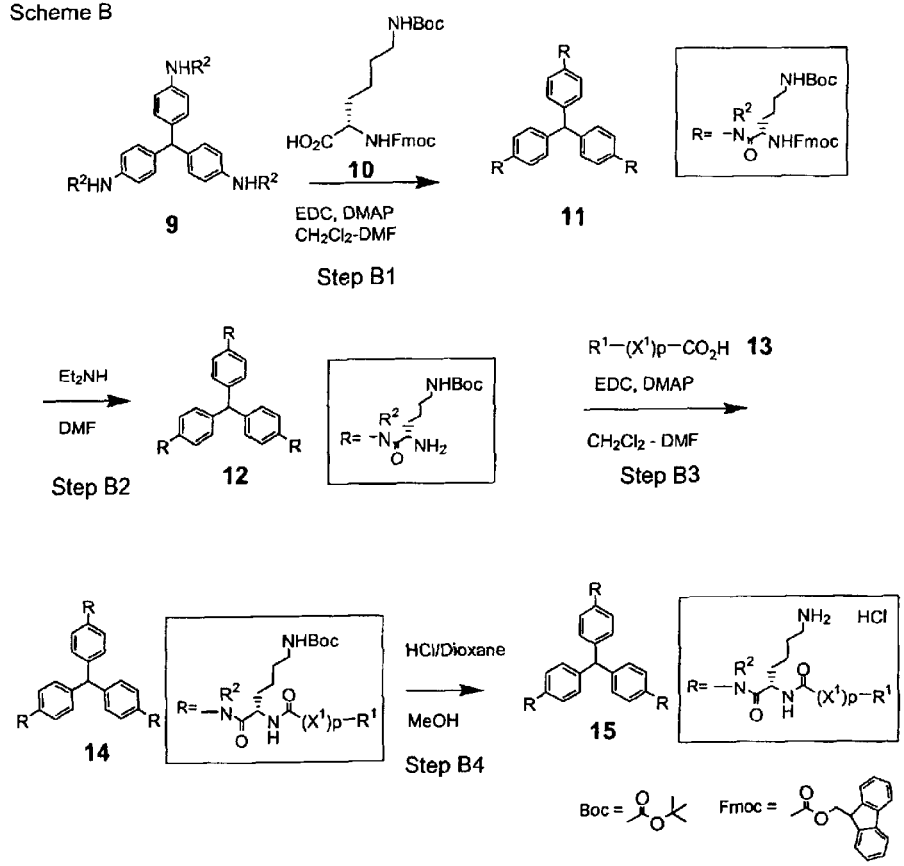
FIG. 2 is a reaction scheme diagram showing another example of the first production process for a compound according to the invention.

FIG. 2 shows a more concrete example of a reaction scheme diagram according to the first production process of the invention, wherein a triphenylmethane derivative 9 is used as the starting material. FIG. 2 differs from the reaction scheme diagram in FIG. 1 only in using EDC as the condensation agent, DMAP as the additive and $CH_2Cl_2$-DMF as the inert solvent for Steps A1 and A3 and using $Et_2NH$ as the organic amine in Step A2, whereby a triphenylmethane derivative (Compound 15) represented by general formula (1) is obtained.

Figure 3:
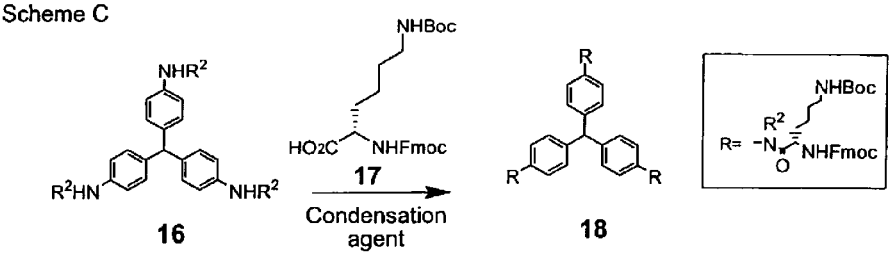
FIG. 3 is a reaction scheme diagram showing another example of the first production process for a compound according to the invention.
Figure 3:
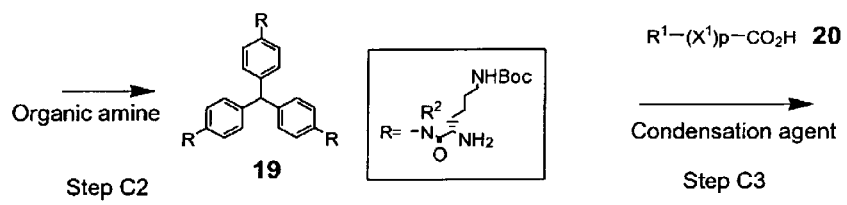
Figure 3:
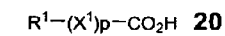
Figure 3:
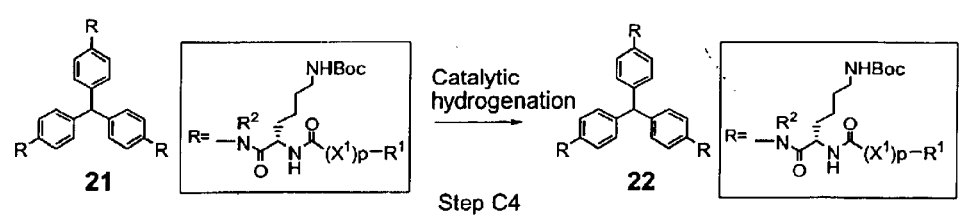
Figure 3:
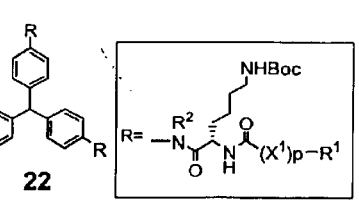
Figure 3:
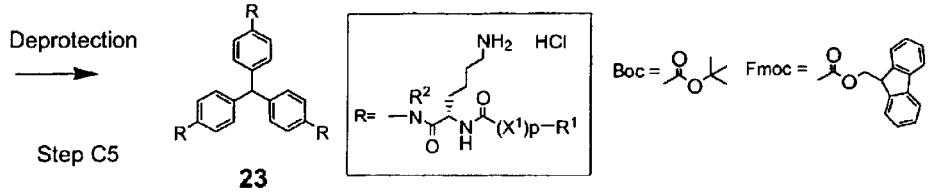

When the group represented by $R^1$ has hydroxyl group as a side chain functional group, the target compound may also be obtained by the process shown in FIG. 3. That is, as shown in FIG. 3, first the $N^{\alpha}$-9-fluorenylmethoxycarbonylamino acid derivative 17 is used in carrying out Steps C1–C3, corresponding to Steps A1–A3, in that order to obtain Compound 21. As protecting groups for the hydroxyl group in the process shown in FIG. 3 there may be specifically mentioned the protecting groups mentioned as examples in the explanation of Step A1.

Compound 21 obtained in this manner is subjected to contact reduction in an inert solvent in the presence of metal catalyst for removal of the protecting group from the hydroxyl group of Compound 21 to obtain Compound 21 (Step C4). The metal catalyst used for Step C4 is not particularly restricted so long as it is conventionally used for contact reduction reactions, and specifically there may be mentioned palladium-carbon, Raney Nickel, platinum oxide, platinum black, rhodium-aluminum oxide, triphenylphosphine-rhodium chloride and palladium-barium sulfate, among which palladium-carbon is preferred.

There are no particular restrictions on the inert solvent used for Step C4 so long as it is one which is conventionally used for contact reduction reactions, and specifically there may be mentioned alcohols such as methanol, ethanol, 1-propanol and 2-propanol; ethers such as tetrahydrofuran, dioxane and diethyl ether; hydrocarbons such as benzene, toluene and cyclohexane; amides such as N,N-dimethylformamide and N,N-dimethylacetamide; esters such as methyl acetate and ethyl acetate; acids such as acetic acid and hydrochloric acid; water, or mixed solvents of two or more of these, among which amides are preferred, and N,N-dimethylformamide is especially preferred.

There are no particular restrictions on the reaction conditions for Step C4, but the hydrogen pressure in the reaction system will generally be 0.1–1.0 MPa (1–10 atmospheres) and preferably 0.1–0.3 MPa (1–3 atmospheres). The reaction temperature in Step C4 will generally be 0–80° C., and preferably 10–40° C. The reaction time for Step C4 will generally be 30 minutes to 3 days, and preferably 6–24 hours.

Compound 22 obtained in Step C4 is further reacted with an acid in an inert solvent to obtain the target Compound 23 (triphenylmethane derivative) (Step C5). As acids and inert solvents to be used in Step C5 there may be mentioned the same acids and inert solvents mentioned as examples in the explanation of Step A3.

Although $N^{\alpha}$-9-fluorenylmethoxycarbonylamino acid derivative (Compound 10 or 17) is used as the starting material in the reaction scheme diagrams shown in FIGS. 1–3, a compound of the invention can also be obtained using $N^{\alpha}$-t-butoxycarbonylamino acid derivative represented by general formula (4).

Figure 4:
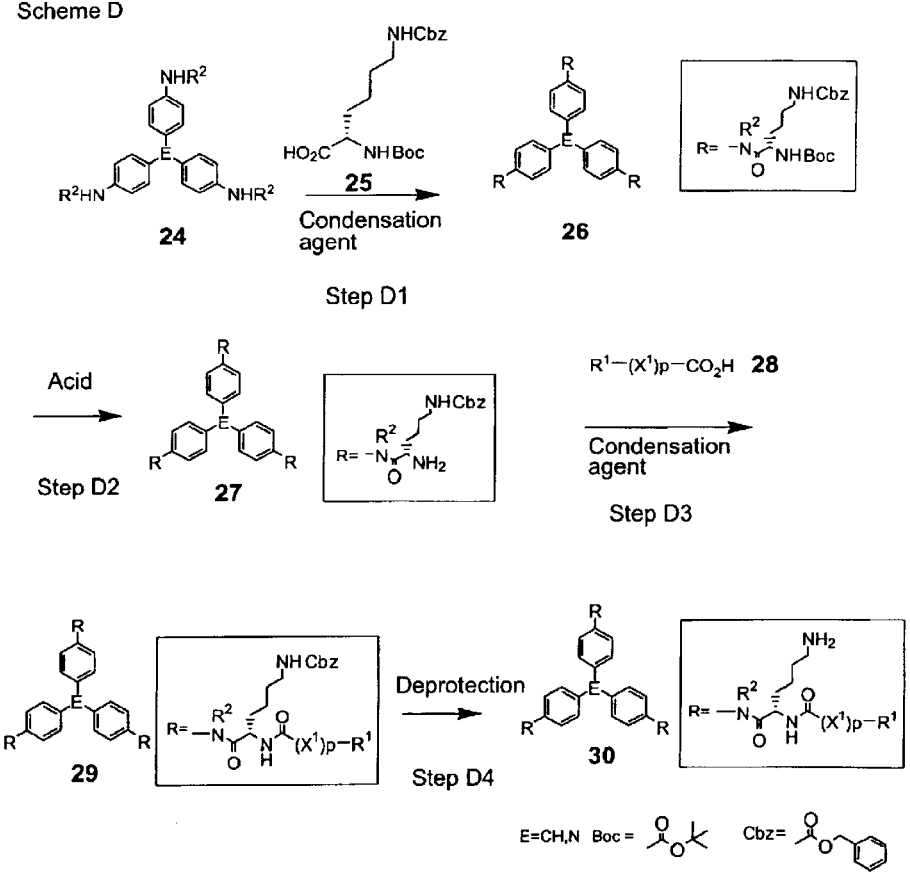
FIG. 4 is a reaction scheme diagram showing another example of the first production process for a compound according to the invention.

FIG. 4 is a reaction scheme diagram showing an example of the first production process according to the invention using $N^{\alpha}$-t-butoxycarbonylamino acid derivative. In FIG. 4, first Compound 24, which is a triphenylmethane derivative or triphenylamine derivative represented by general formula (2), is reacted with Compound 25, which is $N^{\alpha}$-t-butoxycarbonylamino acid derivative represented by general formula (4), in an inert solvent in the presence of condensation agent, to obtain Compound 26 (Step D1).

The compounds of the invention (triphenylmethane derivatives or triphenylamine derivatives represented by general formula (1)) include those with functional groups such as amino group, carboxy group, hydroxy group or thiol group substituted on the side chain of the amino acid residue ($W^1$), and for production of such a triphenylmethane derivative or triphenylamine derivative having a side chain functional group in the amino acid residue, it is preferred to use as the starting compound $N^{\alpha}$-9-t-butoxycarbonylamino acid derivative 25 with the side chain functional group protected. Using $N^{\alpha}$-t-butoxycarbonylamino acid derivative with the side chain functional group protected will tend to improve the selectivity in the reaction involving the α-amino group in the steps described below. As protecting groups for the side chain functional groups there may be specifically mentioned substituted sulfonyl groups such as ptoluenesulfonyl groups; optionally substituted alkyl groups such as methyl, methoxymethyl and ethoxyethyl groups; substituted phenyl groups such as pchlorophenyl, p-methoxyphenyl and 2,4-dinitrophenyl groups; optionally substituted benzyl groups such as benzyl, p-methoxybenzyl, 3,4-dimethoxybenzyl, o-nitrobenzyl, p-nitrobenzyl, p-chlorobenzyl, p-bromobenzyl, 2,6-dichlorobenzyl, 2,6-dimethylbenzyl, p-cyanobenzyl and p-phenylbenzyl; alkylcarbonyl groups such as formyl, acetyl, propionyl, butyryl, valeryl, levulinyl and pivaloyl; arylcarbonyl groups such as benzoyl, 4-nitrobenzoyl, 4-chlorobenzoyl, 2-iodobenzoyl, 4-methoxybenzoyl, p-phenylbenzoyl, 2,4,6-triphenylbenzoyl, o-(dibromomethyl)benzoyl, 2-(methylthiomethoxymethyl)benzoyl, o-(methoxycarbonyl)benzoyl, naphthoyl, toluoyl and 9-fluorenecarbonyl; and oxycarbonyl groups such as methoxycarbonyl, ethoxycarbonyl, benzyloxycarbonyl, 4-methoxybenzyloxycarbonyl and $N^{\alpha}$-9-fluorenylmethoxycarbonyl. These protecting groups may be easily removed from the side chain functional groups by the methods described hereunder.

The preferred condensation agents, solvents and additives for Step D1 are the same as those mentioned in the explanation of Step A1. The preferred reaction conditions for Step D1 are also the conditions described in the explanation of Step A1.

Compound 26 obtained by Step D1 is reacted with an acid in an inert solvent to obtain Compound 27 (Step D2). As acids to be used in Step D2 there may be specifically mentioned inorganic acids such as hydrochloric acid and sulfuric acid and organic acids such as acetic acid and trifluoroacetic acid, among which hydrochloric acid is especially preferred.

There are no particular restrictions on the inert solvent to be used in Step D2 so long as it does not participate in the reaction, and specifically there may be mentioned hydrocarbons such as hexane, cyclohexane, benzene, toluene and xylene; halogenated hydrocarbons such as methylene chloride, chloroform, 1,2-dichloroethane and tetrachloromethane; ethers such as ether, tetrahydrofuran and dioxane; alcohols such as methanol, ethanol and isopropanol; sulfoxides such as dimethylsulfoxide; and mixed solvents comprising two or more of these. Alcohols are preferred among these, with methanol being especially preferred.

There are no particular restrictions on the reaction conditions for Step D2, but the reaction temperature will generally be between −20° C. and 100° C., and preferably 0–40° C. The reaction time for Step D2 will differ depending on the reaction temperature and other reaction conditions, but will usually be from 1 minute to 3 days, and preferably from 1–24 hours.

In FIG. 4, Compound 29 is obtained by reaction between Compound 27 obtained in Step D2 and a compound represented by general formula (5) (Compound 28) in an inert solvent in the presence of a condensation agent (Step D3). When the target triphenylmethane derivative or triphenylamine derivative has no side chain functional group, or when the side chain functional group is not protected, or when the protected form is the final target compound, Compound 29 obtained in Step D3 will be the final product.

The compounds of the invention (triphenylmethane derivatives or triphenylamine derivatives represented by general formula (1)) include those with functional groups such as amino group, carboxy group or hydroxy group substituted on the substituent ($R^1$), and for production of triphenylmethane derivative or triphenylamine derivative having such a functional group on the substituent ($R^1$), it is preferred to use as the starting compound a compound represented by general formula (5) with the substituent ($R^1$) protected. Using a compound represented by general formula (5) with the substituent ($R^1$) protected will tend to improve the selectivity for the reaction involving the carboxylic acid in general formula (5) in Step D3. As protecting groups for the substituent ($R^1$) there may be mentioned the protecting groups mentioned as examples in the explanation of Step A3.

The preferred condensation agents, solvents and additives for Step D3 are the same as those mentioned in the explanation of Step A3. The preferred reaction conditions for Step D3 are also the conditions described in the explanation of Step A3.

When $N^\alpha$-t-butoxycarbonylamino acid derivative with the side chain functional group protected is used in Step D1, and/or when a compound represented by general formula (5) with the substituent ($R^1$) protected is used in Step D3, Compound 29 obtained in Step D3 is reacted under appropriate conditions to remove the protecting group and obtain the target Compound 30 (Step D4). When Compound 29 includes two or more different protected functional groups and the reaction conditions suitable for deprotection differ for each protecting group, Step D4 is carried out several times as necessary under the suitable reaction conditions.

The type of protecting groups in Compound 29 and the reagents, solvents and reaction conditions used for deprotection of the protecting groups are preferably those mentioned in the explanation of Step A4.

Figure 5:
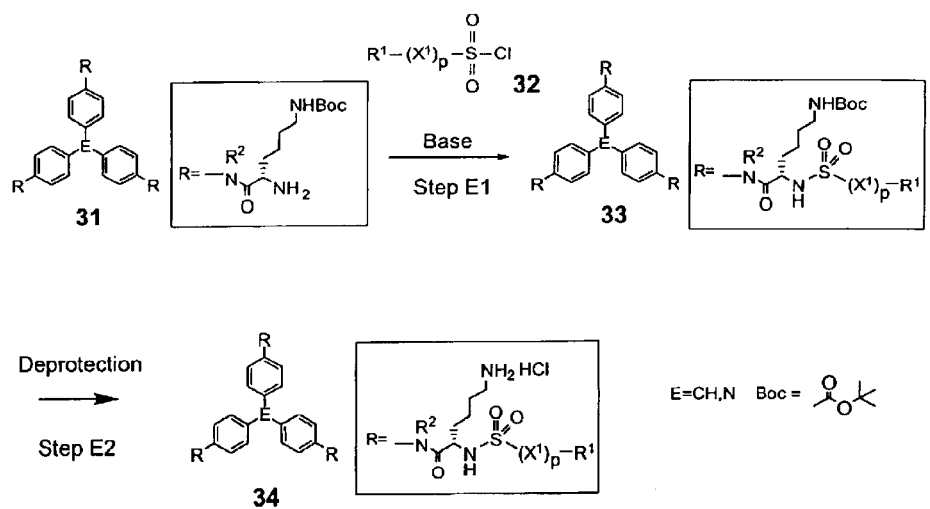
FIG. 5 is a reaction scheme diagram showing another example of the first production process for a compound according to the invention.

FIGS. 1 to 4 show synthesis examples in which each of the resulting compounds has carbonyl group for A in general formula (1), but the synthesis may alternatively be accomplished according to the reaction scheme shown in FIG. 5, for example, in which the resulting compound has a sulfonyl group for A in general formula (1).

In FIG. 5, Compound 31 obtained in the same manner as Compound 5 in FIG. 1 is reacted with Compound 32, having sulfonyl group for A and halogen atom for Z in general formula (5), in an inert solvent in the presence of a base, to obtain Compound 33 (Step E1).

In Step E1, a compound obtained in the same manner as Compound 27 in FIG. 4 may be used instead of Compound 31. When the target triphenylmethane derivative or triphenylamine derivative has no functional group on the amino acid side chain or substituent ($R^1$), or when the amino acid side chain or substituent ($R^1$) is not protected, or when the protected form is the final target compound, Compound 33 obtained in Step E1 will be the final product (the triphenylmethane derivative or triphenylamine derivative of the invention).

As bases to be used for Step E1 there are preferably used organic amines such as triethylamine, diisopropylethylamine, N-methylmorpholine (NMM) and 4-dimethylaminopyridine (DMAP); or inorganic bases such as potassium carbonate, sodium carbonate and cesium carbonate. Among these bases, organic amines are preferred, with N-methylmorpholine (NMM) being especially preferred.

There are no particular restrictions on the inert solvent used in Step E1 so long as it does not participate in the reaction, and specifically there may be mentioned hydrocarbons such as hexane, cyclohexane, benzene, toluene and xylene; halogenated hydrocarbons such as methylene chloride ($CH_2Cl_2$), chloroform, 1,2-dichlorethane and tetrachloromethane; ethers such as ether, tetrahydrofuran and dioxane; amides such as N,N-dimethylformamide (DMF), N,N-dimethylacetamide, N-methyl-2-pyrrolidone and hexamethylphosphoramide; sulfoxides such as dimethylsulfoxide; and mixed solvents comprising two or more of these. Among such solvents there are preferred halogenated hydrocarbons and/or amides, with N,N-dimethylformamide being especially preferred.

There are no particular restrictions on the reaction conditions for Step E1, but the reaction temperature will generally be between −20° C. and 100° C., and preferably 0–40° C. The reaction time for Step E1 will differ depending on the reaction temperature and other reaction conditions, but will usually be from 1 hour to 1 week, and preferably from 3 hours to 5 days.

When a starting material having the amino acid side chain functional group protected (Compound 31) and/or a compound represented by general formula (5) with the substituent ($R^1$) protected (Compound 32) is used in Step E1, the compound obtained in Step E1 (Compound 33) is reacted under appropriate conditions to remove the protecting group and obtain the target compound (Compound 34) (Step E2). When Compound 33 obtained in Step E1 includes two or more different protected functional groups and the reaction conditions suitable for deprotection differ for each protecting group, Step E2 is carried out several times as necessary under the suitable reaction conditions.

The type of protecting groups in Compound 33 obtained in Step E1 and the reagents, solvents and reaction conditions used for deprotection of the protecting groups are preferably those mentioned in the explanation of Step A4.

The compounds of the invention (triphenylmethane derivatives or triphenylamine derivatives represented by general formula (1)) may also be obtained by the second production process described below. The second production process for triphenylmethane derivatives according to the invention comprises a fourth step of reacting an amino acid derivative and a silylating agent;

a fifth step of reacting the compound obtained in the fourth step with a compound represented by the following general formula (5):

$$R^1—(X^1)_p—A—Z \qquad (5)$$

wherein $R^1$ represents one selected from the group consisting of hydrogen atom, hydroxy group, carboxy group, optionally substituted amino group, optionally substituted aryl group and optionally substituted heterocylic group, $X^1$ represents one selected from the group consisting of optionally substituted alkylene group and optionally substituted alkenylene group, p represents 0 or 1, A represents one selected from the group consisting of carbonyl group and sulfonyl group, and Z represents one selected from the group consisting of hydroxy group and halogen group; and a sixth step of reacting the compound obtained in the fifth step with a compound represented by the following general formula (2):

wherein E represents one selected from the group consisting of methylidyne group and nitrilo group and $R^2$ represents one selected from the group consisting of hydrogen atom and alkyl group,
in the presence of condensation agent, to obtain a compound represented by the following formula (1):

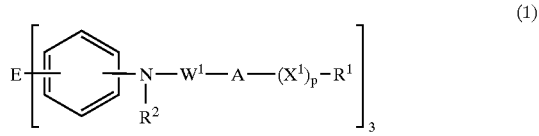

wherein E represents one selected from the group consisting of a methylidyne group and a nitrilo group, $R^1$ represents one selected from the group consisting of a hydrogen atom, a hydroxy group, a carboxy group, optionally substituted amino groups, optionally substituted aryl groups and optionally substituted heterocyclic group, $R^2$ represents one selected from the group consisting of a hydrogen atom and alkyl groups, $W^1$ represents an amino acid residue, A represents one selected from the group consisting of a carbonyl group and a sulfonyl group, $X^1$ represents one selected from the group consisting of optionally substituted alkylene group and optionally substituted alkenylene groups, and p represents 0 or 1.

Figure 6:
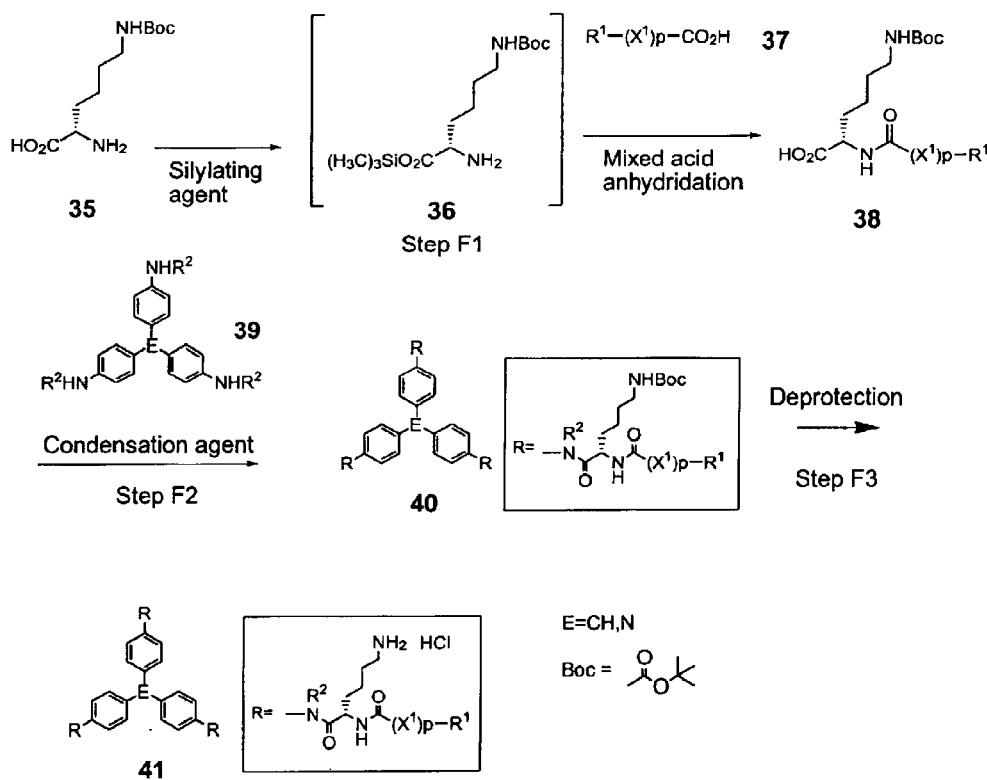
FIG. 6 is a reaction scheme diagram showing an example of the second production process for a compound according to the invention.

In FIG. 6, Compound 35 as an amino acid derivative is first reacted with a silylating agent $(CH_2=C[OSi(CH_3)_3][NHSi(CH_3)_3]$, etc.) in an inert solvent to obtain an intermediate 36, and then the intermediate 36 is reacted with a compound represented by general formula (5) (Compound 37) by the mixed acid anhydride method to obtain Compound 38 (Step F1). When the target triphenyl-methane derivative or triphenylamine derivative is to have a functional group such as amino group, carboxy group, hydroxy group or thiol group on the amino acid residue side chain, the amino acid derivative used preferably has its side chain functional group protected. Using an amino acid derivative with the side chain functional group protected will tend to improve the selectivity in the reaction involving the α-amino group in the steps described below. As protecting groups for the side chain functional group there may be mentioned the protecting groups mentioned as examples in the explanation of Step A1.

As silylating agents to be used in Step F1 there may be specifically mentioned N,O-bis(trimethylsilyl)acetamide, N,O-bis(trimethylsilyl)trifluoroacetamide, N-methyl-N-trimethylsilylacetamide, N,O-bis(trimethylsilyl) carbamate, N,N-dimethyl-O-trimethylsilyl carbamate, N,O-bis(trimethylsilyl) sulfamate, allyltrimethylsilane, trimethylsilylsulfonic acid, N,N'-bistrimethylsilylurea, trimethylsilylethyl thioether, isopropenyloxytrimethylsilane, methyl 3-trimethylsiloxy-2-butenoate, trimethylsilyl cyanide, trimethylsilyl chloride, trimethylsilyl bromide, trimethylsilyl iodide, trimethylsilylimidazole, trimethylsilyl trichloroacetate, trimethylsilyl trifluoromethanesulfonate, triethylsilyl chloride, triisopropylsilyl chloride, t-butyldiphenylsilyl chloride and t-butyldiphenylsilyltrifluoromethane sulfonate, among which N,O-bis(trimethylsilyl)acetamide, N,O-bis(trimethylsilyl)trifluoroacetamide, N-methyl-N-trimethylsilylacetamide, N,O-bis(trimethylsilyl) carbamate, N,N-dimethyl-O-trimethylsilyl carbamate and N,O-bis(trimethylsilyl) sulfamate are preferred, and N,O-bis(trimethylsilyl)acetamide is particularly preferred. In Step F1 there are also preferably added, in addition to the aforementioned silylating agents, also organic acids such as tosylic acid and pyridinium tosylate; organic bases such as triethylamine, diisopropylethylamine, N-methylmorpholine, pyridine, imidazole and 2,6-lutidine, and/or inorganic bases such as potassium carbonate, sodium carbonate and sodium hydride. Using such acids or bases will tend to increase the yield of the reaction in Step F1.

As mixed acid anhydride reagents to be used in Step F1 there may be mentioned alkyloxycarbonyl chlorides such as methoxycarbonyl chloride, ethoxycarbonyl chloride, 1-chloroethyloxycarbonyl chloride, 2-chloroethyloxycarbonyl chloride, 2,2,2-trichloroethyloxycarbonyl chloride, 2-methoxyethyloxycarbonyl chloride, n-propyloxycarbonyl chloride, isopropyloxycarbonyl chloride, allyloxycarbonyl chloride, n-butyloxycarbonyl chloride, isobutyloxycarbonyl chloride, n-amyloxycarbonyl chloride, n-hexyloxycarbonyl chloride, 2-ethylhexyloxycarbonyl chloride, n-heptyloxycarbonyl chloride, n-octyloxycarbonyl chloride, n-nonyloxycarbonyl chloride, n-decyloxycarbonyl chloride, n-hexadecyloxycarbonyl chloride, benzyloxycarbonyl chloride, 4-nitrobenzyloxycarbonyl chloride, phenyloxycarbonyl chloride, 4-nitrophenyloxycarbonyl chloride and 2-naphthyloxycarbonyl chloride; and alkylacetyl chlorides such as acetyl chloride, diethylacetyl chloride and trimethylacetyl chloride, among which ethoxycarbonyl chloride, n-propyloxycarbonyl chloride, isopropyloxycarbonyl chloride, n-butyloxycarbonyl chloride and isobutyloxycarbonyl chloride are preferred for use, with isobutyloxycarbonyl chloride being especially preferred.

As bases to be used for Step F1 there may be mentioned organic amines such as triethylamine, diisopropylethylamine, N-methylmorpholine, pyridine, 4-dimethylaminopyridine, imidazole and 2,6-lutidine, alkali metal bicarbonates such as sodium bicarbonate and potassium bicarbonate, and alkali metal carbonates such as sodium carbonate and potassium carbonate, among which organic amines are preferred for use, and N-methylmorpholine is particularly preferred.

There are no particular restrictions on the solvent to be used in Step F1 so long as it does not participate in the reaction, and specifically there may be mentioned hydrocarbons such as hexane, cyclohexane, benzene, toluene and xylene; halogenated hydrocarbons such as methylene chloride, chloroform, 1,2-dichlorethane and tetrachloromethane; ethers such as ether, tetrahydrofuran and dioxane; amides such as N,N-dimethylformamide, N,N-dimethylacetamide, N-methyl-2-pyrrolidone and hexamethylphosphoramide; sulfoxides such as dimethylsulfoxide; and mixed solvents comprising two or more of these. Among such solvents there are preferred halogenated hydrocarbons or amides, with methylene chloride, N,N-dimethylacetamide or mixed solvents thereof being especially preferred. When a mixed solvent of methylene chloride and N,N-dimethylformamide is used, the mixing ratio (volume ratio) will normally be methylene chloride:N,N-dimethylformamide=1:9–9:1, and preferably methylene chloride:N,N-dimethylformamide=2:1.

There are no particular restrictions on the reaction conditions for Step F1, but the reaction temperature will generally be between −40° C. and 60° C., and preferably between −20 and 40° C. The reaction time for Step F1 will differ depending on the reaction temperature and other reaction conditions, but will usually be from 30 minutes to 24 hours, and preferably from 1–6 hours.

Compound 38, which is obtained in Step F1 is then reacted with Compound 39, which is a triphenylmethane derivative or triphenylamine derivative represented by general formula (2), in an inert solvent in the presence of a condensation agent, to obtain Compound 40 (Step F2). When the amino acid derivative used in Step F1 has no side chain functional group, or when the side chain functional group is not protected, or when the protected form is the final target compound, Compound 40 obtained in Step F2 will be the final product.

As condensation agents to be used in Step F2 there may be specifically mentioned 1-ethyl-3-(3-dimethylaminopropyl) carbodiimide hydrochloride, dicyclohexyl carbodiimide, diisopropyl carbodiimide, benzotriazol-1-yloxy-tris(dimethylamino)phosphonium hexafluorophosphate, O-(7-azabenzotriazol-1-yl)-1,1,3,3-tetramethyluronium hexafluorophosphate, diphenylphosphoryl azide and diphenylphosphoryl cyanide, among which O-(7-azabenzotriazol-1-yl)-1,1,3,3-tetramethyluronium hexafluorophosphate and 1-ethyl-3(3-dimethylaminopropyl)carbodiimide hydrochloride are preferred.

There are no particular restrictions on the inert solvent to be used in Step F2 so long as it does not participate in the reaction, and specifically there may be mentioned hydrocarbons such as hexane, cyclohexane, benzene, toluene and xylene; halogenated hydrocarbons such as methylene chloride, chloroform, 1,2-dichlorethane and tetrachloromethane; ethers such as ether, tetrahydrofuran and dioxane; amides such as N,N-dimethylformamide, N,N-dimethylacetamide, N-methyl-2-pyrrolidone and hexamethylphosphoramide; sulfoxides such as dimethylsulfoxide; and mixed solvents comprising two or more of these. Among such solvents there are preferred halogenated hydrocarbons or amides, N,N-dimethylformamide being especially preferred.

In Step F2 there are preferably also used additives including organic amines such as 4-dimethylaminopyridine and N-methylmorpholine, or N-hydroxy derivatives such as N-hydroxysuccinimide, 1-hydroxybenzotriazole and 3-hydroxy-4-oxo-3,4-dihydro-1,2,3-benzotriazine. Using such additives will tend to increase the reaction yield in Step F2, and among such additives there are particularly preferred N-methylmorpholine and 1-hydroxybenzotriazole.

There are no particular restrictions on the reaction conditions for Step F2, but the reaction temperature will generally be between −20° C. and 100° C., and preferably 0–40° C. The reaction time for Step F2 will differ depending on the reaction temperature and other reaction conditions, but will usually be from 1 hour to 5 days, and preferably from 12 hours to 3 days.

When an amino acid derivative with the side chain functional group protected is used and/or a compound represented by general formula (5) with the substituent ($R^1$) protected is used in Step F1, Compound 40 obtained in Step F2 is reacted under appropriate conditions to remove the protecting group and obtain the target Compound 41 (Step F3). When Compound 40 includes two or more different protected functional groups and the reaction conditions suitable for deprotection differ for each protecting group, Step F3 is carried out several times as necessary under the suitable reaction conditions.

The types of protecting groups in Compound 40 and the reagents, solvents and reaction conditions used for deprotection are preferably those mentioned as examples in the explanation of Step A4.

Figure 7:
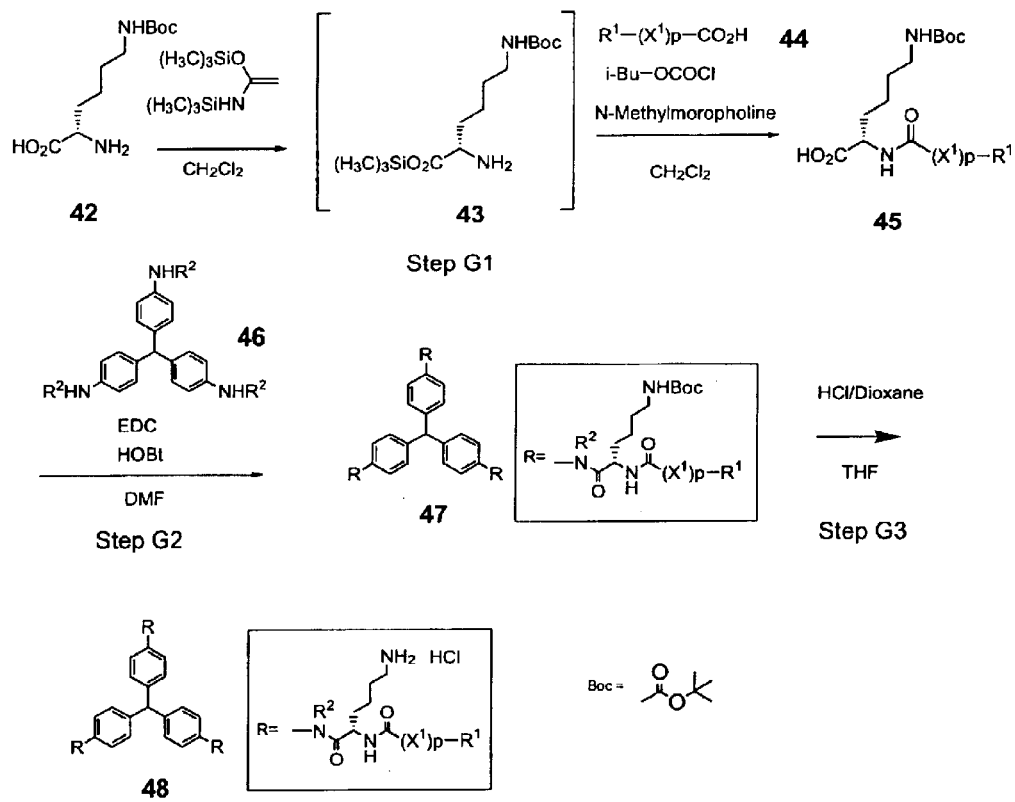
FIG. 7 is a reaction scheme diagram showing another example of the second production process for a compound according to the invention.

FIG. 7 shows a more concrete example of the second production process of the invention, illustrating a reaction scheme diagram wherein in Step G2, a triphenylmethane derivative 46 is used as the compound represented by general formula (2) to obtain a triphenylmethane derivative 48 represented by general formula (1).

For this production process, the produced target compound is separated and collected from the reaction mixture by ordinary processes. For example, when the target compound is obtained as precipitated crystals or when impurities are present in the reaction mixture, these may be separated by appropriate filtration. When the reaction mixture is acidic or alkaline, the target compound may be obtained by appropriate neutralization, addition of water, extraction with a water-immiscible organic solvent such as ethyl acetate, drying, and distilling off of the extraction solvent. If necessary, it may be purified by methods such as recrystallization, column chromatography, preparative high performance liquid chromatography or the like.

The starting material Compounds 2, 9 16, 24, 39 and 46 used in the above-mentioned production processes wherein $R^2$ is hydrogen and E is methylidyne are available as commercial products (by Nacalai Tesque Inc., for example).

The starting material Compounds 2, 24 and 39 used in the above-mentioned production processes wherein E is nitrilo are preferably obtained by metal reduction of commercially available tris(4-nitrophenyl)amine (by Aldrich Co., Ltd., for example). There are no particular restrictions on the metal used for the metal reduction so long as it is one which has conventionally been used for reduction, and as specific metals there may be mentioned zinc, iron, tin and their halides, among which tin dichloride is preferred.

There are no particular restrictions on the solvent to be used for reduction with the aforementioned metal so long as it does not participate in the reaction, and there may be mentioned inorganic or organic acids such as hydrochloric acid or acetic acid; ethers such as ether, tetrahydrofuran and dioxane; alcohols such as methanol, ethanol and isopropanol; and amides such as N,N-dimethylformamide, N,N-dimethylacetamide, N-methyl-2-pyrrolidone and hexamethylphosphoramide. Hydrochloric acid is particularly preferred among these.

There are no particular restrictions on the reaction conditions for reduction with the metal, but the reaction temperature will generally be between room temperature and 150° C., and preferably 100° C. The reaction time will differ depending on the reaction temperature and other reaction conditions, but will usually be from 1 hour to 1 week, and preferably from 5 hours to 3 days.

The starting material Compounds 2, 9 16, 24, 39 and 46 used in the above-mentioned production processes wherein $R^2$ is alkyl may be produced according to methods publicly known in the prior art (for example, the method described in Japanese Unexamined Patent Publication SHO No. 64-54).

The starting material Compounds 3, 10, 17, 25, 35 and 42 used in the above-mentioned production processes may be commercially available products (for example, by Wako Pure Chemical Industries, Ltd., Nacalai Tesque, Inc. or Watanabe Chemical Industries, Ltd.).

The starting material Compounds 6, 13, 20, 28, 37 and 44 used in the above-mentioned production processes may be commercially available products (for example, by Sigma Co., Tokyo Kasei Kogyo Co., Ltd., Nacalai Tesque, Inc., Kanto Kagaku Co., Ltd., Aldrich Co., Ltd. or Lancaster Co., Ltd.), or they may be produced according to methods publicly known in the prior art. The starting material Compounds 6, 13, 20, 28, 37 and 44 which are substituted indoleacetic acid derivatives may be produced according to methods publicly known in the prior art (for example, the methods described in J. Med. Chem., 7, 313(1964); J. Med. Chem., 11, 1252(1968); J. Org. Chem., 62, 2676(1997) and elsewhere).

The starting material Compound 32 used for the above-mentioned production process may be a commercially available product (for example, by Kanto Kagaku Co., Ltd. or Aldrich Co., Ltd.), or it may be produced according to a method publicly known in the prior art.

Although FIGS. 1 to 7 illustrate methods for production of triphenylmethane derivatives and triphenylamine derivatives wherein $W^1$ in general formula (1) is a lysine residue, it is possible to use, in place of any of the Compounds 3, 10 or 17, an $N^\alpha$-9-fluorenylmethoxycarbonylamino acid such as Fmoc-alanine, Fmoc-β-alanine, Fmoc-β-2-pyridyl-alanine, $N^\alpha$-Fmoc-asparagine, $N^\alpha$-Fmoc-N-$^\beta$-Boc-lysine, Fmoc-S-t-butylcysteine, Fmoc-S-trityl-cysteine, Fmoc-S-t-butoxycarbonylaminopropyl-cysteine, Fmoc-serine, Fmoc-O-t-butyl-serine, Fmoc-threonine, Fmoc-O-t-butyl-threonine, Fmoc-O-t-butyl-tyrosine, Fmoc-O-benzyl-tyrosine, Fmoc-aspartic β-t-butyl ester, Fmoc-glutamic γ-t-butyl ester, $N^\alpha$-Fmoc-glutamine, Fmoc-glycine, Fmoc-isoleucine, Fmoc-leucine, Fmoc-methionine, Fmoc-S-dioxo-methionine, $N^\alpha$-Fmoc-$N^\tau$-dimethyl-lysine, $N^\alpha$-Fmoc-$N^\omega$-(2,2,4,6,7-pentamethyl-dihydrobenzofuran-5-sulfonyl)-arginine, $N^\alpha$-Fmoc-$N^\omega$-nitroarginine, Fmoc-phenylalanine, Fmoc-4-nitrophenylalanine, Fmoc-proline, Fmoc-hydroxyproline, $N^\alpha$-Fmoc-citrulline, $N^\alpha$-Fmoc-$N^{im}$-trityl-histidine, $N^\alpha$-Fmoc-$N^{im}$-benzyloxymethyl-histidine, $N^\alpha$-Fmoc-$N^\gamma$-Cbz-ornithine, Fmoc-tryptophan or Fmoc-valine, either as one of the enantiomers or as a mixture thereof;

in place of Compound 25, a $N^\alpha$-t-butoxycarbonylcarbonylamino acid such as Boc-alanine, Boc-β-alanine, Boc-β-2-pyridyl-alanine, $N^\alpha$-Boc-asparagine, Boc-serine, Boc-O-benzyl-serine, Boc-threonine, Boc-O-benzyl-tyrosine, $N^\alpha$-Boc-glutamine, Boc-glycine, Boc-isoleucine, Boc-leucine, Boc-methionine, Boc-S-dioxo-methionine, $N^\alpha$-Boc-$N^\omega$-nitroarginine, Boc-phenylalanine, Boc-4-nitrophenylalanine, Boc-proline, Boc-hydroxyproline, $N^\alpha$-Boc-citrulline, $N^\alpha$-Boc-$N^\epsilon$-dimethyl-lysine, $N^\alpha$-Boc-$N^{im}$-benzyloxymethyl-histidine, $N^\alpha$-Boc-$N^\gamma$-Cbz-ornithine, Boc-tryptophan or Boc-valine, either as one of the enantiomers or a mixture thereof; and in place of Compound 35 or 42, L-alanine-asparagine, $N^\epsilon$-Boc-lysine, $N^\epsilon$-dimethyl-lysine, S-t-butyl-cysteine, S-trityl-cysteine, O-t-butyl-serine, O-t-butyl-threonine, O-t-butyl-tyrosine, aspartic acid, β-t-butylester, glutamic acid, γ-t-butylester, $N^\omega$-(2,2,4,6,7-pentamethyl-dihydrobenzofuran-5-sulfonyl)-L-arginine, glycine-isoleucine-leucine-methionine, $N^\omega$-(4-methoxy-2,3,6-trimethylbenzenesulfonyl)arginine-phenylalanine or $N^{im}$-trityl-histidine-tryptophan-valine, either as one of the enantiomers or a mixture thereof, any of which amino acid derivatives may be appropriately selected depending on the structure of the intended triphenylmethane or triphenylamine.

The triphenylmethane and triphenylamine derivatives of the invention, which can be produced in a simple and inexpensive manner by the production process of the invention in the manner described above, exhibit excellent thrombopoietic effects while having acceptably low antigenicity, and are therefore highly suitable as active ingredients of pharmaceutical compositions.

The compounds of the invention, which can be produced in a simple and inexpensive manner by the production process of the invention in the manner described above, exhibit excellent thrombopoietic effects while having acceptably low antigenicity, and are therefore highly suitable as active ingredients of pharmaceutical compositions.

A pharmaceutical composition comprising a compound of the invention may be administered by an oral route (internal administration, absorption, etc.) or parenteral route (intravenous injection, subcutaneous injection, percutaneous injection, etc.), and a solid or liquid formulation may be appropriately prepared in the form of capsules, granules, cream, powder, syrup, tablets, injection or ointment, depending on the route of administration. Conventionally known added components may be used for formulation, such as stabilizers, lubricants, buffering agents, bases, correctives, binders, coating agents, coloring agents, isotonizing agents, excipients, dispersing agents, disintegrating agents, preservatives, solubilizing aids, fluidizers, and the like.

For a pharmaceutical composition according to the invention there may be specifically mentioned as stabilizers, sulfurous acid salts such as sodium bisulfite and sodium sulfite, edetic acid salts such as sodium edetate and tetrasodium edetate, hydrogenated oils, sesame oil, sodium chondroitin sulfate, dibutylhydroxytoluene, adipic acid, ascorbic acid, L-ascorbic stearic acid esters, sodium L-ascorbate, L-aspartic acid, sodium L-aspartate, acetyltryptophan sodium, acetanilide, aprotinin solution, aminoethylsulfonic acid, aminoacetic acid, DL-alanine, L-alanine, and the like;

as lubricants, gum arabic powder, cacao butter, carnauba wax, carmellose calcium, carmellose sodium, caropeptide, hydrous silicon dioxide, hydrous amorphous silicon oxide, dried aluminum hydroxide gel, glycerin, magnesium silicate, light silicic anhydride, light liquid paraffin, crystalline cellulose, hydrogenated oil, synthetic aluminum silicate, sesame oil, wheat starch, white beeswax, talc, macrogols, phosphoric acid, and the like;

as buffering agents, aminoacetic acid, L-arginine, benzoic acid, sodium benzoate, ammonium chloride, potassium chloride, sodium chloride, dried sodium sulfite, dried sodium carbonate, dilute hydrochloric acid, citric acid, calcium citrate, sodium citrate, disodium citrate, calcium gluconate, L-glutamic acid, L-sodium glutamate, creatinine, chlorobutanol, crystalline sodium dihydrogen phosphate, disodium succinate, acetic acid, potassium acetate, sodium acetate, tartaric acid, sodium bicarbonate, sodium carbonate, triethanolamine, lactic acid, sodium lactate solution, glacial acetic acid, boric acid, maleic acid, citric anhydride, anhydrous sodium citrate, anhydrous sodium acetate, anhydrous sodium carbonate, anhydrous sodium monohydrogen phosphate, anhydrous trisodium phosphate, anhydrous sodium dihydrogen phosphate, dlmalic acid, phosphoric acid, trisodium phosphate, sodium hydrogen phosphate, dipotassium phosphate, potassium dihydrogen phosphate, sodium dihydrogen phosphate, sodium dihydrogen phosphate monohydrate, and the like;

as bases, glycerin, vegetable oils (olive oil, sesame oil, wheat germ oil, etc.), stearyl alcohol, cetanol, lard, white vaseline, paraffin, bentonite, lanolin fatty isopropyl, vaseline, polysorbates, macrogols, lauryl alcohol, sodium lauryl sulfate, ethyl linoleate, sodium hydrogen phosphate, rosin, and the like;

as correctives, ascorbic acid, L-aspartic acid, sodium L-aspartate, magnesium L-aspartate, aspartame, amacha, amacha extract, amacha powder, aminoethylsulfonic acid, aminoacetic acid, DL-alanine, sodium saccharate, sugars (lactose, saccharose, glucose, D-mannitol, etc.), dl-menthol, 1-menthols, and the like;

as binders, agar, stearyl alcohol, gelatin, cellulose and its derivatives (ethyl cellulose, carboxymethylethyl cellulose, hydroxypropyl cellulose, hydroxypropylmethyl celluloses, etc.), starches and its derivatives (gelatinized starch, oxidized starch, dextrin, etc.), sugars (lactose, saccharose, microcrystalline cellulose, glucose, etc.), tragacanth, polyvinyl alcohol, and the like;

as antioxidants, ascorbic acid, L-ascorbic stearic acid esters, sulfurous acid esters (sodium sulfite, sodium bisulfite, sodium pyrosulfite, etc.), sodium edetate, erythorbic acid, cysteine hydrochloride, dibutylhydroxytoluene, sodium thiomalate, mixed tocopherol concentrate, butylhydroxyanisole, propyl gallate, and the like;

as coating agents, shellac, cellulose derivatives (cellulose acetate, hydroxypropylcellulose, cellulose acetate phthalate, hydroxypropylmethyl cellulose, etc.), polyvinyl pyrrolidones, polyethylene glycol, macrogols, methacrylic acid copolymers, liquid paraffin, and the like;

as coloring agents, indigocarmine, caramel, riboflavin, and the like;

as isotonizing agents, potassium chloride, sodium chloride, glycerin, sodium bromide, D-sorbitol, nicotinamide, glucose, boric acid, and the like;

as excipients, silicates (synthetic aluminum silicate, magnesium silicate aluminate, calcium silicate, magnesium silicate, etc.), tartaric acid, potassium hydrogen tartrate, magnesium hydroxide, cellulose and its derivatives (hydroxypropyl cellulose, hydroxypropylmethyl cellulose, methyl cellulose, etc.), starch and its derivatives (carboxymethyl starch sodium, β-cyclodextrin, dextrin, hydroxypropyl starch, etc.), sugars (lactose, saccharose, glucose, D-mannitol, etc.), glycerin monostearate, sorbitan monostearate, and the like;

as dispersing agents, gum arabic, propyleneglycol alginate ester, stearic acid and its salts (zinc stearate, magnesium stearate, etc.), sorbitan sesquioleate, D-sorbitol, tragacanth, methyl cellulose, aluminum monostearate, aminoalkyl methacrylate copolymer RS, lactose, glycerin concentrate, propylene glycol, macrogols, sodium lauryl sulfate, and the like;

as disintegrating agents, agar, gelatin, cellulose and its derivatives (crystalline cellulose, cellulose acetate phthalate, hydroxypropyl cellulose, hydroxypropylmethyl cellulose, etc.), carbonates (calcium carbonate, sodium bicarbonate, magnesium carbonate, etc.), starch and its derivatives (carboxymethyl starch sodium, hydroxypropyl starch, etc.), tragacanth, adipic acid, alginic acid, sodium alginate, gelatinized starch, carboxymethyl starch sodium, carmellose, and the like;

as preservatives, alcohols (chlorobutanol, phenethyl alcohol, propylene glycol, benzyl alcohol, etc.), benzalkonium chloride, benzethonium chloride, dried sodium sulfite, dried sodium sulfate, cresol, chlorocresol, dibutylhydroxytoluene, potassium sorbate, sodium dehydroacetate, paraoxybenzoic acid esters (isobutyl paraoxybenzoate, ethyl paraoxybenzoate, methyl paraoxybenzoate, etc.), phenol, formalin, phosphoric acid, benzoin, thimerosal, thymol, sodium dehydroacetate, and the like;

as solubilizing aids, sodium benzoate, ethylenediamine, citric acid, sodium citrate, glycerin, sodium acetate, sodium salicylate, sorbitan sesquioleate, nicotinamide, glucose, benzyl alcohol, polyvinylpyrrolidones, acetone, ethanol, isopropanol, D-sorbitol, sodium bicarbonate, sodium carbonate, lactose, urea, saccharose, and the like;

and as fluidizing agents, hydrous silicon dioxide, stearic acid and its salts (calcium stearate, magnesium stearate, etc.), talc, absolute ethanol, crystalline cellulose, synthetic aluminum silicate, calcium hydrogen phosphate, and the like. Pharmaceutical components other than these additives may also be added.

The amount of a compound of the invention to be included in a pharmaceutical composition according to the invention will depend on the form in which it is prepared, but it is preferably 0.00001–100 wt % based on the total pharmaceutical composition. The dosage of a pharmaceutical composition according to the invention may vary within a wide range according to the species to which it is administered (such as a human or other warm-blooded animal), the severity of symptoms, the physicians's diagnosis, etc., but for oral administration the dosage of the compound of the invention as the active ingredient may preferably be 0.1–2000 mg/kg per day, while for parenteral administration it is preferably 0.1–1000 mg/kg per day. Here, the dosage refers to the value per unit weight of the recipient. According to the invention, the indicated dosage may be administered all at once or over several times, during a period of 1–7 days, depending on the severity of symptoms, the physician's diagnosis, etc.

The pharmaceutical compositions of the invention having the construction described above have excellent thrombopoietic action and acceptably low antigenicity, and can be obtained in a simple and inexpensive manner by the methods described above; they are therefore particularly useful when applied for medical purposes, for example, as thrombopoietic agents or thrombocytopenia treatment agents.

EXAMPLES

The present invention will now be explained in concrete detail based on examples, reference examples and a test example, with the understanding that these examples are in no way limitative on the invention.

In the examples, each of the compounds of the invention was synthesized using one of the compounds obtained in Reference Examples 1–97.

Reference Example 1

Synthesis of tris[4-[N-α-(9-fluorenylmethoxycarbonyl)-N-ε-t-butoxycarbonyl-L-lysyl]aminophenyl]methane Tris(4-aminophenyl)methane (1.85 g), N-α-(9-fluorenylmethoxycarbonyl)-N-ε-t-butoxycarbonyl-L-lysine (15.0 g) and 4-dimethylaminopyridine (78.2 mg) were dissolved in a mixed solvent of dichloromethane (50 ml) and N,N-dimethylformamide (50 ml), after which 1-ethyl3-(3-dimethylaminopropyl)carbodiimide hydrochloride (6.14 g) was added under a nitrogen atmosphere at 5° C., the temperature was raised to room temperature, and the mixture was stirred for one day. Ethyl acetate (200 ml), water (50 ml) and saturated saline (100 ml) were added to the reaction mixture which was then vigorously shaken, and the solid dispersed in the organic layer was filtered off and washed 5 times with ethyl acetate (50 ml). The filtered solid was dried under reduced pressure to obtain 9.7 g of the title compound as a light violet powder (92% yield).

The NMR data and mass spectrometry (MS) data for the obtained compound were as follows.

NMR: (270 MHz, DMSO-d6) δ: 1.0–1.9 (18H,m), 1.35 (27H,s), 2.8–3.1 (6H,m), 3.9–4.4 (12H,m), 5.45 (1H,s), 6.6–8.0 (42H,m), 10.00 (3H,s).

MS: m/z 1663.0 (M$^+$+23).

Reference Example 2

Synthesis of tris[4-(N-ε-t-butoxycarbonyl-L-lysyl)aminophenyl]methane

The tris[4-[N-α-(9-fluorenylmethoxycarbonyl)-N-εt-butoxycarbonyl-L-lysyl]aminophenyl]methane (9.105 g) obtained in Reference Example 1 was dissolved in N,N-dimethylformamide (30 ml), diethylamine (7.2 ml) was added at room temperature and the mixture was stirred at room temperature for 3 hours. The reaction mixture was concentrated to dryness, the residue was purified by silica gel column chromatography (Chromatorex, NH-Silica, 100–200 mesh) and elution was performed with a mixed solvent of chloroform:methanol=20:1 to obtain 4.77 g of the title compound as a light yellow powder (88% yield).

The NMR data and mass spectrometry (MS) data for the obtained compound were as follows.

NMR: (270 MHz, CDCl$_3$) ε: 1.3–2.1 (24H,m), 1.43 (27H,s), 3.0–3.3 (6H,m), 3.4–3.6 (3H,m), 4.56 (3H,brs), 5.44 (1H,s), 7.05 (6H,d,J=8.2 Hz), 7.50 (6H,d,J=8.2 Hz), 9.44 (3H,s).

MS: m/z 974.1 (M$^+$+1).

Reference Example 3

Synthesis of tris[4-[N-α-[2-(1H-indol-3-yl)acetyl]-N-εt-butoxycarbonyl-L-lysyl]aminophenyl]methane The tris[4-(N-ε-t-butoxycarbonyl-L-lysyl)aminophenyl] methane (100 mg) obtained in Reference Example 2,2-(1H-indol-3-yl)acetic acid (89.9 mg) and 4-dimethylaminopyridine (1.3 mg) were dissolved in a mixed solvent of dichloromethane (1.5 ml) and N,N-dimethylformamide (0.38 ml), after which 1-ethyl-3-(3-dimethylaminopropyl)carbodiimide hydrochloride (98.4 mg) was added under a nitrogen atmosphere at 5° C., the temperature was raised to room temperature, and the mixture was stirred for 3 days. Ethyl acetate (5 ml) and water (5 ml) were added to the reaction mixture which was then vigorously shaken, and the solid dispersed in the organic layer was filtered off and washed with ethyl acetate (2 ml×5). The filtered solid was dried under reduced pressure to obtain 113.8 mg of the title compound as a light violet powder (76% yield).

The NMR data and mass spectrometry (MS) data for the obtained compound were as follows.

NMR: (270 MHz, DMSO-d6) ε: 1.1–1.9 (18H,m), 1.35 (27H,s), 2.8–3.0 (6H,m), 3.5–3.7 (6H,m), 4.3–4.5 (3H,m), 5.42 (1H,s), 6.6–7.7 (30H,m), 8.1–8.3 (3H,m), 9.97 (3H,s), 10.83 (3H,s).

MS: m/z 1467.7 (M$^+$+23).

Reference Example 4

Synthesis of tris[4-[N-α-[2-(5-fluoro-1H-indol-3-yl)acetyl]-N-ε-t-butoxycarbonyl-L-lysyl]aminophenyl]methane Reaction was conducted in the same manner as Reference Example 3, except that 2-(5-fluoro-1H-indol3-yl)acetic acid was used instead of 2-(1H-indol-3-yl)acetic acid, to obtain 40.5 mg of the title compound (53% yield).

The NMR data and mass spectrometry (MS) data for the obtained compound were as follows.

NMR: (270 MHz, DMSO-d6) δ: 1.1–1.9 (18H,m), 1.34 (27H,s), 2.8–3.0 (6H,m), 3.4–3.7 (6H,m), 4.3–4.5 (3H,m), 5.41 (1H,s), 6.6–7.6 (27H,m), 8.1–8.3 (3H,m), 9.97 (3H,s), 10.91 (3H,s).

MS: m/z 1521.7 (M$^+$+23).

Reference Example 5

Synthesis of tris[4-[N-α-[2-(5-bromo-1H-indol-3-yl)acetyl]-N-ε-t-butoxycarbonyl-L-lysyl]aminophenyl]methane Reaction was conducted in the same manner as Reference Example 3, except that 2-(5-bromo-1H-indol-3-yl)acetic acid was used instead of 2-(1H-indol-3-yl)acetic acid, to obtain 33.5 mg of the title compound (65% yield).

The NMR data and mass spectrometry (MS) data for the obtained compound were as follows.

NMR: (270 MHz, DMSO-d6) δ: 1.1–1.9 (18H,m), 1.36 (27H,s), 2.8–3.0 (6H,m), 3.4–3.7 (6H,m), 4.3–4.5 (3H,m), 5.40 (1H,s), 6.5–7.6 (24H,m), 7.77 (3H,s), 8.1–8.3 (3H,m), 9.92 (3H,s), 11.00 (3H,s).

MS: m/z 1705.3 (M$^+$+23).

Reference Example 6

Synthesis of tris[4-[N-α-[2-(5-benzyloxy-1H-indol-3-yl)acetyl]-N-ε-t-butoxycarbonyl-L-lysyl]aminophenyl]methane Reaction was conducted in the same manner as Reference Example 3, using 2-(5-benzyloxy-1H-indol-3-yl)acetic acid instead of 2-(1H-indol-3-yl)acetic acid, to obtain 108.7 mg of the title compound (60% yield).

The NMR data and mass spectrometry (MS) data for the obtained compound were as follows.

NMR: (270 MHz, DMSO-d6) δ: 1.1–1.9 (18H,m), 1.34 (27H,s), 2.8–3.0 (6H,m), 3.4–3.7 (6H,m), 4.3–4.5 (3H,m), 5.05 (6H,ABq,J=18.6 Hz,6.8 Hz), 5.35 (1H,s), 6.5–7.6 (42H,m), 8.21 (3H,d,J=7.9 Hz), 10.00 (3H,s), 10.67 (3H,s).

MS: m/z 1785.7 (M$^+$+23).

Reference Example 7

Synthesis of tris[4-[N-α-[2-(5-methoxy-1H-indol-3-yl)acetyl]-N-ε-t-butoxycarbonyl-L-lysyl]aminophenyl]methane Reaction was conducted in the same manner as Reference Example 3, except that 2-(5-methoxy-1H-indol3-yl)acetic acid was used instead of 2-(1H-indol-3-yl)acetic acid, to obtain 35.7 mg of the title compound (75% yield).

The NMR data and mass spectrometry (MS) data for the obtained compound were as follows.

NMR: (270 MHz, DMSO-d6) δ: 1.1–1.9 (18H,m), 1.35 (27H,s), 2.7–3.0 (6H,m), 3.55 (6H,s), 3.72 (9H,s), 4.34.5 (3H,m), 5.41 (1H,s), 6.5–7.6 (27H,m), 8.15 (3H,d,J=7.6 Hz), 9.97 (3H,s), 10.65 (3H,s).

MS: m/z 1557.7 (M$^+$+23).

Reference Example 8

Synthesis of tris[4-[N-α-[2-(5-methoxy-2-methyl-1-H-indol-3-yl)acetyl]-N-ε-t-butoxycarbonyl-L-lysyl]aminophenyl]methane Reaction was conducted in the same manner as Reference Example 3, except that 2-(5-methoxy-2-methyl-1H-indol-3-yl)acetic acid was used instead of 2-(1H-indol-3-yl)acetic acid, to obtain 27.5 mg of the title compound (57% yield).

The NMR data and mass spectrometry (MS) data for the obtained compound were as follows.

NMR: (270 MHz, DMSO-d6) δ: 1.1–1.9 (18H,m), 1.35 (27H,s), 2.31 (9H,s), 2.7–3.0 (6H,m), 3.49 (6H,ABq,J=18.2 Hz,3.0 Hz), 3.70 (9H,s), 4.3–4.5 (3H,m), 5.41 (1H,s), 6.5–7.6 (24H,m), 8.0–8.2 (3H,m), 9.95 (3H,s), 10.56 (3H,s).

MS: m/z 1599.8 (M$^+$+23).

Reference Example 9

Synthesis of tris[4-[N-α-[2-(2-methyl-1H-indol-3-yl)acetyl]-N-ε-t-butoxycarbonyl-L-lysyl]aminophenyl]methane Reaction was conducted in the same manner as Reference Example 3, except that. 2-(2-methyl-1H-indol3-yl)acetic acid was used instead of 2-(1H-indol-3-yl)acetic acid, to obtain 21.8 mg of the title compound (48% yield).

The NMR data and mass spectrometry (MS) data for the obtained compound were as follows.

NMR: (270 MHz, DMSO-d6) δ: 1.1–1.9 (18H,m), 1.35 (27H,s), 2.51 (9H,s), 2.7–3.0 (6H,m), 3.52 (6H,ABq,J=19.1 Hz,5.0 Hz), 4.3–4.5 (3H,m), 5.41 (1H,s), 6.6–7.6 (27H,m), 7.9–8.2 (3H,m), 9.93 (3H,s), 10.73 (3H,s).

MS: m/z 1509.7 (M$^+$+23).

Reference Example 10

Synthesis of tris[4-[N-α-[2-(2-phenyl-1H-indol-3-yl)acetyl]-N-ε-t-butoxycarbonyl-L-lysyl]aminophenyl]methane Reaction was conducted in the same manner as Reference Example 3, except that 2-(2-phenyl-1H-indol3-yl)acetic acid was used instead of 2-(1H-indol-3-yl)acetic acid, to obtain 29.0 mg of the title compound (56% yield).

The NMR data and mass spectrometry (MS) data for the obtained compound were as follows.

NMR: (270 MHz, DMSO-d6) δ: 1.1–1.9 (18H,m), 1.36 (27H,s), 2.8–3.0 (6H,m), 3.71 (6H,ABq,J=26.4 Hz,8.9 Hz), 4.3–4.6 (3H,m), 5.44 (1H,s), 6.6–8.0 (42H,m), 8.2–8.5 (3H,m), 9.99 (3H,s), 11.23 (3H,s).

MS: m/z 1695.7 (M$^+$+23).

Reference Example 11

Synthesis of tris[4-[N-α-[2-(1-methyl-1H-indol-3-yl)acetyl]-N-ε-t-butoxycarbonyl-L-lysyl]aminophenyl]methane Reaction was conducted in the same manner as Reference Example 3, except that 2-(1-methyl-1H-indol3-yl)acetic acid was used instead of 2-(1H-indol-3-yl)acetic acid, to obtain 45.0 mg of the title compound (98% yield).

The NMR data and mass spectrometry (MS) data for the obtained compound were as follows.

NMR: (270 MHz, DMSO-d6) δ: 1.1–1.8 (18H,m), 1.35 (27H,s), 2.7–3.0 (6H,m), 3.58 (6H,ABq,J=25.0 Hz,2.3 Hz), 3.73 (9H,s), 4.3–4.5 (3H,m), 5.42 (1H,s), 6.6–7.7 (27H,m), 8.2–8.5 (3H,m), 10.11 (3H,s).

MS: m/z 1509.5 (M$^+$+23).

Reference Example 12

Synthesis of tris[4-[N-α-(N-t-butoxycarbonyl-L-tryptophyl)-N-ε-t-butoxycarbonyl-L-lysyl]aminophenyl]methane Reaction was conducted in the same manner as Reference Example 3, using N-α-t-butoxycarbonyl-L-tryptophan instead of 2-(1H-indol-3-yl)acetic acid, to obtain 73.7 mg of the title compound (78% yield).

The NMR data and mass spectrometry (MS) data for the obtained compound were as follows.

NMR: (270 MHz, DMSO-d6) δ: 1.0–1.9 (18H,m), 1.31 (27H,s), 1.34 (27H,s), 2.8–3.2 (12H,m), 4.2–4.4 (3H,m), 4.4–4.6 (3H,m), 5.45 (1H,s), 6.6–7.7 (30H,m), 7.9–8.1 (3H,m), 9.9–10.1 (3H,brs), 10.76 (3H,s).

MS: m/z 1855.5 (M$^+$+23).

Reference Example 13

Synthesis of tris[4-[N-α-[3-(1H-indol-3-yl)propanoyl]N-ε-t-butoxycarbonyl-L-lysyl]aminophenyl]methane Reaction was conducted in the same manner as Reference Example 3, except that 3-(1H-indol-3-yl)propionic acid was used instead of 2-(1H-indol-3-yl)acetic acid, to obtain 22.4 mg of the title compound (49% yield).

The NMR data and mass spectrometry (MS) data for the obtained compound were as follows.

NMR: (270 MHz, DMSO-d6) δ: 1.1–1.9 (18H,m), 1.35 (27H,s), 2.8–3.0 (12H,m), 4.3–4.5 (3H,m), 5.44 (1H,s), 6.6–7.7 (30H,m), 8.10 (3H,d,J=7.6 Hz), 9.99 (3H,s), 10.71 (3H,s.)

MS: m/z 1509.7 (M$^+$+23).

Reference Example 14

Synthesis of tris[4-[N-α-[4-(1H-indol-3-yl)butanoyl]-N-ε-t-butoxycarbonyl-L-lysyl]aminophenyl]methane Reaction was conducted in the same manner as Reference Example 3, except that 4-(1H-indol-3-yl)butanoic acid was used instead of 2-(1H-indol-3-yl)acetic acid, to obtain 43.6 mg of the title compound (56% yield).

The NMR data and mass spectrometry (MS) data for the obtained compound were as follows.

NMR: (270 MHz, DMSO-d6) δ: 1.1–1.8 (18H,m), 1.35 (27H,s), 1.8–2.0 (6H,m), 2.22 (6H,t,J=6.9 Hz), 2.68 (6H,t, J=6.9 Hz), 2.8–3.0 (6H,m), 4.3–4.5 (3H,m), 5.40 (1H,s), 6.5–7.6 (30H,m), 7.99 (3H,d,J=7.6 Hz), 9.95 (3H,s), 10.66 (3H,s).

MS: m/z 1551.5 (M$^+$+23).

Reference Example 15

Synthesis of tris[4-[N-α-[2-(thiophen-3-yl)acetyl]- N-ε-t-butoxycarbonyl-L-lysyl]aminophenyl]methane Reaction was conducted in the same manner as Reference Example 3, except that 2-(thiophen-3-yl)acetic acid was used instead of 2-(1H-indol-3-yl)acetic acid, to obtain 28.6 mg of the title compound (69% yield).

The NMR data and mass spectrometry (MS) data for the obtained compound were as follows.

NMR: (270 MHz, DMSO-d6) δ: 1.1–1.9 (18H,m), 1.35 (27H,s), 2.8–3.0 (6H,m), 3.50 (6H,s), 4.3–4.5 (3H,m), 5.43 (1H,s), 6.6–7.6 (24H,m), 8.27 (3H,d,J=7.9 Hz), 10.01 (3H, s).

MS: m/z 1368.5 (M$^+$+23).

Reference Example 16

Synthesis of tris[4-[N-α-[2-(benzo[b]thiophen-3-yl) acetyl]-N-ε-t-butoxycarbonyl-L-lysyl]aminophenyl] methane Reaction was conducted in the same manner as Reference Example 3, using 2-(benzo[b]thiophen-3-yl)acetic acid instead of 2-(1H-indol-3-yl)acetic acid, to obtain 17.9 mg of the title compound (39% yield).

The NMR data and mass spectrometry (MS) data for the obtained compound were as follows.

NMR: (270 MHz, DMSO-d6) δ: 1.1–1.9 (18H,m), 1.35 (27H,s), 2.8–3.0 (6H,m), 3.6–3.9 (6H,m), 4.3–4.5 (3H,m), 5.44 (1H,s), 6.6–8.0 (30H,m), 8.47 (3H,d,J=7.9 Hz), 10.03 (3H,s).

MS: m/z 1518.5 (M$^+$+23).

Reference Example 17

Synthesis of tris[4-[N-α-(N-t-butoxycarbonyl-L- phenylalanyl)-N-ε-t-butoxycarbonyl-L-lysyl] aminophenyl]methane Reaction was conducted in the same manner as Reference Example 3, except that N-t-butoxycarbonyl-L- phenylalanine was used instead of 2-(1H-indol-3-yl)acetic acid, to obtain 24.9 mg of the title compound (47% yield).

The NMR data and mass spectrometry (MS) data for the obtained compound were as follows.

NMR: (270 MHz, DMSO-d6) δ: 1.1–1.9 (18H,m), 1.30 (27H,s), 1.34 (27H,s), 2.6–3.2 (12H,m), 4.1–4.3 (3H,m), 4.3–4.5 (3H,m), 5.45 (1H,s), 6.6–7.7 (30H,m), 8.02 (3H,d, J=7.6 Hz), 10.02 (3H,s).

MS: m/z 1521.7 (M$^+$+23).

Reference Example 18

Synthesis of tris[4-[N-α-[2-(4-benzyloxyphenyl) acetyl]N-ε-t-butoxycarbonyl-L-lysyl]aminophenyl] methane Reaction was conducted in the same manner as Reference Example 3, except that 2-(4-benzyloxyphenyl)acetic acid was used instead of 2-(1H-indol-3-yl)acetic acid, to obtain 103.4 mg of the title compound (61% yield).

The NMR data and mass spectrometry (MS) data for the obtained compound were as follows.

NMR: (270 MHz, DMSO-d6) δ: 1.1–1.8 (18H,m), 1.35 (27H,s), 2.8–3.0 (6H,m), 3.3–3.5 (6H,m), 4.3–4.5 (3H,m), 5.05 (6H,s), 5.42 (1H,s), 6.6–7.6 (42H,m), 8.24 (3H,d,J=6.8 Hz), 9.99 (3H,s).

MS: m/z 1668.7 (M$^+$+23).

Reference Example 19

Synthesis of tris[4-[N-α-(3-pyridylcarbonyl)-N-ε-t- butoxycarbonyl-L-lysyl]aminophenyl]methane Reaction was conducted in the same manner as Reference Example 3, except that 3-pyridylcarboxylic acid was used instead of 2-(1H-indol-3-yl)acetic acid, to obtain 33.1 mg of the title compound (50% yield).

The NMR data and mass spectrometry (MS) data for the obtained compound were as follows.

NMR: (270 MHz, DMSO-d6) δ: 1.1–1.7 (12H,m), 1.34 (27H,s), 1.7–2.0 (6H,m), 2.8–3.0 (6H,m), 4.4–4.7 (3H,m), 5.45 (1H,s), 6.6–6.8 (3H,m), 7.00 (6H,d,J=8.4 Hz), 7.47.6 (3H,m), 7.54 (6H,d,J=8.4 Hz), 8.1–8.9 (9H,m), 9.05 (3H,s), 10.08 (3H,s).

MS: m/z 1521.7 (M$^+$+23).

Reference Example 20

Synthesis of tris[4-[N-α-(2-(5-hydroxy-1H-indol-3- yl)acetyl]-N-ε-t-butoxycarbonyl-L-lysyl] aminophenyl methane The tris[4-[N-α-2-(5-benzyloxy-1H-indol-3-yl)acetyl-N- ε-t-butoxycarbonyl-L-lysyl]aminophenyl]methane (52.4 mg) obtained in Reference Example 6 was dissolved in N,N-dimethylformamide (1 ml), 10%-Pd/C (29.5 mg) was added thereto, and then the mixture was stirred for 13 hours at room temperature under a hydrogen atmosphere. The reaction mixture was filtered with celite, the filtrate was concentrated and exsiccated, and the residue was washed with methanol-diethyl ether to obtain 37.6 mg of the title compound (85% yield).

The NMR data and mass spectrometry (MS) data for the obtained compound were as follows.

NMR: (270 MHz, DMSO-d6) δ: 1.1–1.9 (18H,m), 1.34 (27H,s), 2.8–3.0 (6H,m), 3.4–3.6 (6H,m), 4.3–4.5 (3H,m), 5.41 (1H,s), 6.5–7.6 (27H,m), 8.00 (3H,d,J=7.6 Hz), 8.51 (3H,s), 9.93 (3H,s), 10.49 (3H,s).

MS: m/z 1521.7 (M$^+$+23).

Reference Example 21

Synthesis of tris[4-[N-α-[2-(4-hydroxyphenyl) acetyl]-N-ε-t-butoxycarbonyl-L-lysyl]aminophenyl] methane Reaction was conducted in the same manner as Reference Example 21, using the tris[4-[N-α-[2-(4-benzyloxyphenyl) acetyl]-N-ε-t-butoxycarbonyl-L-lysyl]aminophenyl] methane obtained in Reference Example 18, to obtain 22.0 mg of the title compound (72% yield).

The NMR data and mass spectrometry (MS) data for the obtained compound were as follows.

NMR: (270 MHz, DMSO-d6) δ: 1.1–1.9 (18H,m), 1.35 (27H,s), 2.8–3.0 (6H,m), 3.2–3.5 (6H,m), 4.2–4.5 (3H,m), 5.42 (1H,s), 6.65 (6H,d,J=7.4 Hz), 6.6–6.8 (3H,m), 6.98 (6H,d,J=7.7 Hz), 7.03 (6H,d,J=7.4 Hz), 7.49 (6H,d,J=7.7 Hz), 8.15 (3H,d,J=7.6 Hz), 9.14 (3H,s), 9.96 (3H,s).

MS: m/z 1521.7 (M$^+$+23).

Reference Example 22

Synthesis of N-α-[2-(2-tolyl)acetyl]-N-ε-t-butoxycarbonyl-L-lysine]

N-ε-t-butoxycarbonyl-L-lysine (1.35 g) was suspended in dichloromethane (8 ml), and then N,O-bis(trimethylsilyl)acetamide (2.8 ml) was added while stirring at room temperature to prepare a solution (hereinafter referred to as Solution A). Next, 2-(2-tolyl)acetic acid (0.75 g) and N-methylmorpholine (605 μl) were dissolved in dichloromethane (15 ml), isobutyloxycarbonyl chloride (722 μl) was added while stirring at −10° C., and stirring was continued for 20 minutes. Solution A was then added dropwise, and the mixture was stirred at a temperature of between −10° C. and 0° C. for 3 hours. Dichloromethane and 1 N hydrochloric acid were added to the reaction mixture which was then vigorously shaken, and the organic layer was separated off. The aqueous layer was washed with dichloromethane. After combining the organic layer and washing with saturated saline, drying was performed over magnesium sulfate. The organic layer was filtered and the filtrate was concentrated under reduced pressure. The residue was washed with n-hexane and dissolved in dichloromethane (10 ml), and then n-hexane (100 ml) was added. The produced precipitate was isolated and dried under reduced pressure to obtain 1.12 g of the title compound as a colorless powder (59% yield).

The NMR data and mass spectrometry (MS) data for the obtained compound were as follows.

NMR: (270 MHz, CDCl$_3$) δ: 1.14–1.93 (15H,m), 2.28 (3H,s), 2.93–3.11 (2H,m), 3.61 (2H,s), 4.43–4.60 (1H,m), 7.11–7.24 (4H,m).

MS: m/z 401 (M$^+$+23).

Reference Example 23

Synthesis of tris[4-[N-α-[2-(2-tolyl)acetyl]-N-ε-t-butoxycarbonyl-L-lysyl]aminophenyl]methane The N-α-[2-(2-tolyl)acetyl]-N-ε-t-butoxycarbonyl-L-lysine (378 g) obtained in Reference Example 22, tris(4-aminophenyl)methane (87 mg) and 1-hydroxybenzotriazole monohydrate (77 mg) were dissolved in N,N-dimethylformamide (2 ml), 1-ethyl-3-(3-dimethylaminopropyl)carbodiimide hydrochloride (211 mg) was added at 0° C. and the mixture was stirred at a temperature from 0° C. to room temperature for one day. The reaction mixture was diluted with ethyl acetate, and then washed twice with saturated sodium bicarbonate water and once each with 1 N hydrochloric acid and saturated saline in that order. The organic layer was concentrated to dryness, the residue was purified by silica gel column chromatography (Wako C-200, 75–150 μm) and elution was performed with a mixed solvent of chloroform:methanol=20:1 to obtain 192 mg of a light red powder. A 137 mg portion thereof was purified with an ion-exchange silica gel column (BONDESIL, phase: SCX 40UM) and eluted with a mixed solvent of dichloromethane:methanol=1:1 and then with methanol to obtain 58 mg of the title compound as a colorless powder (20% yield).

The NMR data and mass spectrometry (MS) data for the obtained compound were as follows.

NMR: (270 MHz, DMSO-d6) δ: 1.06–1.49 (39H,m), 1.50–1.81 (6H,m), 2.24 (9H,s), 2.80–2.97 (6H,m), 3.52 (6H,s), 4.27–4.47 (3H,m), 5.44 (1H,s), 6.66–6.80 (3H,m), 7.00 (6H,d,J=8.4 Hz), 7.04–7.23 (12H,m), 7.50 (6H,d,J=8.4 Hz), 8.24 (3H,d,J=7.8 Hz), 10.0 (3H,s).

MS: m/z 1393 (M$^+$+23).

Reference Example 24

Synthesis of tris[f4-[(N-α-(9-fluorenylmethoxycarbonyl)N-ε-benzyloxycarbonyl-D-lysyl]aminophenyl]methane Tris(4-aminophenyl)methane (916 mg), N-α-(9-fluorenylmethoxycarbonyl)-N-α-benzyloxycarbonyl-D-lysine (5.01 g) and N-methylmorpholine (1.15 g) were dissolved in N,N-dimethylformamide (50 ml), after which O-(7-azabenzotriazol-1-yl)-1,1,3,3-tetramethyluronium hexafluorophosphate (3.79 g) was added under a nitrogen atmosphere at 5° C., the temperature was raised to room temperature, and the mixture was stirred for 18 hours. Ethyl acetate (600 ml) and water (400 ml) were added to the reaction mixture which was then vigorously shaken, and the solid dispersed in the organic layer was filtered off and washed with water (200 ml) and ethyl acetate (200 ml). The filtered solid was dried under reduced pressure to obtain 4.74 g of the title compound as a light violet powder (86% yield).

The NMR data for the obtained compound were as follows.

NMR: (270 MHz, DMSO-d6) δ: 1.3–1.5 (12H,m), 1.61.8 (6H, m), 2.9–3.1 (6H,m), 4.1–4.4 (12H,m), 5.02 (6H,s), 5.48 (1H,s), 7.04 (6H,d,J=7.9 Hz), 7.26–7.70 (39H,m), 7.70–7.82 (6H,m), 7.92 (6H,d,J=7.4 Hz), 10.02 (3H,s).

Reference Example 25

Synthesis of tris[4-(N-α-benzyloxycarbonyl-D-lysyl)aminophenyl]methane

A piperidine-containing N,N-dimethylformamide solution (20% (v/v), 40 ml) was added to the tris[4-[N-α-(9-fluorenylmethoxycarbonyl)-N-α-benzyloxycarbonyl-D-lysyl]aminophenyl]methane (4.74 g) obtained in Reference Example 24 at room temperature, and the mixture was stirred at room temperature for one hour. The reaction mixture was concentrated to dryness, the residue was purified by silica gel column chromatography (Chromatorex, NH-Silica, 100–200 mesh) and elution was performed with a mixed solvent of chloroform:methanol=20:1 to obtain 2.81 g of the title compound as a light yellow powder (quantitative yield).

The NMR data and mass spectrometry (MS) data for the obtained compound were as follows.

NMR: (270 MHz, DMSO-d6) δ: 1.2–1.8 (18H,m), 2.953.10 (6H,m), 3.24–3.35 (3H,m), 5.02 (6H,s), 5.47 (1H, s), 7.03 (6H,d,J=8.4 Hz), 7.2–7.3 (3H,m), 7.3–7.5 (15H,m), 7.58 (6H,d,J=8.4 Hz).

MS: m/z 1076.1 (M$^+$+1).

Reference Example 26

Synthesis of tris[4-[N-α-[2-(2-methyl-1H-indol-3-yl)acetyl]-N-ε-benzyloxycarbonyl-D-lysyl]aminophenyl]methane The tris[4-(N-ε-benzyloxycarbonyl-D-lysyl)aminophenyl]methane (20.9 mg) obtained in Reference Example 25, 2-(2-methyl-1H-indol-3-yl)acetic acid (18.4 mg) and 3,4-dihydro-3-hydroxy-4-oxo-1,2,3-benzotriazine (14.9 mg) were dissolved in a mixed solvent of dichloromethane (0.2 ml) and N,N-dimethylformamide (0.1 ml), after which 1-ethyl-3-(3-dimethylaminopropyl) carbodiimide hydrochloride (18.6 mg) was added under a nitrogen atmosphere at 5° C., the temperature was raised to room temperature, and the mixture was stirred for 13 hours and 30 minutes. The reaction mixture was poured into water (5 ml) and extracted with ethyl acetate (5 ml×2). The organic layer was washed with water 5 ml) and saturated saline (5 ml) and then dried over sodium sulfate and concentrated under reduced pressure. The residue was purified by silica gel column chromatography (Kiesel-gel 60, 240–400 mesh) and elution was performed with a mixed solvent of chloroform:methanol=95:5 to obtain 20.2 mg of the title compound as a colorless powder (65% yield).

The NMR data and mass spectrometry (MS) data for the obtained compound were as follows.

NMR: (270 MHz, DMSO-d6) δ: 1.1–1.9 (18H,m), 2.33 (9H,s), 2.9–3.1 (6H,m), 3.52 (6H,ABq,J=20.8 Hz,5.6 Hz), 4.3–4.5 (3H,m), 4.98 (6H,s), 5.40 (1H,s), 6.7–7.7 (42H,m), 7.9–8.1 (3H,m), 9.93 (3H,s), 10.72 (3H,s).

MS: m/z 1611.9 (M$^+$+23).

Reference Example 27

Synthesis of tris[4-[N-α-(9-fluorenylmethoxycarbonyl)-N-ε-t-butoxycarbonyl-D-lysyl]aminophenyl]methane Tris(4-aminophenyl)methane (1.45 g), N-α-(9-fluorenylmethoxycarbonyl)-N-ε-t-butoxycarbonyl-D-lysine (7.38 g) and N-methylmorpholine (1.82 g) were dissolved in N,N-dimethylformamide (75 ml), after which O-(7-azabenzotriazol-1-yl)-1,1,3,3-tetramethyluronium hexafluorophosphate (5.99 g) was added under a nitrogen atmosphere at 5° C., the temperature was raised to room temperature, and the mixture was stirred for 18 hours. Ethyl acetate (800 ml) and water (600 ml) were added to the reaction mixture which was then vigorously shaken, and the solid dispersed in the organic layer was filtered off and washed with water (300 ml) and ethyl acetate (300 ml). The filtered solid was dried under reduced pressure to obtain 6.53 g of the title compound as a light violet powder (80% yield).

The NMR data for the obtained compound were as follows.

NMR: (270 MHz, DMSO-d6) δ: 1.2–1.5 (12H,m), 1.35 (27H,s), 1.5–1.8 (6H,m), 2.8–3.1 (6H,m), 3.9–4.4 (12H,m), 5.45 (1H,s), 6.79 (3H,s), 7.04 (6H,d,J=7.9 Hz), 7.26–7.70 (21H,m), 7.70–7.82 (6H,m), 7.91 (6H,d,J=7.4 Hz), 10.00 (3H,s).

Reference Example 28

Synthesis of tris[4-(N-ε-t-butoxycarbonyl-D-lysyl)aminophenyl]methane

A piperidine-containing N,N-dimethylformamide solution (20% (v/v), 40 ml) was added to the tris[4-[N-α-(9-fluorenylmethoxycarbonyl)-N-ε-t-butoxycarbonyl-D-lysyl]aminophenyl]methane (6.53 g) obtained in Reference Example 27 at room temperature, and the mixture was stirred at room temperature for one hour. The reaction mixture was concentrated to dryness, the residue was purified by silica gel column chromatography (Chromatorex, NH-Silica, 100–200 mesh) and elution was performed with a mixed solvent of chloroform:methanol=20:1 to obtain 4.0 g of the title compound as a light yellow powder (quantitative yield).

The NMR data for the obtained compound were as follows.

NMR: (270 MHz, DMSO-d6) δ: 1.2–1.7 (18H,m), 1.39 (21H,s), 2.95–3.00 (6H,m), 3.24–3.35 (3H,m), 5.47 (1H,s), 6.7–6.8 (3H,m), 7.04 (6H,d,J=8.5 Hz), 7.58 (6H,d,J=8.5 Hz).

MS: m/z 974.4 (M$^+$+1).

Reference Example 29

Synthesis of tris[4-[N-α-[2-(5-methoxy-2-methyl-1H-indol-3-yl)acetyl]-N-ε-t-butoxycarbonyl-D-lysyl]aminophenyl]methane The tris[4-(N-ε-t-butoxycarbonyl-D-lysyl)aminophenyl] methane (270 mg) obtained in Reference Example 28, 2-(5-methoxy-2-methyl-1H-indol-3-yl)acetic acid (243 mg) and N-methylmorpholine (183 μl) were dissolved in N,N-dimethylformamide (4 ml), after which O-(7-azabenzotriazol-1-yl)-1,1,3,3-tetramethyluronium hexafluorophosphate (421.5 mg) was added under a nitrogen atmosphere at 5° C., the temperature was raised to room temperature, and the mixture was stirred for 12 hours. The reaction mixture was poured into water and extracted with ethyl acetate (50 ml×2). The organic layer was washed with 0.1 N aqueous hydrochloric acid (20 ml), water (20 ml), saturated sodium bicarbonate water (20 ml) and saturated saline (20 ml) and then dried over sodium sulfate and concentrated to 10 ml. The precipitated solid was filtered, washed with ethyl acetate and water and then dried under reduced pressure to obtain 378.9 mg of the title compound as a light yellow powder (87% yield).

The NMR data and mass spectrometry (MS) data for the obtained compound were as follows.

NMR: (270 MHz, DMSO-d6) δ: 1.1–1.9 (18H,m), 1.35 (27H,s), 2.31 (9H,s), 2.7–3.0 (6H,m), 3.3–3.6 (6H,m), 3.70 (9H,s), 4.3–4.5 (3H,m), 5.41 (1H,s), 6.5–7.6 (24H,m), 7.9–8.2 (3H,m), 9.92 (3H,s), 10.54 (3H,s).

MS: m/z 1599.8 (M$^+$+23).

Reference Example 30

Synthesis of tris[4-[N-α-[2-(pyridin-3-yl)acetyl]-N-εt-butoxycarbonyl-L-lysyl]aminophenyl]methane Reaction was conducted in the same manner as Reference Example 3, except that 2-(pyridin-3-yl)acetic acid was used instead of 2-(1H-indol-3-yl)acetic acid, to obtain 35.4 mg of the title compound (52% yield).

The NMR data for the obtained compound were as follows.

NMR: (270 MHz, DMSO-d6) δ: 1.1–1.9 (18H,m), 1.35 (27H,s), 2.8–3.0 (6H,m), 3.54 (6H,s), 4.3–4.5 (3H,m), 5.42 (1H,s), 6.6–7.8 (21H,m), 8.2–8.6 (9H,m), 10.04 (3H,s).

Reference Example 31

Synthesis of tris(4-formylaminophenyl)methane

Tris(4-aminophenyl)methane (2.9 g), formic acid (4.6 g) and 4-dimethylaminopyridine (122 mg) were dissolved in dichloromethane (30 ml), after which 1-ethyl-3-(3-dimethylaminopropyl)carbodiimide hydrochloride (9.61 g) was added under a nitrogen atmosphere at 5° C., the temperature was raised to room temperature, and the mixture was stirred for 2 days. Ethyl acetate (100 ml) and water (50 ml) were added to the reaction mixture which was then vigorously shaken, and the organic layer was washed with saturated sodium bicarbonate water (20 ml), water (20 ml) and saturated aqueous sodium chloride (20 ml), dried over sodium sulfate, and concentrated to dryness. The residue was purified by silica gel column chromatography (Kieselgel 60, 240–400 mesh) and elution was performed with a mixed solvent of chloroform:methanol=90:10 to obtain 1.63 g of the title compound as a light brown powder (44% yield).

The NMR data and mass spectrometry (MS) data for the obtained compound were as follows.

NMR: (270 MHz, DMSO-d6) δ: 5.46 (1H,s), 7.03 (6H, d,J=8.3 Hz), 7.50 (6H,d,J=8.3 Hz), 8.23 (3H,s), 10.11 (3H, s).

MS: m/z 374.1 (M$^+$+1).

Reference Example 32

Synthesis of tris (4-methylaminophenyl)methane

The tris(4-formylaminophenyl)methane (130 mg) obtained in Reference Example 31 was dissolved in tetrahydrofuran (5 ml), after which lithium aluminum hydride (66.1 mg) was added under a nitrogen atmosphere at 5° C., the temperature was raised to room temperature, and the mixture was stirred for 19 hours. Water (5 ml) was added to the reaction mixture at 5° C., and stirring was continued for 10 minutes. The reaction mixture was filtered with celite and the filtrate was concentrated to dryness. The residue was purified by silica gel column chromatography (Kiesel-gel 60, 240–400 mesh) and elution was performed with a mixed solvent of chloroform:methanol=98:2 to obtain 81.1 mg of the title compound as a yellow oily substance (70% yield).

The NMR data for the obtained compound were as follows.

NMR: (270 MHz, CDCl$_3$) 5; 1.55 (3H,s), 2.80 (9H,s), 5.25 (1H,s), 6.52 (6H,d,J=8.4 Hz), 6.93 (6H,d,J=8.4 Hz).

Reference Example 33

Synthesis of tris[4-[N-[N-α-(9-fluorenylmethoxycarbonyl)-N-ε-benzyloxycarbonyl-L-lysyl]-N-methyl]aminophenyl]methane The tris(4-methylaminophenyl)methane (79.5 mg) obtained in Reference Example 32, N-α-(9-fluorenylmethoxycarbonyl)-N-ε-benzyloxycarbonyl-L-lysine (482.5 mg) and N-methylmorpholine (145.7 mg) were dissolved in N,N-dimethylformamide (3.5 ml), after which O-(7-azabenzotriazol-1-yl)-1,1,3,3-tetramethyluronium hexafluorophosphate (365 mg) was added under a nitrogen atmosphere at 5° C., the temperature was raised to room temperature, and the mixture was stirred for 2 days. The reaction mixture was poured into water and extracted with ethyl acetate (20 ml+10 ml). The organic layer was washed with 0.1 N aqueous hydrochloric acid (10 ml), water (10 ml), saturated sodium bicarbonate water (10 ml) and saturated saline (10 ml), and then dried over sodium sulfate and concentrated to dryness. The residue was purified by silica gel column chromatography (Kiesel-gel 60, 240–400 mesh) and elution was performed with a mixed solvent of chloroform:methanol=98:2 to obtain 226.4 mg of the title compound as a light yellow powder (53% yield).

The NMR data and mass spectrometry (MS) data for the obtained compound were as follows.

NMR: (270 MHz, CDCl$_3$) δ: 1.0–1.9 (18H,m), 2.8–3.1 (6H,m), 3.25 (9H,s), 4.0–4.5 (12H,m), 5.01 (6H,s), 5.15.3 (3H,m), 5.53 (3H,s), 5.55 (1H,s), 7.0–7.9 (51H,m).

MS: m/z 1784.4 (M$^+$+1).

Reference Example 34

Synthesis of tris[4-[N-[N-α-(9-fluorenylmethoxycarbonyl)-N-ε-benzyloxycarbonyl-D-lysyl]-N-methyl]aminophenyl]methane Reaction was conducted in the same manner as Reference Example 33, except that N-α-(9-fluorenylmethoxycarbonyl)-N-ε-benzyloxycarbonyl-D-lysine was used instead of N-α-(9-fluorenylmethoxycarbonyl)-N-ε-benzyloxycarbonyl-L-lysine, to obtain 280 mg of the title compound as a light yellow powder (18% yield).

The NMR data and mass spectrometry (MS) data for the obtained compound were as follows.

NMR: (270 MHz, CDCl$_3$) δ: 1.0–1.9 (18H,m), 2.8–3.1 (6H,m), 3.25 (9H,s), 4.0–4.5 (12H,m), 5.01 (6H,s), 5.15.3 (3H,m), 5.53 (3H,s), 5.55 (1H,s), 7.0–7.9 (51H,m).

MS: m/z 1784.3 (M$^+$+1).

Reference Example 35

Synthesis of tris[4-[N-[N-ε-benzyloxycarbonyl-L-lysyl]-N-methyl]aminophenyl]methane The tris[4-[N-[N-α-(9-fluorenylmethoxycarbonyl)-N-ε-benzyloxycarbonyl-L-lysyl]-N-methyl]aminophenyl]methane (180 mg) obtained in Reference Example 33 was dissolved in dichloromethane (0.8 ml), diethylamine (0.2 ml) was added at room temperature and the mixture was stirred at room temperature for 5 hours. The reaction mixture was concentrated to dryness, the residue was purified by silica gel column chromatography (Chromatorex, NH-Silica, 100–200 mesh) and elution was performed with a mixed solvent of chloroform:methanol=20:1 to obtain 99 mg of the title compound as a light yellow powder (88% yield).

The NMR data and mass spectrometry (MS) data for the obtained compound were as follows.

NMR: (270 MHz, CDCl$_3$) δ: 1.0–2.0 (24H,m), 3.0–3.2 (6H,m), 3.26 (9H,s), 3.2–3.5 (3H,m), 4.9–5.1 (3H,m), 5.06 (6H,s), 5.58 (1H,s), 7.0–7.5 (27H,m).

MS: m/z 1118.7 (M$^+$+1).

Reference Example 36

Synthesis of tris[4-[N-(N-ε-benzyloxycarbonyl-D-lysyl)-N-methyl]aminophenyl]methane Reaction was conducted in the same manner as Reference Example 35, except that the tris[4-[N-[N-α-(9-fluorenylmethoxycarbonyl)-N-ε-benzyloxycarbonyl-D-lysyl]-N-methyl]aminophenyl]methane obtained in Reference Example 34 was used instead of tris[4-[N-[N-α-(9-fluorenylmethoxycarbonyl)-N-ε-benzyloxycarbonyl-L-lysyl]-N-methyl]aminophenyl]methane, to obtain 124.1 mg of the title compound as a light yellow powder (71% yield).

The NMR data and mass spectrometry (MS) data for the obtained compound were as follows.

NMR: (270 MHz, CDCl$_3$) δ: 1.0–2.0 (24H,m), 3.0–3.2 (6H,m), 3.26 (9H,s), 3.2–3.5 (3H,m), 4.9–5.1 (3H,m), 5.06 (6H,s), 5.58 (1H,s), 7.0–7.5 (27H,m).

MS: m/z 1118.6 (M$^+$+1).

Reference Example 37

Synthesis of tris[4-[N-[N-α-[2-(1H-indol-3-yl) acetyl]N-ε-benzyloxycarbonyl-L-lysyl]-N-methyl] aminophenyl]methane The tris[4-[N-[N-ε-benzyloxycarbonyl-L-lysyl]-N-methyl]aminophenyl]methane (40 mg) obtained in Reference Example 35, 2-(1H-indol-3-yl)acetic acid (25.1 mg) and N-methylmorpholine (23.6 μl) were dissolved in N,N-dimethylformamide (0.5 ml), after which O-(7-azabenzotriazol-1-yl)-1,1,3,3-tetramethyluronium hexafluorophosphate (54.4 mg) was added under a nitrogen atmosphere at 5° C., the temperature was raised to room temperature, and the mixture was stirred for 4 hours. The reaction mixture was poured into water and extracted with ethyl acetate (5 ml×2). The organic layer was washed with 0.1 N aqueous hydrochloric acid (5 ml), water (5 ml), saturated sodium bicarbonate water (5 ml) and saturated saline (5 ml), and then dried over sodium sulfate and concentrated to dryness. The residue was purified by silica gel column chromatography (Kiesel-gel 60, 240–400 mesh) and elution was performed with a mixed solvent of chloroform:methanol=95:5 to obtain 57 mg of the title compound as a light brown powder (quantitative yield).

The NMR data and mass spectrometry (MS) data for the obtained compound were as follows.

NMR: (270 MHz, DMSO-d6) δ: 0.8–1.6 (18H,m), 2.63.0 (6H,m), 3.09 (9H,s), 3.51 (6H,s), 4.2–4.4 (3H,m), 4.97 (6H,s), 5.60 (1H,s), 6.8–7.6 (45H,m), 8.0–8.2 (3H,m), 10.77 (3H,s).

MS: m/z 1589.3 (M$^+$+1).

Reference Example 38

Synthesis of tris[4-[N-[N-α-[2-(1H-indol-3-yl) acetyl]N-ε-benzyloxycarbonyl-D-lysyl]-N-methyl] aminophenyl]methane Reaction was conducted in the same manner as Reference Example 37, except that the tris[4-[N-[N-ε-benzyloxycarbonyl-D-lysyl]-N-methyl]aminophenyl]methane obtained in Reference Example 36 was used instead of tris[4-[N-[N-ε-benzyloxycarbonyl-L-lysyl]-N-methyl]aminophenyl]methane, to obtain 51.3 mg of the title compound as light yellow crystals (90% yield).

The NMR data and mass spectrometry (MS) data for the obtained compound were as follows.

NMR: (270 MHz, DMSO-d6) δ: 0.8–1.6 (18H,m), 2.63.0 (6H,m), 3.10 (9H,s), 3.51 (6H,s), 4.2–4.4 (3H,m), 4.98 (6H,s), 5.65 (1H,s), 6.8–7.6 (45H,m), 8.0–8.2 (3H,m), 10.76 (3H,s).

MS: m/z 1589.4 (M$^+$+1).

Reference Example 39

Synthesis of tris[4-[N-[N-α-[2-(5-methoxy-2-methyl-1H-indol-3-yl)acetyl]-N-ε-benzyloxycarbonyl-L-lysyl]-N-methyl]aminophenyl] methane Reaction was conducted in the same manner as Reference Example 37, except that 2-(5-methoxy-2-methyl-1H-indol-3-yl)acetic acid was used instead of 2(1H-indol-3-yl)acetic acid, to obtain 55 mg of the title compound as a light yellow powder (89% yield).

The NMR data and mass spectrometry (MS) data for the obtained compound were as follows.

NMR: (270 MHz, DMSO-d6) δ: 0.8–1.7 (18H,m), 2.26 (9H,s), 2.6–2.9 (6H,m), 3.07 (9H,s), 3.3–3.6 (6H,m), 3.70 (9H,s), 4.2–4.4 (3H,m), 4.97 (6H,s), 5.56 (1H,s), 6.5–7.5 (39H,m), 7.9–8.1 (3H,m), 10.48 (3H,s).

MS: m/z 1721.6 (M$^+$+1).

Reference Example 40

Synthesis of tris[4-[N-[N-α-[2-(5-methoxy-2-methyl-1H-indol-3-yl)acetyl]-N-ε-benzyloxycarbonyl-D-lysyl]-N-methyl] aminophenyl]methane Reaction was conducted in the same manner as Reference Example 37, except that the tris[4-[N-[N-εbenzyloxycarbonyl-D-lysyl]-N-methyl]aminophenyl] methane obtained in Reference Example 36 was used instead of tris[4-[N-[N-ε-benzyloxycarbonyl-L-lysyl]-N-methyl]aminophenyl]methane, and 2-(5-methoxy-2-methyl-1H-indol-3-yl)acetic acid was used instead of 2-(1H-indol-3-yl)acetic acid, to obtain 60.7 mg of the title compound as light yellow crystals (99% yield).

The NMR data and mass spectrometry (MS) data for the obtained compound were as follows.

NMR: (270 MHz, DMSO-d6) δ: 0.8–1.7 (18H,m), 2.26 (9H,s), 2.6–2.9 (6H,m), 3.07 (9H,s), 3.3–3.6 (6H,m), 3.70 (9H,s), 4.2–4.4 (3H,m), 4.97 (6H,s), 5.56 (1H,s), 6.5–7.5 (39H,m), 7.9–8.1 (3H,m), 10.49 (3H,s)

MS: m/z 1721.6 (M$^+$+1).

Reference Example 41

Synthesis of tris[4-[N-α-(9-fluorenylmethoxycarbonyl)N-ε-dimethyl-L-lysyl] aminophenyl]methane Tris(4-aminophenyl)methane (31.4 mg), N-α-(9-fluorenylmethoxycarbonyl)-N-ε-dimethyl-L-lysine (145.7 mg) and N-methylmorpholine (108 μl) were dissolved in N,N-dimethylformamide (1.5 ml), after which O-(7-azabenzotriazol-1-yl)-1,1,3,3-tetramethyluronium hexafluorophosphate (145.1 mg) was added under a nitrogen atmosphere at 5° C., the temperature was raised to room temperature, and the mixture was stirred for 2 hours. The reaction mixture was poured into water (5 ml), ethyl acetate (5 ml) was added, and the mixture was vigorously stirred. The precipitate was filtered, washed with ethyl acetate (1 ml×3) and then dried to obtain 153.8 mg of the title compound as a light brown powder.

The mass spectrometry (MS) data for the obtained compound were as follows.

MS: m/z 1424.8 (M$^+$+1).

Reference Example 42

Synthesis of tris[4-[N-α-dimethyl-L-lysyl] aminophenyl]methane

The tris[4-[N-α-(9-fluorenylmethoxycarbonyl)-N-εdimethyl-L-lysyl]aminophenyl]methane (58.3 mg) obtained in Reference Example 41 was dissolved in N,N-dimethylformamide (0.8 ml), piperidine (0.2 ml) was added at room temperature and the mixture was stirred for 2 hours.

The reaction mixture was concentrated to dryness under reduced pressure, the residue was purified by silica gel column chromatography (Chromatorex, NH-Silica, 100–200 mesh) and elution was performed with a mixed solvent of chloroform:methanol=93:7 to obtain 27.1 mg of the title compound as a light yellow powder (48% yield).

The NMR data and mass spectrometry (MS) data for the obtained compound were as follows.

NMR: (270 MHz, CDCl$_3$) δ: 1.3–2.1 (24H,m), 2.20 (18H,s), 2.2–2.5 (6H,m), 3.46 (3H,dd,J=7.9 Hz,4.0 Hz), 5.44 (1H,s), 7.04 (6H,d,J=8.3 Hz), 7.49 (6H,d,J=8.3 Hz), 9.45 (3H,s).

MS: m/z 758.7 (M$^+$+1).

Reference Example 43

Synthesis of tris[4-[N-(9-fluorenylmethoxycarbonyl)-S-[3-(N-t-butoxycarbonyl)aminopropyl]-L-cystyl]aminophenyl]methane Tris(4-aminophenyl)methane (50 mg), N-(9-fluorenylmethoxycarbonyl)-S-[3-(N-t-butoxycarbonyl)aminopropyl]-L-cysteine (285.4 mg) and N-methylmorpholine (94 μl) were dissolved in N,N-dimethylformamide (2 ml), after which O-(7-azabenzotriazol-1-yl)-1,1,3,3-tetramethyluronium hexafluorophosphate (216.8 mg) was added under a nitrogen atmosphere at 5° C., the temperature was raised to room temperature, and the mixture was stirred for 2.5 hours. The reaction mixture was poured into water (5 ml), ethyl acetate (5 ml) was added and the mixture was vigorously stirred. The precipitate was filtered, washed with ethyl acetate (1 ml×3) and then dried to obtain 236.4 mg of the title compound as a light violet powder (79% yield).

The NMR data for the obtained compound were as follows. NMR: (270 MHz, DMSO-d6) δ: 1.35 (27H,s), 1.51.8 (6H,m), 2.4–3.1 (18H,m), 4.1–4.5 (12H,m), 5.46 (1H,s), 6.6–8.0 (42H,m), 10.15 (3H,s).

Reference Example 44

Synthesis of tris[4-[S-[3-(N-tbutoxycarbonyl)aminopropyl]-L-cystyl]aminophenyl]methane The tris[4-[N-(9-fluorenylmethoxycarbonyl)-S-[3(N-t-butoxycarbonyl)aminopropyl]-L-cystyl]aminophenyl]methane (211.7 mg) obtained in Reference Example 43 was dissolved in N,N-dimethylformamide (1.3 ml), piperidine (0.4 ml) was added at room temperature and the mixture was stirred for 3 hours. The reaction mixture was concentrated under reduced pressure, the residue was purified by silica gel column chromatography (Chromatorex, NH-Silica, 100–200 mesh) and elution was performed with a mixed solvent of chloroform:methanol=93:7 to obtain 130.1 mg of the title compound as a light yellow powder (quantitative yield).

The NMR data and mass spectrometry (MS) data for the obtained compound were as follows.

NMR: (270 MHz, DMSO-d6) δ: 1.43 (27H,s), 1.5–2.1 (12H,m), 2.5–3.4 (18H,m), 3.5–3.8 (3H,m), 4.5–4.8 (3H,m), 5.45 (1H,s), 7.05 (6H,d,J=8.4 Hz), 7.49 (6H,d,J=8.4 Hz), 11.86 (3H,s).

MS: m/z 1092.5 (M$^+$+23).

Reference Example 45

Synthesis of tris[4-[N-[2-(1H-indol-3-yl)acetyl]-S-[3 (N-t-butoxycarbonyl)aminopropyl]-L-cystyl]aminophenyl]methane The tris[4-[S-[3-(N-t-butoxycarbonyl)aminopropyl]-L-cyatyl]aminophenyl]methane (40 mg) obtained in Reference Example 44, 2-(1H-indol-3-yl)acetic acid (21.6 mg) and N-methylmorpholine (20.3 μl) were dissolved in N,N-dimethylformamide (0.5 ml), after which O-(7-azabenzotriazol-1-yl)-1,1,3,3-tetramethyluronium hexafluorophosphate (46.9 mg) was added under a nitrogen atmosphere at 5° C., the temperature was raised to room temperature, and the mixture was stirred for one day. The reaction mixture was poured into water and extracted with ethyl acetate (5 ml×2). The organic layer was washed with 0.1 N aqueous hydrochloric acid (5 ml), water (5 ml), saturated sodium bicarbonate water (5 ml) and saturated saline (5 ml), and then dried over sodium sulfate and concentrated to dryness. The residue was purified by silica gel column chromatography (Kiesel-gel 60, 240–400 mesh) and elution was performed with a mixed solvent of chloroform:methanol=95:5 to obtain 32.6 mg of the title compound as a light brown powder (57% yield).

The NMR data and mass spectrometry (MS) data for the obtained compound were as follows.

NMR: (270 MHz, DMSO-d6) δ: 1.36 (27H,s), 1.5–1.8 (6H,m), 2.6–3.1 (12H,m), 3.59 (6H,s), 4.5–4.7 (3H,m), 5.45 (1H,s), 6.6–7.7 (30H,m), 8.2–8.4 (3H,m), 10.13 (3H,s), 10.82 (3H,s).

MS: m/z 1563.4 (M$^+$+23).

Reference Example 46

Synthesis of tris[4-[N-[2-(thiophen-3-yl)acetyl]-S-[3 (N-t-butoxycarbonyl)aminopropyl]-L-cystyl]aminophenyl]methane Reaction was conducted in the same manner as Reference Example 45, except that 2-(thiophen-3-yl)acetic acid was used instead of 2-(1H-indol-3-yl)acetic acid, to obtain 32.6 mg of the title compound as a colorless powder (60% yield).

The NMR data and mass spectrometry (MS) data for the obtained compound were as follows.

NMR: (270 MHz, DMSO-d6) δ: 1.36 (27H,s), 1.5–1.8 (6H,m), 2.6–3.1 (12H,m), 3.51 (6H,s), 4.5–4.7 (3H,m), 5.45 (1H,s), 6.6–7.7 (24H,m), 8.4–8.6 (3H,m), 10.19 (3H,s).

MS: m/z 1464.3 (M$^+$+23).

Reference Example 47

Synthesis of tris[4-(γ-hydroxy-L-prolyl)aminophenyl]methane hydrochloride

N-t-butoxycarbonyl-γ-hydroxy-L-proline (231 mg), tris(4-aminophenyl)methane (87 mg), O-(7-azabenzotriazol-1-yl)-1,1,3,3-tetramethyluronium hexafluorophosphate (380 mg) and N-methylmorpholine (0.17 mg) were dissolved in N,N-dimethylformamide (2 ml) at 5° C., the temperature was raised to room temperature, and the mixture was stirred for 3 days. The reaction mixture was poured into water (30 ml) and shaken. This was then centrifuged, and the supernatant was removed. After adding saturated sodium bicarbonate water (30 ml) to the residue and stirring, the mixture was centrifuged and the supernatant was removed. The procedure of centrifugation and removal of the supernatant was then carried out once with saturated sodium bicarbonate water (30 ml) and twice with water (30 ml). The residue was dried under reduced pressure and dissolved in tetrahydrofuran (25 ml) at 5° C., a 4 N hydrochloric acid/1,4-dioxane solution (25 ml) was added, the temperature was raised to 10° C. and the mixture was stirred for one day. The reaction mixture was concentrated to dryness under reduced pressure to obtain 284 mg of the title compound (quantitative yield).

The mass spectrometry (MS) data for the obtained compound were as follows.

MS: m/z 629.3 (M⁺+1).

Reference Example 48

Synthesis of N-α-[2-(thiophen-3-yl)acetyl]-N-ω-(2,2,4,6,7-pentamethyl-dihydrobenzofuran-5-sulfonyl)-L-arginine N-ω-(2,2,4,6,7-pentamethyl-dihydrobenzofuran-5-sulfonyl)-L-arginine (238 mg) was suspended in dichloromethane (1.5 ml), and then N,O-bis(trimethylsilyl)acetamide (0.7 ml) was added while stirring at room temperature to prepare a solution (hereinafter referred to as Solution A). Next, 2(thiophen-3-yl)acetic acid (71 mg) and N-methylmorpholine (61 μl) were dissolved in dichloromethane (1.5 ml), isobutyloxycarbonyl chloride (72 μl) was added while stirring at −10° C., and the mixture was stirred for 15 minutes. Solution A was added dropwise thereto, the temperature was raised to room temperature, and stirring was continued for one day. Dichloromethane (2.0 ml) and 1 N hydrochloric acid (4.0 ml) were added to the reaction mixture which was then vigorously shaken, and the organic layer was separated off. The aqueous layer was again extracted with dichloromethane. After combining the organic layer and filtering through diatomaceous earth (2.0 g), the filtrate was concentrated under reduced pressure. The residue was reprecipitated with n-hexane and dichloromethane, and the residue obtained by removing the supernatant was dried under reduced pressure to obtain 294 mg of the title compound (quantitative yield).

The mass spectrometry (MS) data for the obtained compound were as follows.

MS: m/z 551.2 (M⁺+1).

Reference Example 49

Synthesis of tris[4-[N-α-[2-(thiophen-3-yl)acetyl]-N-ω-(2,2,4,6,7-pentamethyl-dihydrobenzofuran-5-sulfonyl)-L-arginyl]aminophenyl]methane The N-α-[2-(thiophen-3-yl)acetyl]-N-ω-(2,2,4,6,7-pentamethyl-dihydrobenzofuran-5-sulfonyl)-L-arginine (294 mg) obtained in Reference Example 48, tris(4-aminophenyl)methane (29 mg), O-(7-azabenzotriazol-1-yl)-1,1,3,3-tetramethyluronium hexafluorophosphate (190 mg) and N-methylmorpholine (82 μl) were dissolved in N,N-dimethylformamide (2 ml) at 5° C., the temperature was raised to room temperature, and the mixture was stirred for 3 days. The reaction mixture was poured into water (30 ml), the resulting solid was centrifuged, and the supernatant was removed. After adding saturated sodium bicarbonate water (30 mL) to the residue and stirring, the mixture was centrifuged and the supernatant was removed. The procedure of centrifugation and removal of the supernatant was then carried out once with saturated sodium bicarbonate water (30 mL) and twice with water (30 mL). The solid was dried under reduced pressure to obtain 220 mg of the title compound (quantitative yield).

The mass spectrometry (MS) data for the obtained compound were as follows.

MS: m/z 1886.4 (M⁺+1).

Reference Example 50

Synthesis of tris[4-[N-ω-(2,2,4,6,7-pentamethyl-dihydrobenzofuran-5-sulfonyl)-D-arginyl]aminophenyl]methane N-α-(9-fluorenylmethoxycarbonyl)-N-ω-(2,2,4,6,7-pentamethyl-dihydrobenzofuran-5-sulfonyl)-D-arginine (649 mg), tris(4-aminophenyl)methane (87 mg), O-(7-azabenzotriazol-1-yl)-1,1,3,3-tetramethyluronium hexafluorophosphate (380 mg) and N-methylmorpholine (0.17 ml) were dissolved in N,N-dimethylformamide (2 ml) at 5° C., the temperature was raised to room temperature, and the mixture was stirred for one day. The reaction mixture was poured into water (30 ml), the resulting solid was centrifuged, and the supernatant was removed. After adding saturated sodium bicarbonate water (30 mL) to the residue and stirring, the mixture was centrifuged and the supernatant was removed. The procedure of centrifugation and removal of the supernatant was then carried out once with saturated sodium bicarbonate water (30 mL) and twice with water (30 mL). The solid was dried under reduced pressure and then dissolved in N,N-dimethylformamide (8.0 ml) at 5° C., piperidine (2.0 ml) was added, the temperature was raised to room temperature, and the mixture was stirred for 6 hours. The reaction mixture was concentrated to dryness under reduced pressure, the residue was purified by silica gel column chromatography (Chromatorex, NH-Silica, 100–200 mesh) and elution was performed with a mixed solvent of dichloromethane:methanol=5:1 to obtain 528 mg of the title compound (quantitative yield).

The mass spectrometry (MS) data for the obtained compound were as follows.

MS: m/z 1514.7 (M⁺+1).

Reference Example 51

Synthesis of tris[4-(N-τ-trityl-D-histidyl)aminophenyl]methane

Reaction was conducted in the same manner as Reference Example 50, except that N-α-(9-fluorenylmethoxycarbonyl)-N-τ-trityl-D-histidine was used instead of N-α-(9-fluorenylmethoxycarbonyl)-N-ω-(2,2,5,7,8-pentamethyl-dihydrobenzofuran-5-sulfonyl)-D-arginine, to obtain 507 mg of the title, compound (quantitative yield).

The mass spectrometry (MS) data for the obtained compound were as follows.

MS: m/z 1428.3 (M⁺+1).

Reference Example 52

Synthesis of tris[4-(L-tryptophyl)aminophenyl]methane

Tris(4-aminophenyl)methane (145 mg), N-α-(9-fluorenylmethoxycarbonyl)-L-tryptophan.2/3 isopropyl ether (816 mg) and N-methylmorpholine (172 mg) were dissolved in N,N-dimethylformamide (3 ml), after which an N,N-dimethylformamide solution containing O-(7-azabenzotriazol-1-yl)-1,1,3,3-tetramethyluronium hexafluorophosphate (0.825 M, 2 ml) was added while cooling on ice, the temperature was raised to room temperature, and the mixture was stirred for 14 hours. The reaction-mixture was poured into water (20 mL) and shaken. This was then centrifuged, and the supernatant was removed. After adding saturated sodium bicarbonate water (20 mL) to the residue and stirring, the mixture was centrifuged and the supernatant was removed. The procedure of centrifugation and removal of the supernatant was then carried out once with saturated sodium bicarbonate water (20 mL) and twice with water (20 mL). The residue was dried under reduced pressure to obtain tris[4-[N-α-(9-fluorenylmethoxycarbonyl)-L-tryptophyl]aminophenyl]methane as a powder.

The NMR data for the obtained compound were as follows.

NMR: (270 MHz, DMSO-d6) δ: 3.0–3.2 (12H,m), 4.03.2 (3H,m), 4.4–4.6 (3H,m), 5.51 (1H,s), 6.9–8.0 (41H,m), 10.2 (3H,s), 10.9 (3H,s).

An N,N-dimethylformamide solution containing 20% (v/v) piperidine (8 mL) was added to the tris[4-[N-α-(9-fluorenylmethoxycarbonyl)-L-tryptophyl]aminophenyl]methane (the total amount obtained in the previous reaction) at room temperature, and the mixture was shaken for one hour at room temperature. The reaction mixture was concentrated under reduced pressure. Hexane (15 mL) was added to the residue, and the mixture was shaken for 30 minutes and then concentrated by centrifugation. The supernatant was removed, and the residue was concentrated to dryness under reduced pressure to obtain the title compound.

The mass spectrometry (MS) data for the obtained compound were as follows.

MS: m/z 848.4 ($M^+$+1), 1696.8 ($2M^{30}$ +1).

Reference Example 53

Synthesis of tris[4-(4-nitro-L-phenylalanyl)aminophenyl]methane

Reaction was conducted in the same manner as Reference Example 52, except that N-(9-fluorenylmethoxycarbonyl)-4-nitro-L-phenylalanine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 866.3 ($M^+$+1), 888.3 ($M^+$+23).

Reference Example 54

Synthesis of tris[4-(L-asparaginyl)aminophenyl]methane

Reaction was conducted in the same manner as Reference Example 52, except that N-(9-fluorenylmethoxycarbonyl)-L-asparagine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 632.2 ($M^+$+1), 654.3 ($M^+$+23), 1263.2 (2M++1).

Reference Example 55

Synthesis of tris(4-glycylaminophenyl)methane

Reaction was conducted in the same manner as Reference Example 52, except that N-(9-fluorenylmethoxycarbonyl)glycine was used instead of N-α-(9-fluorenylmethoxycarbonyl)-L-tryptophan.-2/3 isopropyl ether, to obtain the title compound.

The mass spectrometry (MS) data for the obtained compound were as follows.

MS: m/z 461.2 ($M^+$+1), 921.1 ($2M^+$+1).

Reference Example 56

Synthesis of tris[4-(β-methylsulfonylmethyl-L-alanyl) aminophenyl]methane

Reaction was conducted in the same manner as Reference Example 52, except that N-(9-fluorenylmethoxycarbonyl)-β-methylsulfonylmethyl-L-alanine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 779.2 ($M^+$+1), 801.3 ($M^+$+23), 1557.3 ($2M^+$+1).

Reference Example 57

Synthesis of tris[4-(L-citrullyl)aminophenyl]methane

Reaction was conducted in the same manner as Reference Example 52, except that N-α-(9-fluorenylmethoxycarbonyl)-L-citrulline was used instead of N-α-(9-fluorenylmethoxycarbonyl)-L-tryptophan.-2/3 isopropyl ether, to obtain the title compound.

The mass spectrometry (MS) data for the obtained compound were as follows.

MS: m/z 761.4 ($M^+$+1), 783.5 ($M^+$+23), 1521.7 ($2M^+$+1).

Reference Example 58

Synthesis of tris[4-[β-(pyridin-2-yl)-L-alanyl]aminophenyl]methane

Reaction was conducted in the same manner as Reference Example 52, except that N-(9-fluorenylmethoxycarbonyl)-β-(pyridin-2-yl)-L-alanine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 734.3 ($M^+$+1), 762.3 ($M^+$+23), 1467.2 ($2M^+$+1).

Reference Example 59

Synthesis of tris[4-(O-benzyl-L-seryl)aminophenyl]methane

Reaction was conducted in the same manner as Reference Example 52, except that O-benzyl-N-(9-fluorenylmethoxycarbonyl)-L-serine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 821.4 ($M^+$+1), 1642.4 ($2M^+$+1).

Reference Example 60

Synthesis of tris[4-(N-ε-acetyl-L-lysyl)aminophenyl]methane

Reaction was conducted in the same manner as Reference Example 52, except that N-ε-acetyl-N-α-(9-fluorenylmethoxycarbonyl)-L-lysine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 800.5 ($M^+$+1), 1600.6 ($2M^+$+1).

Reference Example 61

Synthesis of tris[4-(β-alanyl)aminophenyl]methane

Reaction was conducted in the same manner as Reference Example 52, except that N-(9-fluorenylmethoxycarbonyl)-

α-alanine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 503.3 ($M^++1$), 1005.3 ($2M^++1$).

Reference Example 62

Synthesis of tris[(4-(L-methionyl)aminophenyl] methane

Reaction was conducted in the same manner as Reference Example 52, except that N-(9-fluorenylmethoxycarbonyl)-L-methionine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 683.3 ($M^++1$), 1365.3 ($2M^++1$).

Reference Example 63

Synthesis of tris[4-(L-phenylalanyl)aminophenyl] methane

Reaction was conducted in the same manner as Reference Example 52, except that N-(9-fluorenylmethoxycarbonyl)-L-phenylalanine was used instead of N-α-(9-fluorenylmethoxycarbonyl)-Ltryptophan.-2/3 isopropyl ether, to obtain the title compound.

The mass spectrometry (MS) data for the obtained compound were as follows.

MS: m/z 731.4 ($M^++1$), 1461.4 ($2M^++1$).

Reference Example 64

Synthesis of tris[4-(N-τ-benzyloxymethyl-L-histidyl)aminophenyl]methane

Reaction was conducted in the same manner as Reference Example 52, except that N-τ-benzyloxymethyl-N-α-(9-fluorenylmethoxycarbonyl)-L-histidine was used instead of N-α-(9-fluorenylmethoxycarbonyl)-L-tryptophan.-2/3 isopropyl ether, to obtain the title compound.

The mass spectrometry (MS) data for the obtained compound were as follows.

MS: m/z 1061.4 ($M^++1$).

Reference Example 65

Synthesis of tris[4-(O-benzyl-L-tyrosyl) aminophenyl]methane

Reaction was conducted in the same manner as Reference Example 52, except that O-benzyl-N-(9-fluorenylmethoxycarbonyl)-L-tyrosine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 1049.5 ($M^++1$), 1071.7 ($M^++23$).

Reference Example 66

Synthesis of tris[4-(L-norleucyl)aminophenyl] methane

Reaction was conducted in the same manner as Reference Example 52, except that N-(9-fluorenylmethoxycarbonyl)-L-norleucine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 629.4 ($M^++1$), 1257.6 ($2M^++1$), 1886.6 ($3M^++1$).

Reference Example 67

Synthesis of tris[4-[N-δ-(pyrazin-2-yl)carbonyl-Lornithyl]aminophenyl]methane

Reaction was conducted in the same manner as Reference Example 52, except that N-α-(9-fluorenylmethoxycarbonyl)-N-δ-(pyrazin-2-yl)carbonyl-L-ornithine was used instead of N-α-(9-fluorenylmethoxycarbonyl)-L-tryptophan.2/3 isopropyl ether, to obtain the title compound.

Reference Example 68

Synthesis of tris[4-[β-(pyridin-4-yl)-D-alanyl] aminophenyl]methane

Reaction was conducted in the same manner as Reference Example 52, except that N-(9-fluorenylmethoxycarbonyl)-β-(pyridin-4-yl)-D-alanine was used instead of N-α-(9-fluorenylmethoxycarbonyl)-L-tryptophan.-2/3 isopropyl ether, to obtain the title compound.

Reference Example 69

Synthesis of tris[4-(L-glutaminyl)aminophenyl] methane

Reaction was conducted in the same manner as Reference Example 52, except that N-α-(9-fluorenylmethoxycarbonyl)-L-glutamine was used instead of N-α-(9-fluorenylmethoxycarbonyl)-L-tryptophan.2/3 isopropyl ether, to obtain the title compound.

Reference Example 70

Synthesis of tris[4-(L-seryl)aminophenyl]methane

Reaction was conducted in the same manner as Reference Example 52, except that N-(9-fluorenylmethoxycarbonyl)-L-serine was used instead of N-α-(9-fluorenylmethoxycarbonyl)-L-tryptophan.2/3 isopropyl ether, to obtain the title compound.

Reference Example 71

Synthesis of tris[(4-(N-δ-triphenylmethyl-L-glutaminyl) aminophenyl]methane

Reaction was conducted in the same manner as Reference Example 52, except that N-α-(9-fluorenylmethoxycarbonyl)-N-6-triphenylmethyl-L glutamine was used instead of N-α-(9-fluorenylmethoxycarbonyl)-L-tryptophan.2/3 isopropyl ether, to obtain the title compound.

The mass spectrometry (MS) data for the obtained compound were as follows.

MS: m/z 1401.6 ($M^++1$), 1423.8 ($2M^{++}1$).

Reference Example 72

Synthesis of tris[4-[β-t-butoxycarbonyl-L-alanyl] aminophenyl]methane

Reaction was conducted in the same manner as Reference Example 52, except that β-t-butoxycarbonyl-N-α-(9- fluorenylmethoxycarbonyl)-L-alanine was used instead of N-α-(9-fluorenylmethoxycarbonyl)-L-tryptophan.2/3 isopropyl ether, to obtain the title compound.

Reference Example 73

Synthesis of tris[4-[β-t-butoxycarbonylmethyl-L-alanyl]aminophenyl]methane

Reaction was conducted in the same manner as Reference Example 52, except that β-t-butoxycarbonylmethyl-N-α-(9-fluorenylmethoxycarbonyl)-L-alanine was used instead of N-α-(9-fluorenylmethoxycarbonyl)-L-tryptophan.2/3 isopropyl ether, to obtain the title compound.

Reference Example 74

Synthesis of tris[4-(β-benzyloxycarbonylamino-L-alanyl) aminophenyl]methane

Reaction was conducted in the same manner as Reference Example 52, except that β-benzyloxycarbonylamino-N-(9-fluorenylmethoxycarbonyl)-L-alanine was used instead of N-α-(9-fluorenylmethoxycarbonyl)-L-tryptophan.2/3 isopropyl ether, to obtain the title compound.

Reference Example 75

Synthesis of tris[4-(β-benzyloxycarbonylaminomethyl-L-alanyl) aminophenyl]methane hydrochloride Tris(4-aminophenyl)methane (145 mg), β-benzyloxycarbonylaminomethyl-N-t-butoxycarbonyl-L-alanine (618 mg) and N-methylmorpholine (172 mg) were dissolved in N,N-dimethylformamide (3 ml), after which an N,N-dimethylformamide solution containing O-(7-azabenzotriazol-1-yl)-1,1,3,3-tetramethyluronium hexafluorophosphate (0.825 M, 2 ml) was added while cooling on ice, the temperature was raised to room temperature, and the mixture was stirred for 14 hours. The reaction mixture was poured into water (20 mL) and shaken. This was then centrifuged, and the supernatant was removed. After adding saturated sodium bicarbonate water (20 mL) to the residue and stirring, the mixture was centrifuged and the supernatant was removed. The procedure of centrifugation and removal of the supernatant was then carried out once with saturated sodium bicarbonate water (20 mL) and twice with water (20 mL). The residue was dried under reduced pressure to obtain tris[4-(β-benzyloxycarbonylaminomethyl-N-t-butoxycarbonyl-L-alanyl)aminophenyl]methane.

The tris[4-(β-benzyloxycarbonylaminomethyl-N-t-butoxycarbonyl-L-alanyl)aminophenyl]methane (the total amount obtained in the previous reaction) was dissolved in tetrahydrofuran (4 mL), and a hydrochloric acid/dioxane solution (2 N, 4 mL) was added while cooling on ice. The mixture was raised to room temperature and stirred for 4 hours, and then concentrated under reduced pressure to obtain the title compound.

The mass spectrometry (MS) data for the obtained compound were as follows.

MS: m/z 992.4 ($M^+$+1), 1014.6 ($M^+$+23).

Reference Example 76

Synthesis of tris[4-(N-δ-benzyloxycarbonyl-L-ornithyl) aminophenyl]methane hydrochloride Reaction was conducted in the same manner as Reference Example 75, except that N-δ-benzyloxycarbonyl-N-α-t-butoxycarbonyl-L-ornithine was used instead of β-benzyloxycarbonylaminomethyl-N-t-butoxycarbonyl-L-alanine, to obtain the title compound.

The mass spectrometry (MS) data for the obtained compound were as follows.

MS: m/z 1034.5 ($M^+$+1), 1056.7 ($M^+$+23).

Reference Example 77

Synthesis of 2-(5-trifluoromethyl-1H-indol-3-yl) acetic acid

A mixture of 4-trifluoromethylphenylhydrazine (5 g), 4,4-dimethoxybutyric acid methyl ester (6 g) and 10% aqueous sulfuric acid (20 ml) was stirred for 6 hours under a nitrogen atmosphere at 90° C. The reaction mixture was allowed to cool, water was added, and then extraction was performed with ethyl acetate. The organic layer was dried over sodium sulfate and concentrated under reduced pressure. A 2 N sodium hydroxide aqueous solution (10 ml) and methanol (10 ml) were added to the obtained residue, and the mixture was heated to reflux for one hour. Water was added to the reaction mixture which was then rendered acidic with concentrated aqueous hydrochloric acid, extracted with ethyl acetate, dried over sodium sulfate, and concentrated under reduced pressure. The obtained residue was purified by silica gel column chromatography using a mixed solvent of dichloromethane, methanol, and acetic acid to obtain 0.11 g of the title compound as a colorless powder (1.5% yield).

The NMR data for the obtained compound were as follows.

NMR: (300 MHz, DMSO-d6) δ: 3.72 (2H,s), 7.37 (1H, dd), 7.43 (1H,d), 7.54 (1H,d), 7.8–8.0 (1H,m), 11.38 (1H,s), 12.0–12.4 (1H,m).

Reference Example 78

2-(5-methyl-1H-indol-3-yl)acetic acid

Reaction was conducted in the same manner as Reference Example 77, except that 4-methylphenylhydrazine hydrochloride was used instead of 4-trifluoromethylphenyl hydrazine, to obtain the title compound (69% yield).

The NMR data for the obtained compound were as follows.

NMR: (300 MHz, DMSO-d6) δ: 2.36 (3H,s), 3.59 (2H,s), 6.89 (1H,dd), 7.16 (1H,d), 7.23 (1H,d), 7.2–7.3 (1H,m), 10.75 (1H,s), 11.9–12.2 (1H,m).

Reference Example 79

2-(7-methyl-1H-indol-3-yl)acetic acid

Reaction was conducted in the same manner as Reference Example 77, except that 2-methylphenylhydrazine hydrochloride was used instead of 4-trifluoromethylphenylhydrazine, to obtain the title compound (43% yield).

The NMR data for the obtained compound were as follows.

NMR: (300 MHz, DMSO-d6) δ: 2.44 (3H,s), 3.62 (2H,s), 6.8–7.0 (2H,m), 7.21 (1H,d), 7.31 (1H,d), 10.87 (1H,s), 11.9–12.3 (1H,m).

Reference Example 80

2-(5-chloro-1H-indol-3-yl)acetic acid

Reaction was conducted in the same manner as Reference Example 77, except that 4-chlorophenylhydrazine hydrochloride was used instead of 4-trifluoromethylphenylhydrazine, to obtain the title compound (37% yield).

The NMR data for the obtained compound were as follows.

NMR: (300 MHz, DMSO-d6) δ: 3.63 (2H,s), 7.07 (1H, dd), 7.28 (1H,d), 7.36 (1H,d), 7.5–7.6 (1H,m), 11.11 (1H,s), 12.0–12.3 (1H,m).

Reference Example. 81

Synthesis of 2-(2-methyl-5-trifluoromethoxy-1H-indol-3-yl)acetic acid

A mixture of 4-trifluoromethoxyphenylhydrazine hydrochloride (1 g), levulinic acid (1.3 g) and 10% aqueous sulfuric acid (20 ml) was stirred for 6 hours under a nitrogen atmosphere at 80° C. The reaction mixture was allowed to cool, water was added, and then extraction was performed with ethyl acetate and the organic layer was concentrated under reduced pressure. Saturated sodium bicarbonate water was added to the obtained residue and vigorously stirred therewith, and then dichloromethane was added and the mixture was again vigorously stirred. The aqueous layer was collected, rendered acidic with concentrated aqueous hydrochloric acid, and then extracted with ethyl acetate. The organic layer was dried over sodium sulfate and concentrated under reduced pressure, to obtain 0.40 g of the title compound as a colorless powder (31% yield).

The NMR data for the obtained compound were as follows.

NMR: (300 MHz, DMSO-d6) δ: 2.33 (3H,s), 3.57 (2H,s), 6.94 (1H,dd), 7.2–7.4 (2H,m), 11.13 (1H,s), 11.9–12.3 (1H, M).

Reference Example 82

2-(2,5-dimethyl-1H-indol-3-yl)acetic acid

Reaction was conducted in the same manner as Reference Example 81, except that 4-methylphenylhydrazine hydrochloride was used instead of 4-trifluoromethoxyphenylhydrazine hydrochloride, to obtain the title compound (67% yield).

The NMR data for the obtained compound were as follows.

NMR: (300 MHz, DMSO-d6) δ: 2.29 (3H,s), 2.34 (3H,s), 3.51 (2H,s), 6.80 (1H,dd), 7.0–7.2 (2H,m), 11.66 (1H,s), 11.8–12.1 (1H,m).

Reference Example 83

2-(2,7-dimethyl-1H-indol-3-yl)acetic acid

Reaction was conducted in the same manner as Reference Example 81, except that 2-methylphenylhydrazine hydrochloride was used instead of 4-trifluoromethoxyphenylhydrazine hydrochloride, to obtain the title compound (7% yield).

The NMR data for the obtained compound were as follows.

NMR: (300 MHz, DMSO-d6) δ: 2.34 (3H,s), 2.41 (3H,s), 3.53 (2H,s), 6.7–6.9 (2H,m), 7.19 (1H,d), 10.68 (1H,s), 11.9–12.2 (1H,m).

Reference Example 84

2-(5-chloro-2-methyl-1H-indol-3-yl)acetic acid

Reaction was conducted in the same manner as Reference Example 81, except that 4-chlorophenylhydrazine hydrochloride was used instead of 4-trifluoromethoxyphenylhydrazine hydrochloride, to obtain the title compound (64% yield).

The NMR data for the obtained compound were as follows.

NMR: (300 MHz, DMSO-d6) δ: 2.31 (3H,s), 3.55(2H,s), 6.98 (1H,dd), 7.26 (1H,d), 7.39 (1H,d), 11.05 (1H,s), 11.8–12.2 (1H,m).

Reference Example 85

2-(2-methyl-5-isopropyl-1H-indol-3-yl)acetic acid

Reaction was conducted in the same manner as Reference Example 81, except that 4 isopropylphenylhydrazine hydrochloride was used instead of 4-trifluoromethoxyphenylhydrazine hydrochloride, to obtain the title compound (64% yield).

The NMR data for the obtained compound were as follows.

NMR: (300 MHz, DMSO-d6) δ: 1.22 (6H,d), 2.29 (3H,s), 2.8–3.0 (1H,m), 3.52 (2H,s), 6.88 (1H,dd), 7.14 (1H,d), 7.19 (1H,d), 10.66 (1H,s), 11.8–12.2 (1H,m).

Reference Example 86

Synthesis of 2-(2,6-dimethyl-1H-indol-3-yl)acetic acid

A mixture of 3-tolylhydrazine hydrochloride (1 g), levulinic acid (1.3 g) and 10% aqueous sulfuric acid (20 ml) was stirred for 6 hours under a nitrogen atmosphere at 80° C. The reaction mixture was allowed to cool, water was added, and then extraction was performed with ethyl acetate and the organic layer was concentrated under reduced pressure. Saturated sodium bicarbonate was added to the obtained residue and vigorously stirred therewith, and then dichloromethane was added and the mixture was again vigorously stirred. The aqueous layer was collected, rendered acidic with concentrated aqueous hydrochloric acid, and then extracted with ethyl acetate. The organic layer was dried over sodium sulfate and concentrated under reduced pressure. Methanol (20 ml) and concentrated sulfuric acid (1 ml) were added to the obtained residue, and the mixture was heated to reflux for 2 hours. The reaction mixture was allowed to cool, water was added, and then extraction was performed with dichloromethane. The organic layer was collected and dried over sodium sulfate, and then concentrated under reduced pressure. A 2-(2,6-dimethyl-1H-indol-3-yl)acetic acid methyl ester component was purified from the obtained residue by silica gel column chromatography using a mixed solvent of hexane and ethyl acetate. A 2 N sodium hydroxide aqueous solution (10 ml) and methanol (10 ml) were added to the obtained 2-(2,6-dimethyl-1H-indol-3-yl)acetic acid methyl ester, and the mixture was heated to reflux for one hour. The reaction mixture was allowed to cool, water was added, and then the mixture was rendered acidic with concentrated aqueous hydrochloric acid and extracted with ethyl acetate. The organic layer was collected and dried over sodium sulfate, and then concentrated under reduced pressure to obtain 0.13 g of the title compound as a colorless powder (13% yield).

The NMR data for the obtained compound were as follows.

NMR: (300 MHz, DMSO-d6) δ: 2.29 (3H,s), 2.35 (3H,s), 3.51 (2H,s), 6.52. (1H,dd), 7.02 (1H,d), 7.24 (1H,d), 10.63 (1H,s), 11.8–12.2 (1H,m).

Reference Example 87

2-(6-chloro-2-methyl-1H-indol-3-yl)acetic acid

Reaction was conducted in the same manner as Reference Example 86, except that 3-chlorophenylhydrazine hydrochloride was used instead of 3-tolylhydrazine hydrochloride, to obtain the title compound (38% yield).

The NMR data for the obtained compound were as follows.

NMR: (300 MHz, DMSO-d6) δ: 2.31 (3H,s), 3.55 (2H,s), 6.94 (1H,dd), 7.27 (1H,d), 7.37 (1H,d), 10.99 (1H,s), 11.7–12.4 (1H,m).

Reference Example 88

2-(6-methoxy-2-methyl-1H-indol-3-yl)acetic acid

Reaction was conducted in the same manner as Reference Example 86, except that 3-methoxyphenylhydrazine hydrochloride was used instead of 3-tolylhydrazine hydrochloride, to obtain the title compound (7% yield).

The NMR data for the obtained compound were as follows.

NMR: (300 MHz, DMSO-d6) δ: 2.27 (3H,s), 3.49 (2H,s), 3.73 (3H,s), 6.59 (1H,dd), 6.75 (1H,d), 7.23 (1H,d), 10.59 (1H,s), 11.7–12.2 (1H,m).

Reference Example 89

2-(2-ethyl-1H-indol-3-yl)acetic acid

Reaction was conducted in the same manner as Reference Example 86, except that phenylhydrazine hydrochloride was used instead of 3-tolylhydrazine hydrochloride and 4-oxohexanoic acid was used instead of levulinic acid, to obtain the title compound (10% yield).

The NMR data for the obtained compound were as follows.

NMR: (300 MHz, DMSO-d6) δ: 1.22 (3H,t), 2.70 (2H,q), 3.55 (2H,s), 6.8–7.1 (2H,m), 7.25 (1H,d), 7.38 (1H,d), 10.81 (1H,s), 11.8–12.2 (1H,m).

Reference Example 90

Synthesis of 2-(6-trifluoromethyl-1H-indol-3-yl) acetic acid

A mixture of 3-ethoxycarbonylamino-4-iodobenzotrifluoride (1.8 g), 2,5-dihydro-2,5-dimethoxyfuran (1.3 g), palladium acetate (60 mg), diisopropylethylamine (2.0 g), benzyltriethylammonium chloride (1.2 g) and DMF (15 ml) was stirred for 20 hours under a nitrogen atmosphere at 80° C. Water and ethyl acetate were added to the reaction mixture, the insoluble portion was filtered out with celite, and extraction was performed with ethyl acetate. The organic layer was collected and dried over sodium sulfate and then concentrated under reduced pressure. Dichloromethane (25 ml) and trifluoroacetic acid (1.5 ml) were added to the obtained residue, and the mixture was stirred at room temperature for 2 hours. Saturated sodium bicarbonate water was added to the reaction mixture and vigorously stirred therewith. The organic layer was collected and dried over sodium sulfate and then concentrated under reduced pressure. A (1-ethoxycarbonyl-6-trifluoromethyl-1H-indol-3-yl)acetic acid methyl ester component was purified from the obtained residue by silica gel column chromatography using a mixed solvent of hexane and ethyl acetate. A 2 N sodium hydroxide aqueous solution (1 ml) and methanol (1 ml) were added to the obtained (1-ethoxycarbonyl-6-trifluoromethyl-1H-indol-3-yl)acetic acid methyl ester, and the mixture was heated to reflux for one hour. Water was added to the reaction mixture, which was then rendered acidic with concentrated aqueous hydrochloric acid and extracted with ethyl acetate. The organic layer was dried over sodium sulfate and concentrated under reduced pressure, to obtain 77 mg of the title compound as a colorless powder (5% yield).

The NMR data for the obtained compound were as follows.

NMR: (300 MHz, DMSO-d6) δ: 3.70 (2H,s), 7.28 (1H, dd), 7.49 (1H,d), 7.6–7.8 (2H,m), 11.36 (1H,s), 12.1–12.3 (1H,m).

Reference Example 91

2-(4-methyl-1H-indol-3-yl)acetic acid

Reaction was conducted in the same manner as Reference Example 90, except that 1-iodo-2-ethoxycarbonylamino-6-methylbenzene was used instead of 3-ethoxycarbonylamino-4-iodobenzotrifluoride, to obtain the title compound (6% yield).

The NMR data for the obtained compound were as follows.

NMR: (300 MHz, DMSO-d6) δ: 2.55 (3H,s), 3.67 (2H,s), 6.8–7.0 (1H,m), 7.1–7.2 (2H,m), 7.23 (1H,d), 7.2–7.3 (1H, m), 10.84 (1H,s), 12.0–12.3 (1H,m).

Reference Example 92

2-(6-methyl-1H-indol-3-yl)acetic acid

Reaction was conducted in the same manner as Reference Example 90, except that 1-iodo-2-ethoxycarbonylamino-4-methylbenzene was used instead of 3-ethoxycarbonylamino-4-iodobenzotrifluoride, to obtain the title compound (58% yield).

The NMR data for the obtained compound were as follows.

NMR: (300 MHz, DMSO-d6) δ: 2.38 (3H,s), 3.59 (2H,s), 6.81 (1H,dd), 7.1–7.2 (2H,m), 7.26 (1H,d), 10.72 (1H,s), 11.9–12.3 (1H,m).

Reference Example 93

2-(6-chloro-1H-indol-3-yl)acetic acid

Reaction was conducted in the same manner as Reference Example 90, except that 1-iodo-2-ethoxycarbonylamino-4-chlorobenzene was used instead of 3-ethoxycarbonylamino-4-iodobenzotrifluoride, to obtain the title compound (38% yield).

The NMR data for the obtained compound were as follows.

NMR: (300 MHz, DMSO-d6) δ: 3.63 (2H,s), 7.00 (1H, dd), 7.28 (1H,d), 7.3–7.5 (1H,m), 7.50 (1H,d), 11.04 (1H,s), 11.8–12.2 (1H,m).

Reference Example 94

Synthesis of 2-(2-methyl-6-trifluoromethyl-1H-indol-3-yl)acetic acid

A mixture of 3-amino-4-bromobenzotrifluoride (1.2 g), levulinic acid (1.0 g), p-TsOH (0.1 g) and benzene (10 ml) was heated to reflux for 3 hours using a Dean Stark tube. The reaction mixture was concentrated under reduced pressure, and a mixture of palladium acetate (60 mg), tris(o-tolyl)phosphine (0.15 g), triethylamine (0.8 g) and DMF (2 ml) was stirred with the obtained residue in a sealed tube for 20 hours at 120° C. Water and ethyl acetate were added to the reaction mixture, the insoluble portion was filtered out with celite and extraction was performed with ethyl acetate, and then after combining the organic layer and drying over sodium sulfate, the product was concentrated under reduced pressure. Methanol (20 ml) and concentrated sulfuric acid (1 ml) were added to the obtained residue and the mixture was heated to reflux for 2 hours. Water was added to the reaction mixture, which was then extracted with dichloromethane, dried over sodium sulfate and concentrated under reduced pressure. 2-(2-methyl-6-trifluoromethyl-1H-indol-3-yl)acetic acid methyl ester was purified from the obtained residue by silica gel column chromatography using a mixed solvent of hexane and dichloromethane.

A 2 N sodium hydroxide aqueous solution (1 ml) and methanol (1 ml) were added to the obtained 2-(2-methyl-6-trifluoromethyl-1H-indol-3-yl)acetic acid methyl ester, and the mixture was heated to reflux for one hour. Water was added to the reaction mixture, which was then rendered acidic with concentrated aqueous hydrochloric acid, extracted with ethyl acetate, dried over sodium sulfate and concentrated under reduced pressure, to obtain 79 mg of the title compound as a colorless powder (6% yield).

The NMR data for the obtained compound were as follows.

NMR: (300 MHz, DMSO-d6) δ: 2.38 (3H,s), 3.62 (2H,s), 7.23 (1H,dd), 7.5–7.7 (2H,m), 11.32 (1H,s), 12.0–12.4 (1H,m).

Reference Example 95

2-(2-methyl-5-trifluoromethyl-1H-indol-3-yl)acetic acid

Reaction was conducted in the same manner as Reference Example 94, except that 4-amino-3-bromobenzotrifluoride was used instead of 3-amino-4-bromobenzotrifluoride, to obtain the title compound (8% yield).

The NMR data for the obtained compound were as follows.

NMR: (300 MHz, DMSO-d6) δ: 2.35 (3H,s), 3.63 (2H,s), 7.28 (1H,d), 7.41 (1H,dd), 7.72 (1H,d), 11.32 (1H,s), 11.8–12.3 (1H,m).

Reference Example 96

Synthesis of N-α-[2-(1H-indol-3-yl)acetyl]-N-ε-t-butoxycarbonyl-D-lysine

N-ε-t-butoxycarbonyl-D-lysine (1.54 g) was suspended in dichloromethane (10 ml) and N,O-bis(trimethylsilyl)acetamide (2.8 ml) was added while stirring at room temperature to prepare a solution (hereinafter referred to as Solution A). 2-(1H-indol-3-yl)acetic acid (998 mg) and N-methylmorpholine (687 µl) were dissolved in a mixed solvent of dichloromethane (20 ml) and N,N-dimethylformamide (10 ml), and then isobutyloxycarbonyl chloride (821 µl) was added while cooling on ice and the mixture was stirred for 15 minutes. Solution A was then added dropwise, and the mixture was stirred for one hour while cooling on ice. The reaction mixture was concentrated, the residue was poured into 1 N hydrochloric acid (100 ml), and the product was extracted twice with ethyl acetate (100 ml). The organic layer was collected, washed with saturated saline (100 ml), and then dried over magnesium sulfate. The organic layer was filtered and the filtrate was concentrated under reduced pressure. The residue was purified by silica gel column chromatography (Wakogel C-200, 75–150 µm) and elution was performed with a mixed solvent of chloroform:methanol=20:1 to obtain 1.51 g of the title compound as an oily substance (66% yield).

The NMR data for the obtained compound were as follows.

NMR: (270 MHz, DMSO-d6) δ: 1.2–1.8 (6H,m), 1.41 (9H,s), 2.8–2.9 (2H,m), 3.5–3.7 (2H,m), 4.1–4.3 (1H,m), 6.78 (1H,brs), 6.9–7.1 (2H,m), 7.20–7.23 (1H,m), 7.36 (1H,d,J=7.9 Hz), 7.57 (1H,d,J=7.8 Hz), 8.17 (1H,d,J=7.6 Hz), 10.87 (1H,brs), 12.3–12.7 (1H,brs).

Reference Example 97

Synthesis of tris(4-aminophenyl)amine

Tris(4-nitrophenyl)amine (1.9 g) was suspended in 6 N hydrochloric acid (80 ml), and then tin dichloride (31.3 g) was added at room temperature and the mixture was heated to reflux for one day. After cooling, the reaction solution was filtered, and 6 N sodium hydroxide (160 ml) was added to the filtrate while cooling on ice. The mixture was extracted twice with dichloromethane (200 mL). The organic layer was collected and dried over sodium sulfate, and then concentrated to obtain 1.44 g of the title compound as a brown powder (quantitative yield).

The NMR data and mass spectrometry (MS) data for the obtained compound were as follows.

NMR: (400 MHz, DMSO-d6) δ: 4.75 (6H,brs), 6.47 (6H,d,J=8.4 Hz), 6.62 (6H,d,J=8.4 Hz) MS: m/z 291.3 ($M^+$+1).

Example 1

Synthesis of tris[4-[N-α-[2-(1H-indol-3-yl)acetyl]-L-lysyl]aminophenyl]methane hydrochloride The tris[4-[N-α-[2-(1H-indol-3-yl)acetyl]-N-ε-t-butoxycarbonyl-L-lysyl]aminophenyl]methane (23.3 mg) obtained in Reference Example 3 was suspended in methanol (0.3 ml), a 4 N hydrochloric acid/dioxane solution (0.1 ml) was added dropwise at 5° C., the temperature was raised to room temperature, and the mixture was stirred for one day. The reaction mixture was concentrated to dryness to obtain 20.0 mg of the title compound (quantitative yield).

The NMR data and mass spectrometry (MS) data for the obtained compound were as follows.

NMR: (270 MHz, CD$_3$OD) δ: 1.1–2.0 (18H,m), 2.6–2.9 (6H,m), 3.76 (6H,ABq,J=18.6 Hz,2.1 Hz), 4.4–4.7 (3H,m), 5.42 (1H,s), 6.8–7.9 (27H,m).

MS: m/z 1145.4 ($M^+$+1).

Example 2

Synthesis of tris[4-[N-α-[2-(5-fluoro-1H-indol-3-yl)acetyl]-L-lysyl]aminophenyl]methane hydrochloride Reaction was conducted in the same manner as Example 1, except that the tris[4-[N-α-[2-(5-fluoro-1H-indol-3-yl)acetyl]-N-ε-t-butoxycarbonyl-L-lysyl]aminophenyl]methane obtained in Reference Example 4 was used instead of tris[4-[N-α-[2-(1H-indol-3-yl)acetyl]-N-ε-t-butoxycarbonyl-L-lysyl]aminophenyl]methane, to obtain 14.4 mg of the title compound (quantitative yield).

The NMR data and mass spectrometry (MS) data for the obtained compound were as follows.

NMR: (270 MHz, CD$_3$OD) δ: 1.1–2.1 (18H,m), 2.7–3.0 (6H,m), 3.6–3.9 (6H,m), 4.4–4.6 (3H,m), 5.43 (1H,s), 6.7–7.6 (24H,m).

MS: m/z 1199.5 (M$^+$+1).

Example 3

Synthesis of tris[4-[N-α-[2-(5-bromo-1H-indol-3-yl) acetyl]-L-lysyl]aminophenyl]methane hydrochloride Reaction was conducted in the same manner as Example 1, except that the tris[4-[N-α-[2-(5-bromo-1H-indol-3-yl) acetyl]-N-ε-t-butoxycarbonyl-L-lysyl]aminophenyl] methane obtained in Reference Example 5 was used instead of tris[4-[N-α-[2-(1H-indol-3-yl)acetyl]-N-ε-t-butoxycarbonyl-L-lysyl]aminophenyl]methane, to obtain 19.0 mg of the title compound (quantitative yield).

The NMR data and mass spectrometry (MS) data for the obtained compound were as follows.

NMR: (270 MHz, CD$_3$OD) δ: 1.0–2.0 (18H,m), 2.6–2.9 (6H,m), 3.6–3.8 (6H,m), 4.3–4.7 (3H,m), 5.42 (1H,s), 6.8–7.9 (24H,m).

MS: m/z 1381.2 (M$^+$+1).

Example 4

Synthesis of tris[4-[N-α-[2-(5-benzyloxy-1H-indol-3-yl)acetyl]-L-lysyl]aminophenyl]methane hydrochloride Reaction was conducted in the same manner as Example 1, except that the tris[4-[N-α-[2-(5-benzyloxy1H-indol-3-yl)acetyl]-N-ε-t-butoxycarbonyl-L-lysyl]aminophenyl] methane obtained in Reference Example 6 was used instead of tris[4-[N-α-[2-(1H-indol-3-yl)acetyl]-N-ε-t-butoxycarbonyl-L-lysyl]aminophenyl]methane, to obtain 19.0 mg of the title compound (quantitative yield).

The NMR data and mass spectrometry (MS) data for the obtained compound were as follows.

NMR: (270 MHz, CD$_3$OD) δ: 1.0–2.0 (18H,m), 2.6–2.9 (6H,m), 3.6–3.8 (6H,m), 4.4–4.6 (3H,m), 4.9–5.2 (6H,m), 5.29 (1H,s), 6.7–7.5 (39H,m).

MS: m/z 1463.5 (M$^+$+1).

Example 5

Synthesis of tris[4-[N-α-[2-(5-methoxy-1H-indol-3-yl)acetyl]-L-lysyl]aminophenyl]methane hydrochloride Reaction was conducted in the same manner as Example 1, except that the tris[4-[N-α-[2-(5-methoxy1H-indol-3-yl) acetyl]-N-ε-t-butoxycarbonyl-L-lysyl]aminophenyl] methane obtained in Reference Example 7 was used instead of tris[4-[N-α-[2-(1H-indol-3-yl)acetyl]-N-ε-t-butoxycarbonyl-L-lysyl]aminophenyl]methane, to obtain 12.3 mg of the title compound (quantitative yield).

The NMR data and mass spectrometry (MS) data for the obtained compound were as follows.

NMR: (270 MHz, CD$_3$OD) δ: 1.0–2.0 (18H,m), 2.6–2.9 (6H,m), 3.5–3.8 (6H,m), 3.74 (9H,s), 4.3–4.7 (3H,m), 5.39 (1H,s), 6.6–7.5 (24H,m).

MS: m/z 1235.6 (M$^+$+1).

Example 6

Synthesis of tris[4-[N-α-[2-(5-methoxy-2-methyl-1H-indol-3-yl)acetyl]-L-lysyl]aminophenyl]methane hydrochloride Reaction was conducted in the same manner as Example 1, except that the tris[4-[N-α-[2-(5-methoxy-2-methyl-1H-indol-3-yl)acetyl]-N-ε-t-butoxycarbonyl-L-lysyl] aminophenyl]methane obtained in Reference Example 8 was used instead of tris[4-[N-α-[2-(1H-indol-3-yl)acetyl]-N-ε-t-butoxycarbonyl-L-lysyl]aminophenyl]methane, to obtain 9.7 mg of the title compound (99% yield).

The NMR data and mass spectrometry (MS) data for the obtained compound were as follows.

NMR: (270 MHz, CD$_3$OD) δ: 1.0–2.0 (18H,m), 2.38 (9H,s), 2.6–2.9 (6H,m), 3.5–3.8 (6H,m), 3.73 (9H,s), 4.3–4.7 (3H,m), 5.39 (1H,s), 6.5–7.5 (21H,m).

MS: m/z 1277.7 (M$^+$+1).

Example 7

Synthesis of tris[4-[N-α-[2-(2-methyl-1H-indol-3-yl)acetyl]-L-lysyl]aminophenyl]methane hydrochloride Reaction was conducted in the same manner as Example 1, except that the tris[4-[N-α-[2-(2-methyl-1H-indol-3-yl) acetyl]-N-ε-t-butoxycarbonyl-L-lysyl]aminophenyl] methane obtained in Reference Example 9 was used instead of tris[4-[N-α-[2-(1H-indol-3-yl)acetyl]-N-ε-t-butoxycarbonyl-L-lysyl]aminophenyl]methane, to obtain 8.4 mg of the title compound (96% yield).

The NMR data and mass spectrometry (MS) data for the obtained compound were as follows.

NMR: (270 MHz, CD$_3$OD) δ: 1.0–2.0 (18H,m), 2.41 (9H,s), 2.6–2.9 (6H,m), 3.6–3.9 (6H,m), 4.4–4.7 (3H,m), 5.41 (1H,s), 6.6–7.9 (24H,m).

MS: m/z 1187.5 (M$^+$+1).

Example 8

Synthesis of tris[4-[N-α-[2-(2-phenyl-1H-indol-3-yl)acetyl]-L-lysyl]aminophenyl]methane hydrochloride Reaction was conducted in the same manner as Example 1, except that the tris[4-[N-α-[2-(2-phenyl-1-H-indol-3-yl) acetyl]-N-ε-t-butoxycarbonyl-L-lysyl]aminophenyl] methane obtained in Reference Example 10 was used instead of tris[4-[N-α-[2-(1H-indol-3-yl)acetyl]-N-ε-t-butoxycarbonyl-L-lysyl]aminophenyl]methane, to obtain 9.5 mg of the title compound (96% yield).

The NMR data and mass spectrometry (MS) data for the obtained compound were as follows.

NMR: (270 MHz, CD$_3$OD) δ: 1.0–2.0 (18H,m), 2.6–2.9 (6H,m), 3.7–4.0 (6H.,m), 4.4–4.7 (3H,m), 5.33 (1H,s), 6.6–7.9 (39H,m).

MS: m/z 1373.7 (M$^+$+1).

Example 9

Synthesis of tris[4-[N-α-[2-(1-methyl-1H-indol-3-yl)acetyl]-L-lysyl]aminophenyl]methane hydrochloride Reaction was conducted in the same manner as Example 1, except that the tris[4-[N-α-[2-(1-methyl-1H-indol-3-yl) acetyl]-N-ε-t-butoxycarbonyl-L-lysyl]aminophenyl] methane obtained in Reference Example 11 was used instead of tris[4-[N-α-[2-(1H-indol-3-yl)acetyl]-N-ε-t-butoxycarbonyl-L-lysyl]aminophenyl]methane, to obtain 14.7 mg of the title compound (99% yield).

The NMR data and mass spectrometry (MS) data for the obtained compound were as follows.

NMR: (270 MHz, CD$_3$OD) δ: 1.2–2.1 (18H,m), 2.6–2.9 (6H,m), 3.4–3.9 (6H,m), 3.75 (9H,s), 4.4–4.6 (3H,m), 5.45 (1H,s), 6.8–7.9 (27H,m).

MS: m/z 1187.5 (M$^+$+1).

Example 10

Synthesis of tris[4-(N-α-L-tryptophyl-L-lysyl)aminophenyl]methane hydrochloride

Reaction was conducted in the same manner as Example 1, except that the tris[4-[N-α-(N-t-butoxycarbonyl-L-tryptophyl)-N-ε-t-butoxycarbonyl-L-lysyl]aminophenyl]methane obtained in Reference Example 12 was used instead of tris[4-[N-α-[2-(1H-indol-3-yl)acetyl]-N-ε-t-butoxycarbonyl-L-lysyl]aminophenyl]methane, to obtain 20.1 mg of the title compound (quantitative yield).

The NMR data and mass spectrometry (MS) data for the obtained compound were as follows.

NMR: (270 MHz, CD$_3$OD) δ: 1.0–2.1 (18H,m), 2.8–3.1 (6H,m), 3.1–3.9 (6H,m), 4.2–4.4 (3H,m), 4.4–4.7 (3H,m), 5.54 (1H,s), 6.9–7.9 (27H,m).

MS: m/z 1232.5 (M$^+$+1).

Example 11

Synthesis of tris[4-[N-α-[3-(1H-indol-3-yl)propanoyl]L-lysyl]aminophenyl]methane hydrochloride Reaction was conducted in the same manner as Example 1, except that the tris[4-[N-α-[3-(1H-indol-3-yl)propanoyl]-N-ε-t-butoxycarbonyl-L-lysyl]aminophenyl]methane obtained in Reference Example 13 was used instead of tris[4-[N-α-[2-(1H-indol-3-yl)acetyl]-N-ε-t-butoxycarbonyl-L-lysyl]aminophenyl]methane, to obtain 9.5 mg of the title compound (98% yield).

The NMR data and mass spectrometry (MS) data for the obtained compound were as follows.

NMR: (270 MHz, CD$_3$OD) δ: 1.0–2.0 (18H,m), 2.5–3.2 (18H,m), 4.3–4.6 (3H,m), 5.46 (1H,s), 6.6–7.7 (27H,m).

MS: m/z 1187.5 (M$^+$+1).

Example 12

Synthesis of tris[4-[N-α-[4-(1H-indol-3-yl)butanoyl]-L-lysyl]aminophenyl]methane hydrochloride Reaction was conducted in the same manner as Example 1, except that the tris[4-[N-α-[4-(1H-indol-3-yl)butanoyl]-N-ε-t-butoxycarbonyl-L-lysyl]aminophenyl]methane obtained in Reference Example 14 was used instead of tris[4-[N-α-[2-(1H-indol-3-yl)acetyl]-N-ε-t-butoxycarbonyl-L-lysyl]aminophenyl]methane, to obtain 15.1 mg of the title compound (quantitative yield).

The NMR data and mass spectrometry (MS) data for the obtained compound were as follows.

NMR: (270 MHz, CD$_3$OD) δ: 1.0–2.2 (24H,m), 2.2–2.5 (6H,m), 2.6–3.1 (12H,m), 4.3–4.6 (3H,m), 5.45 (1H,s), 6.8–7.9 (27H,m).

MS: m/z 1229.5 (M$^+$+1).

Example 13

Synthesis of tris[4-[N-α-[2-(thiophen-3-yl)acetyl]-L-lysyl]aminophenyl]methane hydrochloride Reaction was conducted in the same manner as Example 1, except that the tris[4-[N-α-[2-(thiophen-3-yl)acetyl]-N-ε-t-butoxycarbonyl-L-lysyl]aminophenyl]methane obtained in Reference Example 15 was used instead of tris[4-[N-α-[2-(1H-indol-3-yl)acetyl]-N-ε-t-butoxycarbonyl-L-lysyl]aminophenyl]methane, to obtain 10.9 mg of the title compound (95% yield).

The NMR data and mass spectrometry (MS) data for the obtained compound were as follows.

NMR: (270 MHz, CD$_3$OD) δ: 1.0–2.1 (18H,m), 2.7–3.0 (6H,m), 3.4–3.9 (6H,m), 4.3–4.6 (3H,m), 5.48 (1H,s), 6.6–7.9 (21H,m).

MS: m/z 1046.3 (M$^+$+1).

Example 14

Synthesis of tris[4-[N-α-[2-(benzo[b]thiophen-3-yl)acetyl]-L-lysyl]aminophenyl]methane hydrochloride Reaction was conducted in the same manner as Example 1, except that the tris[4-[N-α-[2(benzo[b]thiophen-3-yl)acetyl]-N-ε-t-butoxycarbonyl-L-lysyl]aminophenyl]methane obtained in Reference Example 16 was used instead of tris[4-[N-α-[2-(1H-indol-3-yl)acetyl]-N-ε-t-butoxycarbonyl-L-lysyl]aminophenyl]methane, to obtain 10.7 mg of the title compound (quantitative yield).

The NMR data and mass spectrometry (MS) data for the obtained compound were as follows.

NMR: (270 MHz, CD$_3$OD) δ: 1.0–2.0 (24H,m), 2.6–3.0 (6H,m), 3.5–4.0 (6H,m), 4.4–4.7 (3H,m), 5.45 (1H,s), 6.9–8.0 (27H,m).

MS: m/z 1196.3 (M$^+$+1).

Example 15

Synthesis of tris[4-(N-α-L-phenylalanyl-L-lysyl)aminophenyl]methane hydrochloride Reaction was conducted in the same manner as Example 1, except that the tris[4-[N-α-(N-t-butoxycarbonyl-L-phenylalanyl)-N-ε-t-butoxycarbonyl-L-lysyl]aminophenyl]methane obtained in Reference Example 17 was used instead of tris[4-[N-α-[2-(1H-indol-3-yl)acetyl]-N-ε-t-butoxycarbonyl-L-lysyl]aminophenyl]methane, to obtain 9.0 mg of the title compound (99% yield).

The NMR data and mass spectrometry (MS) data for the obtained compound were as follows.

NMR: (270 MHz, CD$_3$OD) δ: 1.0–2.1 (18H,m), 2.8–3.5 (12H,m), 4.1–4.3 (3H,m), 4.4–4.7 (3H,m), 5.54 (1H,s), 6.7–7.7 (27H,m).

MS: m/Z 1115.5 (M$^+$+1).

Example 16

Synthesis of tris[4-[N-α-[2-(4-benzyloxyphenyl)acetyl]-L-lysyl]aminophenyl]methane hydrochloride Reaction was conducted in the same manner as Example 1, except that the tris[4-[N-α-[2-(4-benzyloxyphenyl)acetyl]-N-ε-t-butoxycarbonyl-L-lysyl]aminophenyl]methane obtained in Reference Example 18 was used instead of tris[4-[N-α-[2-(1H-indol-3-yl)acetyl]-N-ε-t-butoxycarbonyl-L-lysyl]aminophenyl]methane, to obtain 20.3 mg of the title compound (quantitative yield).

The NMR data and mass spectrometry (MS) data for the obtained compound were as follows.

NMR: (270 MHz, CD$_3$OD) δ: 1.0–2.1 (18H,m), 2.7–3.1 (6H,m), 3.4–3.7 (6H,m), 4.4–4.6 (3H,m), 5.02 (6H,s), 5.45 (1H,s), 6.6–7.6 (39H,m).

MS: m/z 1346.5 (M$^+$+1).

Example 17

Synthesis of tris[4-[N-α-(3-pyridylcarbonyl)-L-lysyl]aminophenyl]methane hydrochloride Reaction was conducted in the same manner as Example 1, except that the tris[4-[N-α-(3-pyridylcarbonyl)-N-ε-t-butoxycarbonyl-L-lysyl]aminophenyl]methane obtained in Reference Example 19 was used instead of tris[4-[N-α-[2-(1H-indol-3-yl)acetyl]-N-ε-t-butoxycarbonyl-L-lysyl] aminophenyl]methane, to obtain 11.3 mg of the title compound (quantitative yield).

The NMR data and mass spectrometry (MS) data for the obtained compound were as follows.

NMR: (270 MHz, CD$_3$OD) δ: 1.4–2.2 (18H,m), 2.8–3.1 (6H,m), 4.6–4.9 (3H,m), 5.49 (1H,s), 7.04 (6H,d,J=8.4 Hz), 7.53 (6H,d,J=8.4 Hz), 8.1–9.5 (12H,m).

MS: m/z 989.5 (M$^+$+1).

Example 18

Synthesis of tris[4-[N-α-[2-(5-hydroxy-1H-indol-3-yl)acetyl]-L-lysyl]aminophenyl]methane hydrochloride Reaction was conducted in the same manner as Example 1, except that the tris[4-[N-α-[2-(5-hydroxy1H-indol-3-yl)acetyl]-N-ε-t-butoxycarbonyl-L-lysyl]aminophenyl]methane obtained in Reference Example 20 was used instead of tris[4-[N-α-[2-(1H-indol-3-yl)acetyl]-N-ε-t-butoxycarbonyl-L-lysyl]aminophenyl]methane, to obtain 19.4 mg of the title compound (quantitative yield).

The NMR data and mass spectrometry (MS) data for the obtained compound were as follows.

NMR: (270 MHz, CD$_3$OD) δ: 1.0–2.1 (18H,m), 2.6–3.1 (6H,m), 3.5–3.8 (6H,m), 4.4–4.6 (3H,m), 5.42 (1H,s), 6.6–7.9 (24H,m).

MS: m/z 1193.6 (M$^+$+1).

Example 19

Synthesis of tris[4-[N-α-[2-(4-hydroxyphenyl)acetyl]-L-lysyl]aminophenyl]methane hydrochloride Reaction was conducted in the same manner as Example 1, except that the tris[4-[N-α-[2-(4-hydroxyphenyl)acetyl]-N-ε-t-butoxycarbonyl-L-lysyl]aminophenyl]methane obtained in Reference Example 21 was used instead of tris[4-[N-α-[2-(1H-indol-3-yl)acetyl]-N-ε-t-butoxycarbonyl-L-lysyl]aminophenyl]methane, to obtain 12.3 mg of the title compound (quantitative yield).

The NMR data and mass spectrometry (MS) data for the obtained compound were as follows.

NMR: (270 MHz, CD$_3$OD) δ: 1.0–2.1 (18H,m), 2.7–3.1 (6H,m), 3.3–3.9 (6H,m), 4.4–4.6 (3H,m), 5.46 (1H,s), 6.6–7.7 (24H,m).

MS: m/z 1076.4 (M$^+$+1).

Example 20

Synthesis of tris[4-[N-α-[2-(2-tolyl)acetyl]-L-lysyl]aminophenyl]methane hydrochloride The tris[4-[N-α-[2-(2-tolyl)acetyl]-N-α-t-butoxycarbonyl-L-lysyl]aminophenyl]methane (58 mg) obtained in Reference Example 23 was suspended in tetrahydrofuran (12 ml), a 4 N hydrochloric acid/dioxane solution (12 ml) was added at 0° C., and the mixture was stirred for one day. The reaction mixture was concentrated to dryness to obtain 35 mg of the title compound (70% yield).

The mass spectrometry (MS) data and thin-layer chromatography (TLC) data for the obtained compound were as follows.

MS: m/z 1071 (M$^+$+1).

Rf value (NH TLC, developing solvent; dichloromethane:methanol=5:1): 0.4.

Example 21

Synthesis of tris[4-[N-α-[2-(2-methyl-1H-indol-3-yl)acetyl]-D-lysyl]aminophenyl]methane The tris[4-[N-α-[2-(2-methyl-1H-indol-3-yl)acetyl]-N-ε-benzyloxycarbonyl-D-lysyl]aminophenyl]methane (19 mg) obtained in Reference Example 26 was dissolved in N,N-dimethylformamide (0.5 ml), 10%-Pd/C (30.0 mg) was added thereto, and then the mixture was stirred for 3 days at room temperature under a hydrogen atmosphere. The reaction mixture was filtered with celite, the filtrate was concentrated and exsiccated, and the residue was washed with diethyl ether and dried under reduced pressure to obtain 8.0 mg of the title compound (56% yield).

The NMR data and mass spectrometry (MS) data for the obtained compound were as follows.

NMR: (270 MHz, CD$_3$OD) δ: 1.1–2.0 (18H,m), 2.42 (9H,s), 2.6–2.9 (6H,m), 3.6–3.9 (6H,m), 4.4–4.7 (3H,m), 5.46 (1H,s), 6.8–8.0 (24H,m).

MS: m/z 1187.8 (M$^+$+1).

Example 22

Synthesis of tris[4-[N-α-[2-(5-methoxy-2-methyl-1-H-indol-3-yl)acetyl]-D-lysyl]aminophenyl]methane hydrochloride The tris[4-[N-α-[2-(5-methoxy-2-methyl-1H-indol-3-yl)acetyl]-N-ε-t-butoxycarbonyl-D-lysyl]aminophenyl]methane (330.5 mg) obtained in Reference Example 29 was dissolved in methanol (3 ml), a 4 N hydrochloric acid/dioxane solution (1 ml) was added dropwise at 5° C., the temperature was raised to room temperature, and the mixture was stirred for 10 hours. The reaction mixture was concentrated to dryness, the residue was purified by preparative HPLC (YMC HPLC column: Combi Prep. Pro C18, 50×20 mm I.D.), and elution was performed with a mixed solvent of distilled water:acetonitrile=95:5–0:100. The obtained fraction was concentrated to dryness, and the residue was dissolved in methanol (10 ml), 1 N aqueous hydrochloric acid (0.26 ml) was added, and the mixture was stirred and then concentrated to dryness. Diethyl ether (5 ml) was added to the residue prior to trituration and the supernatant was decanted, after which the residue was dried under reduced pressure to obtain 105.2 mg of the title compound as a light violet powder (36% yield).

The NMR data and mass spectrometry (MS) data for the obtained compound were as follows.

NMR: (270 MHz, CD$_3$OD) δ: 1.0–2.0 (18H,m), 2.40 (9H,s), 2.6–2.9 (6H,m), 3.5–3.8 (6H,m), 3.74 (9H,s), 4.4–4.7 (3H,m), 5.43 (1H,s), 6.5–7.5 (21H,m).

MS: m/z 1277.7 (M$^+$+1).

Example 23

Synthesis of tris[4-[N-α-[2-(thiophen-3-yl)acetyl]-D-lysyl]aminophenyl]methane hydrochloride The tris[4-(N-ε-t-butoxycarbonyl-D-lysyl)aminophenyl]methane (30 mg) obtained in Reference Example 28, 2-(thiophen-3-yl)acetic acid (22 mg) and 4-dimethylaminopyridine (0.4 mg) were dissolved in a mixed solvent of dichloromethane (0.8 ml) and N,N-dimethylformamide (0.2 ml), after which 1-ethyl-3-(3-dimethylaminopropyl)carbbdiimide hydrochloride (30 mg) was added under a nitrogen atmosphere at 5° C., the temperature was raised to room temperature, and the mixture was stirred for 18 hours. The reaction mixture was poured into saturated sodium bicarbonate water (10 ml) and the product was extracted twice with ethyl acetate (10 ml). After combining the organic layer and washing with saturated saline (10 ml), drying was performed over magnesium sulfate. The organic layer was filtered and the filtrate was concentrated under reduced pressure. The precipitated solid was washed with ethyl acetate (10 ml) to obtain 25 mg of tris[4-[N-ε-t-butoxycarbonyl-N-α-[2-(thiophen-3-yl)acetyl]-D-lysyl]aminophenyl]methane.

The tris[4-[N-ε-t-butoxycarbonyl-N-α-[2-(thiophen3-yl)acetyl]-D-lysyl]aminophenyl]methane (25 mg) was suspended in tetrahydrofuran (1 ml), a 4 N hydrochloric acid/dioxane solution (1 ml) was added dropwise while cooling on ice, and the mixture was allowed to stand for 2 days at 5° C. The reaction mixture was concentrated under reduced pressure, and the residue was washed with methanol (10 ml) and ethyl acetate (20 ml). The residue was dried under reduced pressure to obtain 12.7 mg of the title compound (37% yield).

The NMR data and mass spectrometry (MS) data for the obtained compound were as follows.

NMR: (270 MHz, DMSO-d6) δ: 1.2–1.8 (18H,m), 2.72.8 (6H,m), 3.52 (6H,s), 4.4–4.7 (3H,m), 5.44 (1H,s), 6.9–7.1 (12H,m), 7.26 (3H,s), 7.4–7.5 (3H,m), 7.53 (6H,d,J=8.4 Hz), 7.93 (6H,brs), 8.41 (3H,d,J=8.2 Hz), 10.15 (3H,s).

MS: m/z 1046.5 (M$^+$+1).

Example 24

Synthesis of tris[4-[N-α-[2-(pyridin-3-yl)acetyl]-L-lysyl]aminophenyl]methane hydrochloride Reaction was conducted in the same manner as Example 1, except that the tris[4-[N-α-[2-(pyridin-3-yl)acetyl]-N-ε-t-butoxycarbonyl-L-lysyl]aminophenyl]methane obtained in Reference Example 30 was used instead of tris[4-[N-α-[2-(1H-indol-3-yl)acetyl]-N-ε-t-butoxycarbonyl-L-lysyl] aminophenyl]methane, to obtain 14.4 mg of the title compound (quantitative yield).

The NMR data and mass spectrometry (MS) data for the obtained compound were as follows.

NMR: (270 MHz, CD$_3$OD) δ: 1.4–2.1 (18H,m), 2.8–3.1 (6H,m), 3.8–4.1 (6H,m), 4.3–4.6 (3H,m), 5.47 (1H,s), 6.8–9.0 (24H,m).

MS: m/z 1031.6 (M$^+$+1).

Example 25

Synthesis of tris[4-[N-[N-α-[2-(1H-indol-3-yl)acetyl]L-lysyl]-N-methyl]aminophenyl]methane hydrochloride The tris[4-[N-[N-α-[2-(1H-indol-3-yl)acetyl]-N-ebenzyloxycarbonyl-L-lysyl]-N-methyl]aminophenyl]methane (42.7 mg) obtained in Reference Example 37 was dissolved in methanol (2 ml), 10% palladium-Pd/C (20 mg) and 1 N aqueous hydrochloric acid (80 μl) were added under a nitrogen atmosphere, and the mixture was stirred for 17 hours at room temperature under a hydrogen atmosphere. The reaction mixture was filtered with celite and the filtrate was concentrated and exsiccated to obtain 37.6 mg of the title compound as a colorless powder (86% yield).

The NMR data and mass spectrometry (MS) data for the obtained compound were as follows.

NMR: (270 MHz, CD$_3$OD) δ: 0.8–1.7 (18H,m), 2.6–2.9 (6H,m), 3.20 (9H,s), 3.64 (6H,s), 4.4–4.6 (3H,m), 5.59 (1H,s), 6.8–7.7 (27H,m).

MS: m/z 1187.7 (M$^+$+1).

Example 26

Synthesis of tris[4-[N-[N-α-[2-(1H-indol-3-yl) acetyl]D-lysyl]-N-methyl]aminophenyl]methane hydrochloride Reaction was conducted in the same manner as Example 25, except that the tris[4-[N-[N-α-[2-(1-H-indol-3-yl)acetyl]-N-ε-benzyloxycarbonyl-D-lysyl]-N-methyl] aminophenyl]methane obtained in Reference Example 38 was used instead of tris[4-[N-[N-α-[2-(1H-indol-3-yl)acetyl]-N-ε-benzyloxycarbonyl-L-lysyl]-N-methyl] aminophenyl]methane, to obtain 25.2 mg of the title compound as light orange crystals (88% yield).

The NMR data and mass spectrometry (MS) data for the obtained compound were as follows.

NMR: (270 MHz, CD$_3$OD) δ: 0.8–1.7 (18H,m), 2.4–2.9 (6H,m), 3.21 (9H,s), 3.65 (6H,s), 4.4–4.6 (3H,m), 5.64 (1H,s), 6.8–8.0 (27H,m).

MS: m/z 1187.6 (M$^+$+1).

Example 27

Synthesis of tris[4-[N-[N-α-[2-(5-methoxy-2-methyl-1H-indol-3-yl)acetyl]-L-lysyl]-N-methyl] aminophenyl]methane hydrochloride Reaction was conducted in the same manner as Example 25, except that the tris[4-[N-[N-α-[2-(5-methoxy-2-methyl-1H-indol-3-yl)acetyl]-N-ε-benzyloxycarbonyl-L-lysyl]-N-methyl]aminophenyl]methane obtained in Reference Example 39 was used instead of tris[4-[N-[N-α-[2-(1H-indol-3-yl) acetyl]-N-ε-benzyloxycarbonyl-L-lysyl]-N-methyl]aminophenyl]methane, to obtain 29.9 mg of the title compound as a colorless powder (92% yield).

The NMR data and mass spectrometry (MS) data for the obtained compound were as follows.

NMR: (270 MHz, CD$_3$OD) δ: 0.8–1.8 (18H,m), 2.34 (9H,s), 2.5–2.7 (6H,m), 3.19 (9H,s), 3.55 (6H,s), 3.77 (9H, s), 4.4–4.6 (3H,m), 5.59 (1H,s), 6.5–7.5 (21H,m).

MS: m/z 1319.8 (M$^+$+1).

Example 28

Synthesis of tris[4-[N-[N-α-[2-(5-methoxy-2-methyl-1H-indol-3-yl)acetyl]-D-lysyl]-N-methyl] aminophenyl]methane hydrochloride Reaction was conducted in the same manner as Example 25, except that the tris[4-[N-[N-α-[2-(5-methoxy-2-methyl-1H-indol-3-yl)acetyl]-N-ε-benzyloxycarbonyl-D-lysyl]-N-methyl]aminophenyl]methane obtained in Reference Example 40 was used instead of tris[4-[N-[N-α-[2-(1H-indol-3-yl) acetyl]-N-ε-benzyloxycarbonyl-L-lysyl]-N-methyl]aminophenyl]methane, to obtain 29.8 mg of the title compound as a colorless powder (85% yield).

The NMR data and mass spectrometry (MS) data for the obtained compound were as follows.

NMR: (270 MHz, CD$_3$OD) δ: 0.8–1.8 (18H,m), 2.34 (9H,s), 2.5–2.7 (6H,m), 3.20 (9H,s), 3.56 (6H,s), 3.77 (9H, s), 4.4–4.6 (3H,m), 5.59 (1H,s), 6.5–7.5 (21H,m).

MS: m/z 1319.7 (M$^+$+1).

Example 29

Synthesis of tris[4-[N-α-[2-(1H-indol-3-yl)acetyl]-N-εdimethyl-L-lysyl]aminophenyl]methane The tris[4-[N-ε-dimethyl-L-lysyl]aminophenyl]methane obtained in Reference Example 42, 2-(1H-indol-3-yl)acetic acid (12.4 mg) and N-methylmorpholine (11.5 μl) were dissolved in N,N-dimethylformamide (0.2 ml), after which O-(7-azabenzotriazol-1-yl)-1,1,3,3-tetramethyluronium hexafluorophosphate (26.9 mg) was added under a nitrogen atmosphere at 5° C., the temperature was raised to room temperature, and the mixture was stirred for 3 hours. The reaction mixture was poured into water (5 ml), ethyl acetate (5 ml) was added and the mixture was vigorously stirred. The precipitated crystals were filtered, washed with ethyl acetate (1 ml×3) and then dried to obtain 14.3 mg of the title compound as a light yellow powder (66% yield).

The NMR data and mass spectrometry (MS) data for the obtained compound were as follows.

NMR: (270 MHz, DMSO-d6) δ: 1.1–1.9 (18H,m), 2.66 (18H,s), 2.7–3.0 (6H,m), 3.60 (6H,ABq,J=20.1 Hz,5.1 Hz), 4.3–4.6 (3H,m), 5.43 (1H,s), 6.8–7.7 (27H,m), 8.0–8.3 (3H, m), 10.06 (3H,s), 10.85 (3H,s).

MS: m/z 1229.7 (M$^+$+1).

Example 30

Synthesis of tris[4-[N-α-[2-(2-methyl-1H-indol-3-yl)acetyl]-N-ε-dimethyl-L-lysyl]aminophenyl] methane Reaction was conducted in the same manner as Example 29, except that 2-(2-methyl-1H-indol-3-yl)acetic acid was used instead of 2-(1H-indol-3-yl)acetic acid, to obtain 21.5 mg of the title compound as a light yellow powder (93% yield).

The NMR data and mass spectrometry (MS) data for the obtained compound were as follows.

NMR: (270 MHz, DMSO-d6) δ: 1.1–1.9 (18H,m), 2.34 (9H,s), 2.68 (18H,s), 2.7–3.0 (6H,m), 3.52 (6H,ABq,J=23.3 Hz,8.2 Hz), 4.3–4.6 (3H,m), 5.43 (1H,s), 6.8–7.7 (24H,m), 8.0–8.3 (3H,m), 9.97 (3H,s), 10.75 (3H,s).

MS: m/z 1271.9 (M$^+$+1).

Example 31

Synthesis of tris[4-[(N-α-[2-(5-methoxy-2-methyl-1H-indol-3-yl)acetyl]-N-ε-dimethyl-L-lysyl]aminophenyl]methane Reaction was conducted in the same manner as Example 29, except that 2-(5-methoxy-2-methyl-1H-indol3-yl)acetic acid was used instead of 2-(1H-indol-3-yl)acetic acid, to obtain 18.6 mg of the title compound as a light yellow powder (81% yield).

The NMR data and mass spectrometry (MS) data for the obtained compound were as follows.

NMR: (270 MHz, DMSO-d6) δ: 1.1–1.9 (18H,m), 2.32 (9H,s), 2.66 (18H,s), 2.7–3.0 (6H,m), 3.3–3.6 (6H,m), 3.71 (9H,s), 4.3–4.6 (3H,m), 5.43 (1H,s), 6.5–7.7 (21H,m), 8.0–8.2 (3H,m), 9.98 (3H,s), 10.56 (3H,s).

MS: m/z 1361.8 (M$^+$+1).

Example 32

Synthesis of tris[4-[N-α-[2-(thiophen-3-yl)acetyl]-N-ε-dimethyl-L-lysyl]aminophenyl]methane Reaction was conducted in the same manner as Example 29, except that 2-(thiophen-3-yl)acetic acid was used instead of 2-(1H-indol-3-yl)acetic acid, to obtain 19.0 mg of the title compound as a light yellow powder (96% yield).

The NMR data and mass spectrometry (MS) data for the obtained compound were as follows.

NMR: (270 MHz, DMSO-d6) δ: 1.1–1.9 (18H,m), 2.64 (18H,s), 2.7–3.0 (6H,m), 3.3–3.6 (6H,m), 4.3–4.6 (3H,m), 5.44 (1H,s), 6.9–7.7 (21H,m), 8.2–8.5 (3H,m), 10.05 (3H,s).

MS: m/z 1130.7 (M$^+$+1).

Example 33

Synthesis of tris[4-[N-[2-(1H-indol-3-yl)acetyl]-S-(3-aminopropyl)-L-cystyl]aminophenyl]methane hydrochloride The tris[4-[N-[2-(1H-indol-3-yl)acetyl]-S-(3-(N-tbutoxycarbonyl)aminopropy)-L-cystyl]aminophenyl] methane (20.9 mg) obtained in Reference Example 45 was dissolved in tetrahydrofuran (1 ml), a 4 N hydrochloric acid/dioxane solution (1 ml) was added at room temperature and the mixture was stirred for 7 hours. The reaction mixture was concentrated to dryness and the residue was washed with diethyl ether (1 ml×3) to obtain 18.4 mg of the title compound as a light brown powder (quantitative yield).

The NMR data and mass spectrometry (MS) data for the obtained compound were as follows.

NMR: (270 MHz, DMSO-d6) δ: 1.6–2.0 (6H,m), 2.5–3.0 (18H,m), 3.5–3.9 (6H,m), 4.5–4.8 (3H,m), 5.45 (1H,s), 6.8–8.2 (36H,m), 8.3–8.5 (3H,m), 10.20 (3H,s), 10.85 (3H, s).

MS: m/z 1241.4 (M$^+$+1).

Example 34

Synthesis of tris[4-[N-[2-(thiophen-3-yl)acetyl]-S-(3-aminopropyl)-L-cystyl]aminophenyl]methane hydrochloride Reaction was conducted in the same manner as Example 33, except that the tris[4-[N-[2-(thiophen-3-yl)acetyl]-S-[3-(N-t-butoxycarbonyl)aminopropyl]-L-cystyl]aminophenyl] methane obtained in Reference Example 46 was used instead of tris[4-[N-[2-(1H-indol3-yl)acetyl]-S-[3-(N-t-butoxycarbonyl)aminopropyl]-L-cystyl]aminophenyl] methane, to obtain 17.7 mg of the title compound as a light violet powder (quantitative yield).

The NMR data and mass spectrometry (MS) data for the obtained compound were as follows.

NMR: (270 MHz, DMSO-d6) δ: 1.6–2.0 (6H,m), 2.5–3.1 (18H,m), 3.5–3.9 (6H,m), 4.5–4.8 (3H,m), 5.45 (1H,s), 6.8–8.2 (30H,m), 8.4–8.7 (3H,m), 10.29 (3H,s).

MS: m/z 1142.3 (M$^+$+1).

Example 35

Synthesis of tris[4-[N-[2-(1H-indol-3-yl)acetyl]-γ-hydroxy-L-prolyl]aminophenyl]methane The tris[4-(γ-hydroxy-L-prolyl)aminophenyl]methane hydrochloride (71 mg) obtained in Reference Example 47 and N-methylmorpholine (35 μl) were suspended in N,N-dimethylformamide (2.0 ml), and then the suspension was added to a mixture of 2-(1H-indol-3-yl)acetic acid (58 mg), 1-hydroxybenzotriazole monohydrate (25 mg) and 1-ethyl-3-(3-dimethylaminopropyl) carbodiimide hydrochloride (70 mg) at 5° C., the temperature was raised to room temperature, and the mixture was stirred for one day. The reaction mixture was purified by high performance liquid chromatography using methanol/trifluoroacetic acid (100/0.1) and water/trifluoroacetic acid (100/0.1) as a mixed eluent, to obtain 8.2 mg of the title compound (10% yield).

The mass spectrometry (MS) data for the obtained compound were as follows.

MS: m/z 1100.1 (M$^+$+1).

Example 36

Synthesis of tris[4-[N-[2-(thiophen-3-yl)acetyl]-γ-hydroxy-L-prolyl]aminophenyl]methane Reaction was conducted in the same manner as Example 35, except that 2-(thiophen-3-yl)acetic acid was used instead of 2-(1H-indol-3-yl)acetic acid, to obtain 22 mg of the title compound (30% yield).

The mass spectrometry (MS) data for the obtained compound were as follows.

MS: m/z 1101.1 (M$^+$+1).

Example 37

Synthesis of tris[4-[N-(pyridine-3-carbonyl)-γ-hydroxy-L-prolyl]aminophenyl]methane hydrochloride Reaction was conducted in the same manner as Example 35, except that nicotinic acid was used instead of 2-(1H-indol-3-yl)acetic acid, to obtain 8.7 mg of a trifluoroacetic acid salt of the title compound. This was dissolved in methanol (2.0 ml), concentrated hydrochloric acid (6 μl) was added at 5° C., and the mixture was stirred for 10 minutes. The reaction mixture was concentrated to dryness to obtain 7.1 mg of the title compound (9.0% yield).

The mass spectrometry (MS) data for the obtained compound were as follows.

MS: m/z 944.3 (M$^+$+1).

Example 38

Synthesis of tris[4-[N-α-[2-(thiophen-3-yl)acetyl]-L-arginyl]aminophenyl]methane hydrochloride The tris[4-[N-α-[2-(thiophen-3-yl)acetyl]-N-ω-(2,2,4,6,7-pentamethyl-dihydrobenzofuran-5-sulfonyl)-L-arginyl]aminophenyl]methane (150 mg) obtained in Reference Example 49 was suspended in dichloromethane (6.0 ml), trifluoroacetic acid (6.0 ml) was added at 5° C., the temperature was raised to room temperature, and the mixture was stirred for one hour. After adding 1,2-dichloroethane (30 ml) to the reaction mixture, it was concentrated to dryness and purified by high performance liquid chromatography using methanol/trifluoroacetic acid (100/0.1) and water/trifluoroacetic acid (100/0.1) as a mixed eluent. A portion thereof was dissolved in methanol (3.0 ml), concentrated hydrochloric acid (5 μl) was added at 5° C., and the mixture was stirred for 10 minutes. The reaction mixture was concentrated to dryness to obtain 3.3 mg of the title compound.

The NMR data and mass spectrometry (MS) data for the obtained compound were as follows.

NMR: (270 MHz, CD$_3$OD, measured as trifluoroacetate) δ: 1.5–2.1 (15H,m), 3.0–3.3 (12H,m), 3.5–3.8 (6H,m), 4.4–4.6 (3H,m), 5.5 (1H,s), 6.9–7.6 (27H,m).

MS: m/z 1130.6 (M$^+$+1).

Example 39

Synthesis of tris[4-[N-α-[2-(2-methyl-1H-indol-3-yl)acetyl]-D-arginyl]aminophenyl]methane hydrochloride The tris[4-[N-ω-(2,2,4,6,7-pentamethyl-dihydrobenzofuran-5-sulfonyl)-D-arginyl]aminophenyl]methane (176 mg) obtained in Reference Example 50, 2-(2-methyl-1H-indol-3-yl)acetic acid (79 mg), O-(7-azabenzotriazol-1-yl)-1,1,3,3-tetramethyluronium hexafluorophosphate (171 mg) and N-methylmorpholine (66 μl) were dissolved in N,N-dimethylformamide (1.5 ml) at 5° C., the temperature was raised to room temperature, and the mixture was stirred for one day. The reaction mixture was poured into water (30 ml) and centrifuged, and the supernatant was removed. After adding saturated sodium bicarbonate water (30 ml) to the residue and stirring, the mixture was centrifuged and the supernatant was removed. The procedure of centrifugation and removal of the supernatant was then carried out once with saturated sodium bicarbonate water (30 ml) and twice with water (30 ml). The residue was dried under reduced pressure and suspended in 1,2-dichloroethane (6.0 ml), and then trifluoroacetic acid (6.0 ml) was added at 5° C., the temperature was raised to room temperature, and the mixture was stirred for one hour. After adding 1,2-dichloroethane (12 ml) to the reaction mixture, it was concentrated to dryness and a portion thereof was purified by high performance liquid chromatography using methanol/trifluoroacetic acid (100/0.1) and water/trifluoroacetic acid (100/0.1) as a mixed eluent. After dissolution in methanol (0.5 ml), an excess of 0.5 N hydrochloric acid was added and the mixture was concentrated under reduced pressure to obtain 4.2 mg of the title compound.

The NMR data and mass spectrometry (MS) data for the obtained compound were as follows.

NMR: (400 MHz, CD$_3$OD) δ: 1.4–1.9 (15H,m), 2.4 (9H,s), 3.0–3.2 (6H,m), 3.6–3.7 (6H,m), 4.5–4.6 (3H,m), 5.5 (1H,s), 6.9–7.5 (30H,m).

MS: m/z 636.5 (M$^+$/2+1).

Example 40

Synthesis of tris[4-[N-α-[2-(thiophen-3-yl)acetyl]-D-arginyl]aminophenyl]methane hydrochloride Reaction was conducted in the same manner as Example 39, except that 2-(thiophen-3-yl)acetic acid was used instead of 2-(2-methyl-1H-indol-3-yl)acetic acid, to obtain 3.1 mg of the title compound.

MS: m/z 565.8 (M$^+$/2+1), 1130.6 (M$^+$+1).

Example 41

Synthesis of tris[4-[N-α-[2-(thiophen-3-yl)acetyl]-D-histidyl]aminophenyl]methane trifluoroacetate The tris[4-(N-τ-trityl-D-histidyl)aminophenyl]methane (176 mg) obtained in Reference Example 51, 2-(thiophen-3-yl)acetic acid (64 mg), O-(7-azabenzotriazol-1-yl)-1,1,3,3-tetramethyluronium hexafluorophosphate (171 mg) and N-methylmorpholine (66 μl) were dissolved in N,N- dimethylformamide (1.5 ml) at 5° C., the temperature was raised to room temperature, and the mixture was stirred for one day. The reaction mixture was poured into water (30 ml) and centrifuged, and the supernatant was removed. After adding saturated sodium bicarbonate water (30 ml) to the residue and stirring, the mixture was centrifuged and the supernatant was removed. The procedure of centrifugation and removal of the supernatant was then carried out once with saturated sodium bicarbonate water (30 ml) and twice with water (30 ml). The residue was dried under reduced pressure and suspended in 1,2-dichloroethane (6.0 ml), and then trifluoroacetic acid (6.0 ml) was added at 5° C., the temperature was raised to room temperature, and the mixture was stirred for 4 hours. After adding 1,2-dichloroethane (12 ml) to the reaction mixture, it was concentrated to dryness and purified by high performance liquid chromatography using methanol/trifluoroacetic acid (100/0.1) and water/trifluoroacetic acid (100/0.1) as a mixed eluent, to obtain 4.8 mg of the title compound (3.4% yield).

The mass spectrometry (MS) data for the obtained compound were as follows.

MS: m/z 1073.3 (M$^+$+1).

Example 42

Synthesis of tris[4-[N-α-[2-(1H-indol-3-yl)acetyl]-L-tryptophyl]aminophenyl]methane The tris[4-(L-tryptophyl)aminophenyl]methane obtained in Reference Example 52 (1/5 of the total amount obtained in Reference Example 52), 2-(1H-indol-3-yl)acetic acid (53 mg) and N-methylmorpholine (31 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 14 hours. The reaction mixture was poured into water (8 ml) and $^1$75 shaken. This was then centrifuged, and the supernatant was removed. After adding saturated sodium bicarbonate water (8 ml) to the residue and stirring, the mixture was centrifuged and the supernatant was removed. The procedure of centrifugation and removal of the supernatant was then carried out once with saturated sodium bicarbonate water (8 ml) and twice with water (8 ml). The residue was dried under reduced pressure. A portion thereof was purified by preparative high performance liquid chromatography using methanol/trifluoroacetic acid (100/0.1) and water/trifluoroacetic acid (100/0.1) as a mixed eluent, to obtain 2.6 mg of the title compound.

The mass spectrometry (MS) data for the obtained compound were as follows.

MS: m/z 1319.1 (M$^+$+1), 1341.6 (M$^+$+23).

Example 43

Synthesis of tris[4-[N-α-[2-(2-methyl-1H-indol-3-yl)acetyl]-L-tryptophyl]aminophenyl]methane The tris[4-(L-tryptophyl)aminophenyl]methane obtained in Reference Example 52 (1/5 of the total amount obtained in Reference Example 52), 2-(2-methy-1H-indol-3-yl)acetic acid (57 mg) and N-methylmorpholine (31 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 14 hours. The reaction mixture was poured into water (8 ml) and shaken. This was then centrifuged, and the supernatant was removed. After adding saturated sodium bicarbonate water (8 ml) to the residue and stirring, the mixture was centrifuged and the supernatant was removed. The procedure of centrifugation and removal of the supernatant was then carried out once with saturated sodium bicarbonate water (8 ml) and twice with water (8 ml). The residue was dried under reduced pressure. A portion thereof was purified by preparative high performance liquid chromatography using methanol/trifluoroacetic acid (100/0.1) and water/trifluoroacetic acid (100/0.1) as a mixed eluent, to obtain 2.5 mg of the title compound.

The mass spectrometry (MS) data for the obtained compound were as follows.

MS: m/z 1362.1 (M$^+$+1), 1383.7 (M$^+$+23).

Example 44

Synthesis of tris[4-[N-α-[2-(5-methoxy-2-methyl-1-H-indol-3-yl)acetyl]-L-tryptophyl]aminophenyl]methane The tris[4-(L-tryptophyl)aminophenyl]methane obtained in Reference Example 52 (1/5 of the total amount obtained in Reference Example 52), 2-(5-methoxy-2-methyl-1H-indol-3-yl)acetic acid (66 mg) and N-methylmorpholine (31 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 14 hours. The reaction mixture was poured into water (8 ml) and shaken. This was then centrifuged, and the supernatant was removed. After adding saturated sodium bicarbonate water (8 ml) to the residue and stirring, the mixture was centrifuged and the supernatant was removed. The procedure of centrifugation and removal of the supernatant was then carried out once with saturated sodium bicarbonate water (8 ml) and twice with water (B ml). The residue was dried under reduced pressure. A portion thereof was purified by preparative high performance liquid chromatography using methanol/trifluoroacetic acid (100/0.1) and water/trifluoroacetic acid (100/0.1) as a mixed eluent, to obtain 2.9 mg of the title compound.

The mass spectrometry (MS) data for the obtained compound were as follows.

MS: m/z 1452.3 (M$^+$+1), 1474.6 (M$^+$+23).

Example 45

Synthesis of tris[4-[N-α-[2-(thiophen-3-yl)acetyl]-L-tryptophyl]aminophenyl]methane The tris[4-(L-tryptophyl)aminophenyl]methane obtained in Reference Example 52 (1/5 of the total amount obtained in Reference Example 52), 2-(thiophen-3-yl)acetic acid (43 mg) and N-methylmorpholine (31 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 14 hours. The reaction mixture was poured into water (8 ml) and shaken. This was then centrifuged, and the supernatant was removed. After adding saturated sodium bicarbonate water (8 ml) to the residue and stirring, the mixture was centrifuged and the supernatant was removed. The procedure of centrifugation and removal of the supernatant was then carried out once with saturated sodium bicarbonate water (8 ml) and twice with water (8 ml). The residue was dried under reduced pressure. A portion thereof was purified by preparative high performance liquid chromatography using methanol/trifluoroacetic acid (100/0.1) and water/trifluoroacetic acid (100/0.1) as a mixed eluent, to obtain 3.4 mg of the title compound.

The mass spectrometry (MS) data for the obtained compound were as follows.

MS: m/z 1242.6 ($M^+$+23).

Example 46

Synthesis of tris[4-[N-[2-(1H-indol-3-yl)acetyl]-4-nitro-L-phenylalanyl]aminophenyl]methane Reaction was conducted in the same manner as Example 42, except that the tris[4-(4-nitro-L-phenylalanyl) aminophenyl]methane obtained in Reference Example 53 was used instead of tris[4-(L-tryptophyl)aminophenyl] methane, to obtain 1.9 mg of the title compound.

The mass spectrometry (MS) data for the obtained compound were as follows.

MS: m/z 1337.5 ($M^+$+1).

Example 47

Synthesis of tris[4-[N-[2-(2-methyl-1H-indol-3-yl) acetyl]-4-nitro-L-phenylalanyl]aminophenyl] methane Reaction was conducted in the same manner as Example 43, except that the tris[4-(4-nitro-L-phenylalanyl) aminophenyl]methane obtained in Reference Example 53 was used instead of tris[4-(L-tryptophyl)aminophenyl] methane, to obtain 1.8 mg of the title compound.

The mass spectrometry (MS) data for the obtained compound were as follows.

MS: m/z 1379.1 ($M^+$+1). MS: m/z.

Example 48

Synthesis of tris[4-[N-[2-(5-methoxy-2-methyl-1H-indol3-yl)acetyl]-4-nitro-L-phenylalanyl] aminophenyl]methane Reaction was conducted in the same manner as Example 44, except that the tris[4-(4-nitro-L-phenylalanyl) aminophenyl]methane obtained in Reference Example 53 was used instead of tris[4-(L-tryptophyl)aminophenyl] methane, to obtain 2.0 mg of the title compound.

The mass spectrometry (MS) data for the obtained compound were as follows.

MS: m/z 918.9, 1469.1 ($M^+$+1).

Example 49

Synthesis of tris[4-[4-nitro-N-[2-(thiophen-3-yl) acetyl]-L-phenylalanyl]aminophenyl]methane Reaction was conducted in the same manner as Example 45, except that the tris[4-(4-nitro-L-phenylalanyl) aminophenyl]methane obtained in Reference Example 53 was used instead of tris[4-(L-tryptophyl)aminophenyl] methane, to obtain 1.7 mg of the title compound.

The mass spectrometry (MS) data for the obtained compound were as follows.

MS: m/z 1238.5 ($M^+$+1).

Example 50

Synthesis of tris[4-[N-α-[2-(1H-indol-3-yl)acetyl]-L-asparaginyl]aminophenyl]methane Reaction was conducted in the same manner as Example 42, except that the tris[4-(L-asparaginyl)aminophenyl] methane obtained in Reference Example 54 was used instead of tris[4-(L-tryptophyl)aminophenyl]methane, to obtain 1.6 mg of the title compound.

The mass spectrometry (MS) data for the obtained compound were as follows.

MS: m/z 832.2, 1103.2 ($M^+$+1), 1125.6 ($M^+$+23).

Example 51

Synthesis of tris[4-[N-α-[2-(2-methyl-1H-indol-3-yl)acetyl]-L-asparaginyl]aminophenyl]methane Reaction was conducted in the same manner as Example 43, except that the tris[4-(L-asparaginyl)aminophenyl] methane obtained in Reference Example 54 was used instead of tris[4-(L-tryptophyl)aminophenyl]methane, to obtain 1.3 mg of the title compound.

The mass spectrometry (MS) data for the obtained compound were as follows.

MS: m/z 860.0, 1145.5 ($M^+$+1), 1167.6 ($M^+$+23).

Example 52

Synthesis of tris[4-[N-α-[2-(5-methoxy-2-methyl-1H-indol-3-yl)acetyl]-L-asparaginyl]aminophenyl] methane Reaction was conducted in the same manner as Example 44, except that the tris[4-(L-asparaginyl)aminophenyl] methane obtained in Reference Example 54 was used instead of tris[4-(L-tryptophyl)aminophenyl]methane, to obtain 1.4 mg of the title compound.

The mass spectrometry (MS) data for the obtained compound were as follows.

MS: m/z 920.2, 1235.3 ($M^+$+1), 1257.5 ($M^+$+23).

Example 53

Synthesis of tris[4-([-α-[2-(thiophen-3-yl)acetyl]-L-asparaginyl]aminophenyl]methane Reaction was conducted in the same manner as Example 45, except that the tris[4-(L-asparaginyl)aminophenyl] methane obtained in Reference Example 54 was used instead of tris[4-(L-tryptophyl)aminophenyl]methane, to obtain 1.0 mg of the title compound.

The mass spectrometry (MS) data for the obtained compound were as follows.

MS: m/z 766.1, 1004.0 ($M^+$+1), 1026.4 ($M^+$+23).

Example 54

Synthesis of tris[4-[N-[2-(1H-indol-3-yl)acetyl] glycyl]aminophenyl]methane

Reaction was conducted in the same manner as xample 42, except that the tris(4-glycylaminophenyl)methane obtained in Reference Example 55 was used instead of tris[4-(L-tryptophyl) aminophenyl]methane, to obtain 2.5 mg of the title compound.

The mass spectrometry (MS) data for the obtained compound were as follows.

MS: m/z 932.3 (M$^+$+1), 954.5 (M$^+$+23), 1885.5 (2M$^+$+23).

Example 55

Synthesis of tris[4-[N-[2-(2-methyl-1H-indol-3-yl)acetyl]glycyl]aminophenyl]methane Reaction was conducted in the same manner as Example 43, except that the tris(4-glycylaminophenyl)methane obtained in Reference Example 55 was used instead of tris[4-(L-tryptophyl) aminophenyl]methane, to obtain 2.3 mg of the title compound.

The mass spectrometry (MS) data for the obtained compound were as follows.

MS: m/z 974.3 (M$^+$+1), 996.5 (M$^+$+23), 1969.6 (2M$^+$+23).

Example 56

Synthesis of tris[4-[N-[2-(thiophen-3-yl)acetyl]glycyl]aminophenyl]methane

Reaction was conducted in the same manner as Example 44, except that the tris(4-glycylaminophenyl)methane obtained in Reference Example 55 was used instead of tris[4-(L-tryptophyl) aminophenyl]methane, to obtain 2.4 mg of the title compound.

The mass spectrometry (MS) data for the obtained compound were as follows.

MS: m/z 806.1, 1064.4 (M$^+$+8), 1086.6 (M$^+$+23).

Example 57

Synthesis of tris[4-[N-[2-(1H-indol-3-yl)acetyl]glycyl]aminophenyl]methane

Reaction was conducted in the same manner as Example 45, except that the tris(4-glycylaminophenyl)methane obtained in Reference Example 55 was used instead of tris[(4-(L-tryptophyl) aminophenyl]methane, to obtain 1.6 mg of the title compound.

The mass spectrometry (MS) data for the obtained compound were as follows.

MS: m/z 833.1 (M$^+$+1), 855.3 (M$^+$+23), 1688.0 (2M$^+$+23).

Example 58

Synthesis of tris[4-[N-[2-(1-H-indol-3-yl)acetyl]-β-methylsulfonylmethyl-L-alanyl]aminophenyl]methane Reaction was conducted in the same manner as Example 42, except that the tris[4(β-methylsulfonylmethyl-L-alanyl)aminophenyl]methane obtained in Reference Example 56 was used instead of tris[4-(L-tryptophyl)aminophenyl]methane, to obtain 3.0 mg of the title compound.

The mass spectrometry (MS) data for the obtained compound were as follows.

MS: m/z 1248.1 (M$^+$+1), 1272.5 (M$^+$+23).

Example 59

Synthesis of tris(4-[N-[2-[2-methyl-1H-indol-3-yl)acetyl]-β-methylsulfonylmethyl-L-alanyl]aminophenyl]methane Reaction was conducted in the same manner as Example 43, except that the tris[4-(β-methylsulfonylmethyl-L-alanyl) aminophenyl]methane obtained in Reference Example 56 was used instead of tris[4-(L-tryptophyl)aminophenyl]methane, to obtain 1.9 mg of the title compound.

The mass spectrometry (MS) data for the obtained compound were as follows.

MS: m/z 1314.6 (M$^+$+23).

Example 60

Synthesis of tris[4-[N-[2-(5-methoxy-2-methyl-1H-indol-3-yl)acetyl]-β-methylsulfonylmethyl-L-alanyl]aminophenyl]methane Reaction was conducted in the same manner as Example 44, except that the tris[4-(β-methylsulfonylmethyl-L-alanyl) aminophenyl]methane obtained in Reference Example 56 was used instead of tris[4-(L-tryptophyl)aminophenyl]methane, to obtain 2.8 mg of the title compound.

The mass spectrometry (MS) data for the obtained compound were as follows.

MS: m/z 1404.6 (M$^+$+23).

Example 61

Synthesis of tris[4-[β-methylsulfonylmethyl-N-[2(thiophen-3-yl)acetyl]-L-alanyl]aminophenyl]methane Reaction was conducted in the same manner as Example 45, except that the tris[4-(β-methylsulfonylmethyl-L-alanyl) aminophenyl]methane obtained in Reference Example 56 was used instead of tris[4-(L-tryptophyl)aminophenyl]methane, to obtain 2.1 mg of the title compound.

The mass spectrometry (MS) data for the obtained compound were as follows.

MS: m/z 1173.4 (M$^+$+23).

Example 62

Synthesis of tris[4-[N-α-[2-(1H-indol-3-yl)acetyl]-L-citrullyl]aminophenyl]methane Reaction was conducted in the same manner as Example 42, except that the tris[4-(L-citrullyl)aminophenyl]methane obtained in Reference Example 57 was used instead of tris[4-(L-tryptophyl)aminophenyl]methane, to obtain 2.7 mg of the title compound.

The mass spectromtry (MS) data for the obtained compound were as follows.

MS: m/z 918.3, 1232.5 (M$^+$+1), 1254.6 (M$^+$+23).

Example 63

Synthesis of tris[4-[N-α-[2-(2-methyl-1H-indol-3-yl)acetyl]-L-citrullyl]aminophenyl]methane Reaction was conducted in the same manner as Example 43, except that the tris[4-(L-citrullyl)aminophenyl]methane obtained of tris[4-(L-tryptophyl)aminophenyl]methane, to obtain 3.0 mg of the title compound.

The mass spectrometry (MS) data for the obtained compound were as follows.

MS: m/z 1274.5 (M$^+$+1), 1296.8 (M$^+$+23).

Example 64

Synthesis of tris[4-[N-α-[2-(5-methoxy-2-methyl-1H-indol-3-yl)acetyl]-L-citrullyl]aminophenyl]methane Reaction was conducted in the same manner as Example 44, except that the tris[4-(L-tryptophyl)aminophenyl]methane, to obtain 2.2 mg of the title compound.

Example 65

Synthesis of tris[4-[N-α-[2-(thiophen-3-yl)acetyl]-L-citrullyl]aminophenyl]methane Reaction was conducted in the same manner as Example 45, except that the tris[(4-(L-citrullyl)aminophenyl]methane obtained in Reference Example 57 was used instead of tris[4-(L-tryptophyl)aminophenyl]methane, to obtain 3.3 mg of the title compound.

The mass spectrometry (MS) data for the obtained compound were as follows.

MS: m/z 1133.4 ($M^++1$), 1155.5 ($M^++23$).

Example 66

Synthesis of tris[4-[N-[2-(1H-indol-3-yl)acetyl]-β-(pyridin-2-yl)-L-alanyl]aminophenyl]methane trifluoroacetate Reaction was conducted in the same manner as Example 42, except that the tris[4-[β5-(pyridin-2-yl)-L-alanyl-]aminophenyl]methane obtained in Reference Example 58 was used instead of tris[4-(L-tryptophyl)aminophenyl]methane, to obtain 2.2 mg of the title compound.

The mass spectrometry (MS) data for the obtained compound were as follows.

MS: m/z 1205.5 ($M^++1$), 1227.6 ($M^++23$).

Example 67

Synthesis of triss[4-[N-[2-(2-methyl-1H-indol-3-yl)acetyl]-β-(pyridin-2-yl)-L-alanyl]aminophenyl]methane trifluoroacetate Reaction was conducted in the same manner as Example 43, except that the tris[4-[β-(pyridin-2-yl)-L-alanyl]aminophenyl]methane obtained in Reference Example 58 was used instead of tris[4-(Ltryptophyl)aminophenyl]methane, to obtain 2.8 mg of the title compound.

The mass spectrometry (MS) data for the obtained compound were as follows.

MS: m/z 1247.5 ($M^++1$), 1269.8 ($M^++23$).

Example 68

Synthesis of tris[4-[N-[2-(5-methoxy-2-methyl-1H-indol-3-yl)acetyl]-β-(pyridin-2-yl)-L-alanyl]aminophenyl]methane trifluoroacetate Reaction was conducted in the same manner as Example 44, except that the tris[4-[β-(pyridin-2-yl)-L-alanyl]aminophenyl]methane obtained in Reference Example 58 was used instead of tris[4-(L-tryptophyl)aminophenyl]methane, to obtain 2.6 mg of the title compound.

The mass spectrometry (MS) data for the obtained compound were as follows.

MS: m/z 1337.5 ($M^++1$), 1359.7 ($M^++23$).

Example 69

Synthesis of tris[4-[β-(pyridin-2-yl)-N-[2-(thiophen-3-yl)acetyl]-L-alanyl]aminophenyl]methane trifluoroacetate Reaction was conducted in the same manner as Example 45, except that the tris[4-[β-(pyridin-2-yl)-L-alanyl] aminophenyl]methane obtained in Reference Example 58 was used instead of tris[4-(L-tryptophyl)aminophenyl] methane, to obtain 2.4 mg of the title compound.

The mass spectrometry (MS) data for the obtained compound were as follows.

MS: m/z 1106.3 ($M^++1$), 1128.5 ($M^++23$).

Example 70

Synthesis of tris[4-[O-benzyl-N-[2-(1H-indol-3-yl)acetyl]-L-seryl]aminophenyl]methane Reaction was conducted in the same manner as Example 42, except that the tris[4-(O-benzyl-L-seryl)aminophenyl] methane obtained in Reference Example 59 was used instead of tris[4-(L-tryptophyl)aminophenyl]methane, to obtain 1.3 mg of the title compound.

The mass spectrometry (MS) data for the obtained compound were as follows.

MS: m/z 1314.7 ($M^++23$).

Example 71

Synthesis of tris[4-[O-benzyl-N-[2-(5-methoxy-2-methyl-1H-indol-3-yl)acetyl]-L-seryl]aminophenyl] methane Reaction was conducted in the same manner as Example 44, except that the tris[4-(O-benzyl-L-seryl)aminophenyl] methane obtained in Reference Example 59 was used instead of tris[4-(L-tryptophyl)aminophenyl]methane, to obtain 1.6 mg of the title compound.

The mass spectrometry (MS) data for the obtained compound were as follows.

MS: m/z 1424.4 ($M^++1$), 1447.7 ($M^++23$).

Example 72

Synthesis of tris[4-[N-ε-acetyl-N-α-[2-(1H-indol-3-yl)acetyl]-L-lysyl]aminophenyl]methane Reaction was conducted in the same manner as Example 42, except that the tris[4-(N-ε-acetyl-L-lysyl)aminophenyl] methane obtained in Reference Example 60 was used instead of tris[4-(L-tryptophyl)aminophenyl]methane, to obtain 2.3 mg of the title compound.

The mass spectrometry (MS) data for the obtained compound were as follows.

MS: m/z 1271.6 ($M^++1$), 1293.8 ($M^++23$).

Example 73

Synthesis of tris[4-[N-ε-acetyl-N-α-[2-(2-methyl-1-H-indol-3-yl)acetyl]-L-lysyl]aminophenyl]methane Reaction was conducted in the same manner as Example 43, except that the tris[4-[(N-α-acetyl)-L-lysyl] aminophenyl]methane obtained in Reference Example 60 was used instead of tris[4-(L-tryptophyl)aminophenyl] methane, to obtain 3.3 mg of the title compound.

The mass spectrometry (MS) data for the obtained compound were as follows.

MS: m/z 1335.8 ($M^++23$).

Example 74

Synthesis of tris[4-[N-ε-acetyl-N-α-[2-(5-methoxy-2-methyl-1H-indol-3-yl)acetyl]-L-lysyl] aminophenyl]methane Reaction was conducted in the same manner as Example 44, except that the tris[4-(N-ε-acetyl-L-lysyl)aminophenyl]

methane obtained in Reference Example 60 was used instead of tris[4-(L-tryptophyl)aminophenyl]methane, to obtain 3.3 mg of the title compound.

The mass spectrometry (MS) data for the obtained compound were as follows.

MS: m/z 1425.9 ($M^+$+23).

Example 75

Synthesis of tris[4-[N-ε-acetyl-N-α-[2-(thiophen-3-yl)acetyl]-L-lysyl]aminophenyl]methane Reaction was conducted in the same manner as Example 45, except that the tris[4-(N-ε-acetyl-L-lysyl)aminophenyl]methane obtained in Reference Example 60 was used instead of tris[4-(L-tryptophyl)aminophenyl]methane, to obtain 2.3 mg of the title compound.

The mass spectrometry (MS) data for the obtained compound were as follows.

MS: m/z 1172.4 ($M^+$+1), 1195.7 ($M^+$+23).

Example 76

Synthesis of tris[4-[N-[2-(1H-indol-3-yl)acetyl]-β-alanyl]aminophenyl]methane

Reaction was conducted in the same manner as Example 42, except that the tris[4-(β-alanyl)aminophenyl]methane obtained in Reference Example 61 was used instead of tris[4-(L-tryptophyl) aminophenyl]methane, to obtain 2.7 mg of the title compound.

The mass spectrometry (MS) data for the obtained compound were as follows.

MS: m/z 746.3, 974.3 ($M^+$+1), 996.6 ($M^+$+23).

Example 77

Synthesis of tris[4-[N-[2-(2-methyl-1H-indol-3-yl)acetyl]-β-alanyl]aminophenyl]methane Reaction was conducted in the same manner as Example 43, except that the tris[4-(β-alanyl)aminophenyl]methane obtained in Reference Example 61 was used instead of tris[4-(L-tryptophyl) aminophenyl]methane, to obtain 6.7 mg of the title compound.

The mass spectrometry (MS) data for the obtained compound were as follows.

MS: m/z 1016.6 ($M^+$+1), 1038.7 ($M^+$+23).

Example 78

Synthesis of tris[4-[N-[2-(5-methoxy-2-methyl-1H-indol-3-yl)acetyl]-β-alanyl]aminophenyl]methane Reaction was conducted in the same manner as Example 44, except that the tris[4-(β-alanyl)aminophenyl]methane obtained in Reference Example 61 was used instead of tris[4-(L-tryptophyl) aminophenyl]methane, to obtain 3.8 mg of the title compound.

The mass spectrometry (MS) data for the obtained compound were as follows.

MS: m/z 1106.5 ($M^+$+1), 1028.7 ($M^+$+23).

Example 79

Synthesis of tris[4-[N-[2-(thiophen-3-yl)acetyl]-β-alanyl]aminophenyl]methane

Reaction was conducted in the same manner as Example 45, except that the tris[4-β-alanyl)aminophenyl]methane obtained in Reference Example 61 was used instead of tris[4-(L-tryptophyl) aminophenyl]methane, to obtain 2.6 mg of the title compound.

The mass spectrometry (MS) data for the obtained compound were as follows.

MS: m/z 875.4 ($M^+$+1), 897.5 ($M^+$+23), 1771.1 (2$M^+$+23).

Example 80

Synthesis of tris[4-[N-[2-(1H-indol-3-yl)acetyl]-L-methionyl]aminophenyl]methane Reaction was conducted in the same manner as Example 42, except that the tris[4-(L-methionyl)aminophenyl]methane obtained in Reference Example 62 was used instead of tris[4-(L-tryptophyl)aminophenyl]methane, to obtain 2.3 mg of the title compound.

The mass spectrometry (MS) data for the obtained compound were as follows.

MS: m/z 1155.4 ($M^+$+1), 1176.6 ($M^+$+23).

Example 81

Synthesis of tris[4-[N-[2-(2-methyl-1H-indol-3-yl)acetyl]-L-methionyl]aminophenyl]methane Reaction was conducted in the same manner as Example 43, except that the tris[4-(L-methionyl)aminophenyl]methane obtained in Reference Example 62 was used instead of tris[4-(L-tryptophyl)aminophenyl]methane, to obtain 2.8 mg of the title compound.

The mass spectrometry (MS) data for the obtained compound were as follows.

MS: m/z 1218.6 ($M^+$+23).

Example 82

Synthesis of tris[4-[N-[2-(5-methoxy-2-methyl-1H-indol-3-yl)acetyl]-L-methionyl]aminophenyl]methane Reaction was conducted in the same manner as Example 44, except that the tris[4-(L-methionyl)aminophenyl]methane obtained in Reference Example 62 was used instead of tris[4-(L-tryptophyl)aminophenyl]methane, to obtain 4.5 mg of the title compound.

The mass spectrometry (MS) data for the obtained compound were as follows.

MS: m/z 1287.4 ($M^+$+1), 1309.7 ($M^+$+23).

Example 83

Synthesis of tris[4-[N-[2-(thiophen-3-yl)acetyl]-L-methionyl]aminophenyl]methane Reaction was conducted in the same manner as Example 45, except that the tris[4-(L-methionyl)aminophenyl]methane obtained in Reference Example 62 was used instead of tris[4-(L-tryptophyl)aminophenyl]methane, to obtain 4.0 mg of the title compound.

The mass spectrometry (MS) data for the obtained compound were as follows.

MS: m/z 1055.0 ($M^+$+1), 1077.5 ($M^+$+23).

Example 84

Synthesis of tris[4-[N-[2-(1H-indol-3-yl)acetyl]-L-phenylalanyl]aminophenyl]methane Reaction was conducted in the same manner as Example 42, except that the tris[4-(L-phenylalanyl)aminophenyl]

methane obtained in Reference Example 63 was used instead of tris[4-(L-tryptophyl)aminophenyl]methane, to obtain 2.6 mg of the title compound.

The mass spectrometry (MS) data for the obtained compound were as follows.

MS: m/z 1224.7 (M$^+$+23).

Example 85

Synthesis of tris[4-[N-[2-(2-methyl-1H-indol-3-yl)acetyl]-L-phenylalanyl]aminophenyl]methane Reaction was conducted in the same manner as Example 43, except that the tris[4-(L-phenylalanyl)aminophenyl]methane obtained in Reference Example 63 was used instead of tris[4-(L-tryptophyl)aminophenyl]methane, to obtain 2.9 mg of the title compound.

The mass spectrometry (MS) data for the obtained compound were as follows.

MS: m/z 1266.6 (M$^+$+23).

Example 86

Synthesis of tris[4-[N-[2-(5-methoxy-2-methyl-1H-indol-3-yl)acetyl]-L-phenylalanyl]aminophenyl]methane Reaction was conducted in the same manner as Example 44, except that the tris[4-(L-phenylalanyl)aminophenyl]methane obtained in Reference Example 63 was used instead of tris[4-(L-tryptophyl)aminophenyl]methane, to obtain 3.6 mg of the title compound.

The mass spectrometry (MS) data for the obtained compound were as follows.

MS: m/z 1334.4 (M$^+$+1), 1356.7 (M$^+$+23).

Example 87

Synthesis of tris[4-[N-[2-(thiophen-3-yl)acetyl]-L-phenylalanyl]aminophenyl]methane Reaction was conducted in the same manner as Example 0.45, except that the tris[4-(L-phenylalanyl)aminophenyl]methane obtained in Reference Example 63 was used instead of tris[4-(L-tryptophyl)aminophenyl]methane, to obtain 2.4 mg of the title compound.

The mass spectrometry (MS) data for the obtained compound were as follows.

MS: m/z 1125.6 (M$^+$23).

Example 88

Synthesis of tris[4-[N-τ-benzyloxmethyl-N-α-[2-(1H-indol-3-yl)acetyl]-L-histidyl]aminophenyl]methane Reaction was conducted in the same manner as Example 42, except that the tris[4-(N-τ-benzyloxymethyl-L-histidyl)aminophenyl]methane obtained in Reference Example 64 was used instead of tris[4-(L-tryptophyl)aminophenyl]methane, to obtain 1.7 mg of the title compound.

The mass spectrometry (MS) data for the obtained compound were as follows.

MS: m/z 1532.6 (M$^+$+1), 1554.7 (M$^+$+23).

Example 89

Synthesis of tris[4-[N-τ-benzyloxymethyl-N-α-[2-(2-methyl-1H-indol-3-yl)acetyl]-L-histidyl]aminophenyl]methane Reaction was conducted in the same manner as Example 43, except that the tris[4-(N-τ-benzyloxymethyl-L-histidyl)aminophenyl]methane obtained in Reference Example 64 was used instead of tris[4-(L-7-tryptophyl)aminophenyl]methane, to obtain 2.0 mg of the title compound.

The mass spectrometry (MS) data for the obtained compound were as follows.

MS: m/z 1574.6 (M$^+$+1), 1597.7 (M$^+$+23).

Example 90

Synthesis of tris[4-[N-τ-benzyloxymethyl-N-α-[2-(5-methoxy-2-methyl-1H-indol-3-yl)acetyl]-L-histidyl]aminophenyl]methane Reaction was conducted in the same manner as Example 44, except that the tris[4-(N-τ-benzyloxymethyl-L-histidyl)aminophenyl]methane obtained in Reference Example 64 was used instead of tris[4-(L-tryptophyl)aminophenyl]methane, to obtain 3.8 mg of the title compound.

The mass spectrometry (MS) data for the obtained compound were as follows.

MS: m/z 1164.6 (M$^+$+1), 1686.7 (M$^+$+23).

Example 91

Synthesis of tris[4-[N-τ-benzyloxymethyl-N-α-[2-(thiophen-3-yl)acetyl]-L-histidyl]aminophenyl]methane Reaction was conducted in the same manner as Example 45, except that the tris[4-(N-τ-benzyloxymethyl-L-histidyl)aminophenyl]methane obtained in Reference Example 64 was used instead of tris[4-(L-tryptophyl)aminophenyl]methane, to obtain 2.3 mg of the title compound.

The mass spectrometry (MS) data for the obtained compound were as follows.

MS: m/z 1433.6 (M$^+$+1).

Example 92

Synthesis of tris[4-[O-benzyl-N-[2-(1H-indol-3-yl)acetyl]-L-tyrosyl]aminophenyl]methane Reaction was conducted in the same manner as Example 42, except that the tris[4-(O-benzyl-L-tyrosyl)aminophenyl]methane obtained in Reference Example 65 was used instead of tris[4-(L-tryptophyl)aminophenyl]methane, to obtain 2.0 mg of the title compound.

The mass spectrometry (MS) data for the obtained compound were as follows.

MS: m/z 1520.4 (M$^+$+1), 1542.7 (M$^+$+23).

Example 93

Synthesis of tris[4-[O-benzyl-N-[2-(2-methyl-1H-indol-3-yl)acetyl]-L-tyrosyl]aminophenyl]methane Reaction was conducted in the same manner as Example 43, except that the tris[4-(O-benzyl-L-tyrosyl)aminophenyl]methane obtained in Reference Example 65 was used instead of tris[4-(L-tryptophyl)aminophenyl]methane, to obtain 3.3 mg of the title compound.

The mass spectrometry (MS) data for the obtained compound were as follows.

MS: m/z 1562.4 (M$^+$+1), 1584.7 (M$^+$+23).

Example 94

Synthesis of tris[4-[O-benzyl-N-[2-(5-methoxy-2-methyl-1H-indol-3-yl)acetyl]-L-tyrosyl]aminophenyl]methane Reaction was conducted in the same manner as Example 44, except that the tris[4-(O-benzyl-L-tyrosyl)aminophenyl]

methane obtained in Reference Example 65 was used instead of tris[4-(L-tryptophyl)aminophenyl]methane, to obtain 2.4 mg of the title compound.

The mass spectrometry (MS) data for the obtained compound were as follows.

MS: m/z 1652.6 ($M^+$+1), 1674.7 ($M^+$+23).

Example 95

Synthesis of tris[4-[N-[2-(1H-indol-3-yl)acetyl]-L-norleucyl]aminophenyl]methane Reaction was conducted in the same manner as Example 42, except that the tris[4-(L-norleucyl)aminophenyl]methane obtained in Reference Example 66 was used instead of tris[4-(L-tryptophyl)aminophenyl]methane, to obtain 2.7 mg of the title compound.

The mass spectrometry (MS) data for the obtained compound were as follows.

MS: m/z 1100.4 ($M^+$+1), 1122.7 ($M^+$+23).

Example 96

Synthesis of tris[4-[N-[2-(2-methyl-1H-indol-3-yl)acetyl]-L-norleucyl]aminophenyl]methane Reaction was conducted in the same manner as Example 43, except that the tris[4-(L-norleucyl)aminophenyl]methane obtained in Reference Example 66 was used instead of tris[4-(L-tryptophyl)aminophenyl]methane, to obtain 2.7 mg of the title compound.

The mass spectrometry (MS) data for the obtained compound were as follows.

MS: m/z 1100.4 ($M^+$+1), 1122.7 ($M^+$+23).

Example 97

Synthesis of tris[4-[N-[2-(5-methoxy-2-methyl-1H-indol-3-yl)acetyl]-L-norleucyl]aminophenyl]methane Reaction was conducted in the same manner as Example 44, except that the tris[4-(L-norleucyl)aminophenyl]methane obtained in Reference Example 66 was used instead of tris[4-(L-tryptophyl)aminophenyl]methane, to obtain 3.2 mg of the title compound.

The mass spectrometry (MS) data for the obtained compound were as follows.

MS: m/z 1232.5 ($M^+$+1), 1254.8 ($M^+$+23).

Example 98

Synthesis of tris[4-[(N-[2-(thiophen-3-yl)acetyl]-L-norleucyl]aminophenyl]methane Reaction was conducted in the same manner as Example 45, except that the tris[4-(L-norleucyl)aminophenyl]methane obtained in Reference Example 66 was used instead of tris[4-(L-tryptophyl)aminophenyl]methane, to obtain the title compound.

The mass spectrometry (MS) data for the obtained compound were as follows.

MS: m/z 1001.3 ($M^+$+1), 1023.7 ($M^+$+23).

Example 99

Synthesis of tris[4-[N-α-[2-(1H-indol-3-yl)acetyl]-N-δ-(pyrazin-2-yl)carbonyl-L-ornithyl]aminophenyl]methane trifluoroacetate Reaction was conducted in the same manner as Example 42, except that the tris[4-[N-δ-(pyrazin-2-yl)carbonyl-L-ornithyl]aminophenyl]methane obtained in Reference Example 67 was used instead of tris[4-(L-tryptophyl)aminophenyl]methane, to obtain 3.7 mg of the title compound.

The mass spectrometry (MS) data for the obtained compound were as follows.

MS: m/z 1443.8 ($M^+$+23).

Example 100

Synthesis of tris[4-[N-α-[2-(2-methyl-1H-indol-3-yl)acetyl]-N-δ-(pyrazin-2-yl)carbonyl-L-ornithyl]aminophenyl]methane trifluoroacetate Reaction was conducted in the same manner as Example 43, except that the tris[4-[N-δ-(pyrazin-2-yl)carbonyl-L-ornithyl]aminophenyl]methane obtained in Reference Example 67 was used instead of tris[4-(L-tryptophyl)aminophenyl]methane, to obtain 2.0 mg of the title compound.

The mass spectrometry (MS) data for the obtained compound were as follows.

MS: m/z 1485.9 ($M^+$+23).

Example 101

Synthesis of tris[4-[N-α-[2-(5-methoxy-2-methyl-1-H-indol-3-yl)acetyl]-N-6-(pyrazin-2-yl)carbonyl-L-ornithyl]aminophenyl]methane trifluoroacetate Reaction was conducted in the same manner as Example 44, except that the tris[4-[N-δ-(pyrazin-2-yl)carbonyl-L-ornithyl]aminophenyl]methane obtained in Reference Example 67 was used instead of tris[4-(L-tryptophyl)aminophenyl]methane, to obtain 4.8 mg of the title compound.

The mass spectrometry (MS) data for the obtained compound were as follows.

MS: m/z 1575.9 ($M^+$+23).

Example 102

Synthesis of tris[4-[N-δ-(pyrazin-2-yl)carbonyl-N-α-[2(thiophen-3-yl)acetyl]-L-ornithyl]aminophenyl]methane trifluoroacetate Reaction was conducted in the same manner as Example 45, except that the tris[4-[N-δ-(pyrazin-2-yl)carbonyl-L-ornithyl]aminophenyl]methane obtained in Reference Example 67 was used instead of tris[4-(L-tryptophyl)aminophenyl]methane, to obtain 2.5 mg of the title compound.

The mass spectrometry (MS) data for the obtained compound were as follows.

MS: m/z 1344.8 ($M^+$+23).

Example 103

Synthesis of tris[4-[N-[2-(1H-indol-3-yl)acetyl]-β-(pyridin-4-yl)-D-alanyl]aminophenyl]methane trifluoroacetate Reaction was conducted in the same manner as Example 42, except that the tris[4-[β-(pyridin-4-yl)-D-alanyl]aminophenyl]methane obtained in Reference Example 68 was used instead of tris[4-(L-tryptophyl)aminophenyl]methane, to obtain 3.6 mg of the title compound.

Example 104

Synthesis of tris[4-[N-[2-(2-methyl-1H-indol-3-yl)acetyl]-β-(pyridin-4-yl)-D-alanyl]aminophenyl]methane trifluoroacetate Reaction was conducted in the same manner as Example 43, except that the tris[4-[β-(pyridin-4-yl)-D-alanyl]aminophenyl]methane obtained in Reference Example 68 was used instead of tris[4-(L-tryptophyl)aminophenyl]methane, to obtain 4.4 mg of the title compound.

The mass spectrometry (MS) data for the obtained compound were as follows.

MS: m/z 1247.6 ($M^+$+1).

Example 105

Synthesis of tris[4-[N-[2-(5-methoxy-2-methyl-1H-indol-3-yl)acetyl]-β-(pyridin-4-yl)-D-alanyl]aminophenyl]methane trifluoroacetate Reaction was conducted in the same manner as Example 44, except that the tris[4-[β-(pyridin-4-yl)-D-alanyl]aminophenyl]methane obtained in Reference Example 68 was used instead of tris[4-(L-tryptophyl)aminophenyl]methane, to obtain 3.9 mg of the title compound.

The mass spectrometry (MS) data for the obtained compound were as follows.

MS: m/z 1337.6 ($M^+$+1).

Example 106

Synthesis of tris[4-[β-(pyridin-4-yl)-N-[2-(thiophen-3-yl)acetyl]-D-alanyl]aminophenyl]methane trifluoroacetate Reaction was conducted in the same manner as Example 45, except that the tris[4-[β-(pyridin-4-yl)-D-alanyl]aminophenyl]methane obtained in Reference Example 68 was used instead of tris[4-(L-tryptophyl)aminophenyl]methane, to obtain 3.5 mg of the title compound.

The mass spectrometry (MS) data for the obtained compound were as follows.

MS: m/z 1106.4 ($M^+$+1).

Example 107

Synthesis of tris[4-[N-α-[2-(1H-indol-3-yl)acetyl]-L-glutaminyl]aminophenyl]methane Reaction was conducted in the same manner as Example 42, except that the tris[4-(L-glutaminyl) aminophenyl]methane obtained in Reference Example 69 was used instead of tris[4-(L-tryptophyl)aminophenyl]methane, to obtain 4.0 mg of the title compound.

The mass spectrometry (MS) data for the obtained compound were as follows.

MS: m/z 1145.4 ($M^+$+1), 1167.7 ($M^+$+23).

Example 108

Synthesis of tris[4-[N-α-[2-(2-methyl-1H-indol-3-yl)acetyl]-L-glutaminyl]aminophenyl]methane Reaction was conducted in the same manner as Example 43, except that the tris[4-(L-glutaminyl)aminophenyl]methane obtained in Reference Example 69 was used instead of tris[4-(L-tryptophyl)aminophenyl]methane, to obtain 2.0 mg of the title compound.

The mass spectrometry (MS) data for the obtained compound were as follows.

MS: m/z 1209.8 ($M^+$+23).

Example 109

Synthesis of tris[4-[N-α-[2-(5-methoxy-2-methyl-1H-indol-3-yl)acetyl]-L-glutaminyl]aminophenyl]methane Reaction was conducted in the same manner as Example 44, except that the tris[4-(L-glutaminyl)aminophenyl]methane obtained in Reference Example 69 was used instead of tris[4-(L-tryptophyl)aminophenyl]methane, to obtain 4.1 mg of the title compound.

The mass spectrometry (MS) data for the obtained compound were as follows.

MS: m/z 1299.8 ($M^+$+23).

Example 110

Synthesis of tris[4-[N-α-[2-(thiophen-3-yl)acetyl]-L-glutaminyl]aminophenyl]methane Reaction was conducted in the same manner as Example 45, except that the tris[4-(L-glutaminyl)aminophenyl]methane obtained in Reference Example 69 was used instead of tris[4-(L-tryptophyl)aminophenyl]methane, to obtain 2.6 mg of the title compound.

The mass spectrometry (MS) data for the obtained compound were as follows.

MS: m/z 1068.6 ($M^+$+23).

Example 111

Synthesis of tris[4-[N-α-[2-(1H-indol-3-yl)acetyl]-L-seryl]aminophenyl]methane

Reaction was conducted in the same manner as Example 42, except that the tris[4-(L-seryl)aminophenyl]methane obtained in Reference Example 70 was used instead of tris[4-(L-tryptophyl) aminophenyl]methane, to obtain 2.5 mg of the title compound.

The mass spectrometry (MS) data for the obtained compound were as follows.

MS: m/z 1044.6 ($M^+$+23).

Example 112

Synthesis of tris[4-[N-[2-(2-methyl-1H-indol-3-yl)acetyl]-L-seryl]aminophenyl]methane Reaction was conducted in the same manner as Example 43, except that the tris[4-(L-seryl)aminophenyl]methane obtained in Reference Example 70 was used instead of tris[4-(L-tryptophyl) aminophenyl]methane, to obtain 2.8 mg of the title compound.

The mass spectrometry (MS) data for the obtained compound were as follows.

MS: m/z 1086.7 ($M^+$+23).

Example 113

Synthesis of tris[4-[N-α-[2-(5-methoxy-2-methyl-1-H-indol-3-yl)acetyl]-L-seryl]aminophenyl]methane Reaction was conducted in the same manner as Example 44, except that the tris[4-(L-seryl)aminophenyl]methane obtained in Reference Example 70 was used instead of tris[4-(L-tryptophyl)aminophenyl]methane, to obtain 2.7 mg of the title compound.

The mass spectrometry (MS) data for the obtained compound were as follows.

MS: m/z 1154.4 (M$^+$+1), 1176.7 (M$^+$+23).

Example 114

Synthesis of tris[4-[N-α-[2-(thiophen-3-yl)acetyl]-L-seryl]aminophenyl]methane

Reaction was conducted in the same manner as Example 45, except that the tris[4-(L-seryl)aminophenyl]methane obtained in Reference Example 70 was used instead of tris[4-(L-tryptophyl)aminophenyl]methane, to obtain 2.7 mg of the title compound.

The mass spectrometry (MS) data for the obtained compound were as follows.

MS: m/z 945.4 (M$^+$+23).

Example 115

Synthesis of tris[4-[N-α-[2-(2-methyl-1H-indol-3-yl)acetyl]-N-δ-triphenylmethyl-L-glutaminyl]aminophenyl]methane Reaction was conducted in the same manner as Example 43, except that the tris[(4-(N-δ-triphenylmethyl-L-glutaminyl) aminophenyl]methane obtained in Reference Example 71 was used instead of tris[(4-(L-tryptophyl) aminophenyl]methane, to obtain 2.4 mg of the title compound.

The mass spectrometry (MS) data for the obtained compound were as follows.

MS: m/z 1936.0 (M$^+$+23).

Example 116

Synthesis of tris[4-[N-α-[2-(5-methoxy-2-methyl-1H-indol-3-yl)acetyl]-N-5-triphenylmethyl-L-glutaminyl]aminophenyl]methane Reaction was conducted in the same manner as Example 44, except that the tris[4-(N-δ-triphenylmethyl-L-glutaminyl) aminophenyl]methane obtained in Reference Example 71 was used instead of tris[4-(L-tryptophyl) aminophenyl]methane, to obtain 2.6 mg of the title compound.

The mass spectrometry (MS) data for the obtained compound were as follows.

MS: m/z 1024.7 (M$^+$/2+23).

Example 117

Synthesis of tris[4-[N-α-[2-(thiophen-3-yl)acetyl]-N-δ-triphenylmethyl-L-glutaminyl]aminophenyl]methane Reaction was conducted in the same manner as Example 45, except that the tris[4-(N-δ-triphenylmethyl-L-glutaminyl) aminophenyl]methane obtained in Reference Example 71 was used instead of tris[4-(L-tryptophyl) aminophenyl]methane, to obtain 2.3 mg of the title compound.

The mass spectrometry (MS) data for the obtained compound were as follows.

MS: m/z 1794.8 (M$^+$+23).

Example 118

Synthesis of tris[4-[N-[2-(1H-indol-3-yl)acetyl]-L-tyrosyl]aminophenyl]methane

The tris[4-[O-benzyl-N-[2-(1H-indol-3-yl)acetyl]-L-tyrosyl]aminophenyl]methane (70 mg) obtained in Example 92 was dissolved in a mixed solvent of methanol (4 ml) and N,N-dimethylformamide (4 ml), 10% palladium carbon (25 mg) was added, and then the mixture was stirred for 3 days at room temperature under a hydrogen atmosphere. The reaction mixture was filtered, and the filtrate was concentrated under reduced pressure. A portion of the residue was purified by preparative high performance liquid chromatography using methanol/trifluoroacetic acid (100/0.1) and water/trifluoroacetic acid (100/0.1) as a mixed eluent, to obtain 2.4 mg of the title compound.

The mass spectrometry (MS) data for the obtained compound were as follows.

MS: m/z 930.0, 1250.3 (M$^+$+1), 1272.6 (M$^+$+23).

Example 119

Synthesis of tris[4-[N-[2-(2-methyl-1H-indol-3-yl)acetyl]-L-tyrosyl]aminophenyl]methane Reaction was conducted in the same manner as Example 118, except that the tris[4-[O-benzyl-N-[2-(2-methyl-1H-indol-3-yl)acetyl]-L-tyrosyl]aminophenyl]methane obtained in Example 93 was used instead of tris[4-[O-benzyl-N-[2-(1H-indol-3-yl)acetyl]-L-tyrosyl]aminophenyl]methane, to obtain 1.7 mg of the title compound.

The mass spectrometry (MS) data for the obtained compound were as follows.

MS: m/z 1314.6 (M$^+$+23).

Example 120

Synthesis of tris[4-[4-amino-N-[2-(2-methyl-1H-indol-3-yl)acetyl]-L-phenylalanyl]aminophenyl] methane trifluoroacetate Reaction was conducted in the same manner as Example 118, except that the tris[4-[N-[2-(2-methyl-1-H-indol-3-yl)acetyl]-4-nitro-L-phenylalanyl]aminophenyl]methane obtained in Example 47 was used instead of tris[(4-[O-benzyl-N-[2-(1H-indol-3-yl)acetyl]-L-tyrosyl]aminophenyl]methane, to obtain 2.7 mg of the title compound.

The mass spectrometry (MS) data for the obtained compound were as follows.

MS: m/z 956.3, 1289.6 (M$^+$+1), 1311.8 (M$^+$+23).

Example 121

Synthesis of tris[4-[N-[2-(1H-indol-3-yl)acetyl]-α-L-aspartyl]aminophenyl]methane The tris[4-[β-t-butoxycarbonyl-L-alanyl]aminophenyl] methane obtained in Reference Example 72 (⅕ of the total amount obtained in Reference Example 72), 2-(1H-indol-3-yl)acetic acid (53 mg) and N-methylmorpholine (31 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 18 hours. The reaction mixture was poured into water (8 ml) and shaken. This was then centrifuged, and the supernatant was removed. After adding saturated sodium bicarbonate water (8 ml) to the residue and stirring, the mixture was centrifuged and the supernatant was removed. The procedure of centrifugation and removal of the supernatant was then carried out once with saturated sodium bicarbonate water (8 ml) and twice with water (8 ml). The residue was dried under reduced pressure, to obtain tris[4-[β-t-butoxycarbonyl-N-[2-(1H-indol-3-yl)acetyl]-L-alanyl]aminophenyl]methane.

A methanol solution containing trifluoroacetic acid (40%, 6 ml) was added to the tris[4-[β-t-butoxycarbonyl-N-[2-(1H-indol-3-yl)acetyl]-L-alanyl]aminophenyl]methane (50 mg) at room temperature, and the mixture was stirred at room temperature for 2 hours. The reaction solution was concentrated under reduced pressure, and a portion of the residue was purified by preparative high performance liquid chromatography using methanol/trifluoroacetic acid (100/0.1) and water/trifluoroacetic acid (100/0.1) as a mixed eluent, to obtain 1.3 mg of the title compound.

The mass spectrometry (MS) data for the obtained compound were as follows.

MS: m/z 1128.5 ($M^+$+23).

Example 122

Synthesis of tris[4-[N-[2-(2-methyl-1H-indol-3-yl)acetyl]-α-L-aspartyl]aminophenyl]methane Reaction was conducted in the same manner as Example 121, except that 2-(2-methyl-1H-indol-3-yl)acetic acid was used instead of 2-(1H-indol-3-yl)acetic acid, to obtain 2.5 mg of the title compound.

The mass spectrometry (MS) data for the obtained compound were as follows.

MS: m/z 1149.0 ($M^+$+1).

Example 123

Synthesis of tris[4-[N-[2-(5-methoxy-2-methyl-1H-indol-3-yl)acetyl]-α-L-aspartyl]aminophenyl]methane Reaction was conducted in the same manner as Example 121, except that 2-(5-methoxy-2-methyl-1-H-indol-3-yl)acetic acid was used instead of 2-(1H-indol-3-yl)acetic acid, to obtain 1.6 mg of the title compound.

The mass spectrometry (MS) data for the obtained compound were as follows.

MS: m/z 1238.4 ($M^+$+1), 1260.5 ($M^+$+23).

Example 124

Synthesis of tris[4-[N-[2-(thiophen-3-yl)acetyl]-α-L-aspartyl]aminophenyl]methane Reaction was conducted in the same manner as Example 121, except that 2-(thiophen-3-yl)acetic acid was used instead of 2-(1H-indol-3-yl)acetic acid, to obtain 1.4 mg of the title compound.

The mass spectrometry (MS) data for the obtained compound were as follows.

MS: m/z 1029.3 ($M^+$+23).

Example 125

Synthesis of tris[4-[N-[2-(2-methyl-1H-indol-3-yl)acetyl]-α-L-glutamyl]aminophenyl]methane The tris[4-[β-t-butoxycarbonylmethyl-L-alanyl]aminophenyl]methane obtained in Reference Example 73 (1/5 of the total amount obtained in Reference Example 73), 2-(2-methyl-1H-indol-3-yl)acetic acid (57 mg) and N-methylmorpholine (31 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 18 hours. The reaction mixture was poured into water (8 ml) and shaken. This was then centrifuged, and the supernatant was removed. After adding saturated sodium bicarbonate water (8 ml) to the residue and stirring, the mixture was centrifuged and the supernatant was removed. The procedure of centrifugation and removal of the supernatant was then carried out once with saturated sodium bicarbonate water (8 ml) and twice with water (8 ml). The residue was dried under reduced pressure to obtain tris[4-[β-t-butoxycarbonylmethyl-N-[2-(2-methyl-1H-indol-3-yl)acetyl]-L-alanyl]aminophenyl]methane.

A methanol solution containing trifluoroacetic acid (40%, 6 ml) was added to the tris[4-[β-t-butoxycarbonylmethyl-N-[2-(2-methyl-1H-indol-3-yl)acetyl]-L-alanyl]aminophenyl]methane (50 mg) at room temperature, and the mixture was stirred at room temperature for 2 hours. The reaction solution was concentrated under reduced pressure, a portion of the residue was purified by preparative high performance liquid chromatography using methanol/trifluoroacetic acid (100/0.1) and water/trifluoroacetic acid (100/0.1) as a mixed eluent, to obtain 2.0 mg of the title compound.

The mass spectrometry (MS) data for the obtained compound were as follows.

MS: m/z 1190.1 ($M^+$+1).

Example 126

Synthesis of tris[4-[N-[2-(5-methoxy-2-methyl-1H-indol-3-yl)acetyl]-α-L-glutamyl]aminophenyl]methane Reaction was conducted in the same manner as Example 125, except that 2-(5-methoxy-2-methyl-1H-indol-3-yl)acetic acid was used instead of 2-(2-methyl-1H-indol-3-yl)acetic acid, to obtain 1.6 mg of the title compound.

The mass spectrometry (MS) data for the Obtained compound were as follows.

MS: m/z 1280.4 ($M^+$+1), 1302.6 ($M^+$+23).

Example 127

Synthesis of tris[4-[N-[2-(thiophen-3-yl)acetyl]-α-L-glutamyl]aminophenyl]methane Reaction was conducted in the same manner as Example 125, except that 2-(thiophen-3-yl)acetic acid was used instead of 2-(2-methyl-1H-indol-3-yl)acetic acid, to obtain 1.2 mg of the title compound.

The mass spectrometry (MS) data for the obtained compound were as follows.

MS: m/z 1071.5 ($M^+$+23).

Example 128

Synthesis of tris[4-[β-amino-N-[2-(1H-indol-3-yl)acetyl]-L-alanyl]aminophenyl]methane trifluoroacetate The tris[4-(β-benzyloxycarbonylamino-L-alanyl)aminophenyl]methane obtained in Reference Example 74

(⅕ of the total amount obtained in Reference Example 74), 2-(1H-indol-3-yl)acetic acid (53 mg) and N-methylmorpholine (31 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 18 hours. The reaction mixture was poured into water (8 ml) and shaken. This was then centrifuged, and the supernatant was removed. After adding saturated sodium bicarbonate water (8 ml) to the residue and stirring, the mixture was centrifuged and the supernatant was removed. The procedure of centrifugation- and removal of the supernatant was then carried out once with saturated sodium bicarbonate water (8 ml) and twice with water (8 ml). The residue was dried under reduced pressure to obtain tris[4-[β-benzyloxycarbonylamino-N-[2-(1H-indol-3-yl)acetyl]-L-alanyl]aminophenyl]methane.

The tris[4-[β-benzyloxycarbonylamino-N-[2-(1H-indol-3-yl)acetyl]-L-alanyl]aminophenyl]methane (70 mg) was dissolved in a mixed solvent of methanol (4 ml) and N,N-dimethylformamide (4 ml), 10% palladium carbon (25 mg) was added, and then the mixture was stirred for 3 days at room temperature under a hydrogen atmosphere. The reaction mixture was filtered and the filtrate was concentrated under reduced pressure. A portion of the residue was purified by preparative high performance liquid chromatography using methanol/trifluoroacetic acid (100/0.1) and water/trifluoroacetic acid (100/0.1) as a mixed eluent, to obtain 3.5 mg of the title compound.

The mass spectrometry (MS) data for the obtained compound were as follows.

MS: m/z 1019.5 ($M^+$+1).

Example 129

Synthesis of tris[4-[β-amino-N-[2-(2-methyl-1H-indol-3-yl)acetyl]-L-alanyl]aminophenyl]methane trifluoroacetate Reaction was conducted in the same manner as Example 128, except that 2-(2-methyl-1H-indol-3-yl)acetic acid was used instead of 2-(1H-indol-3-yl)acetic acid, to obtain 2.9 mg of the title compound.

The mass spectrometry (MS) data for the obtained compound were as follows.

MS: m/z 1061.6 ($M^+$+1), 1083.6 ($M^+$+23).

Example 130

Synthesis of tris[4-[β-amino-N-[2-(5-methoxy-2-methyl-1H-indol-3-yl)acetyl]-L-alanyl]aminophenyl] methane trifluoroacetate Reaction was conducted in the same manner as Example 128, except that 2-(5-methoxy-2-methyl-1H-indol-3-yl) acetic acid was used instead of 2-(1H-indol-3-yl)acetic acid, to obtain 3.0 mg of the title compound.

The mass spectrometry (MS) data for the obtained compound were as follows.

MS: m/z 1151.6 ($M^+$+1), 1173.7 ($M^+$+23).

Example 131

Synthesis of tris[4-[β-aminomethyl-N-[2-(1H-indol-3-yl)acetyl]-L-alanyl]aminophenyl]methane trifluoroacetate The tris[4-(β-benzyloxycarbonylaminomethyl-L-alanyl) aminophenyl]methane.hydrochloride obtained in Reference Example 75 (1/5 of the total amount obtained in Reference Example 75), 2-(1H-indol-3-yl)acetic acid (53 mg) and N-methylmorpholine (62 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 18 hours. The reaction mixture was poured into water (8 ml) and shaken. This was then centrifuged, and the supernatant was removed. After adding saturated sodium bicarbonate water (8 ml) to the residue and stirring, the mixture was centrifuged and the supernatant was removed. The procedure of centrifugation and removal of the supernatant was then carried out once with saturated sodium bicarbonate water (8 ml) and twice with water (8 ml). The residue was dried under reduced pressure to obtain tris[4-[β-benzyloxycarbonylamino methyl-N-[2-(1H-indol-3-yl) acetyl]-L-alanyl]aminophenyl]methane.

The tris[4-[β-benzyloxycarbonylaminomethyl-N-[2(1H-indol-3-yl)acetyl]-L-alanyl]aminophenyl]methane (70 mg) was dissolved in a mixed solvent of methanol (4 ml) and N,N-dimethylformamide (4 ml), 10% palladium carbon (25 mg) was added, and then the mixture was stirred for 3 days at room temperature under a hydrogen atmosphere. The reaction mixture was filtered and the filtrate was concentrated under reduced pressure. A portion of the residue was purified by preparative high performance liquid chromatography using methanol/trifluoroacetic acid (100/0.1) and water/trifluoroacetic acid (100/0.1) as a mixed eluent, to obtain 2.9 mg of the title compound.

The mass spectrometry (MS) data for the obtained compound were as follows.

MS: m/z 1061.5 ($M^+$+1).

Example 132

Synthesis of tris[4-[β-aminomethyl-N-[2-(2-methyl-1H-indol-3-yl)acetyl]-L-alanyl]aminophenyl] methane trifluoroacetate Reaction was conducted in the same manner as Example 131, except that 2-(2-methyl-1H-indol-3-yl)acetic acid was used instead of 2-(1H-indol-3-yl)acetic acid, to obtain 2.4 mg of the title compound.

The mass spectrometry (MS) data for the obtained compound were as follows.

MS: m/z 1103.6 ($M^+$+1).

Example 133

Synthesis of tris[4-[β-aminomethyl-N-[2-(5-methoxy-2-methyl-1H-indol-3-yl)acetyl]-L-alanyl] aminophenyl]methane trifluoroacetate Reaction was conducted in the same manner as Example 131, except that 2-(5-methoxy-2-methyl-1H-indol-3-yl) acetic acid was used instead of 2-(1H-indol-3-yl)acetic acid, to obtain 3.8 mg of the title compound.

The mass spectrometry (MS) data for the obtained compound were as follows.

MS: m/z 1193.6 ($M^+$+1).

Example 134

Synthesis of tris[4-[N-α-[2-(1H-indol-3-yl)acetyl]-L-ornithyl]aminophenyl]methane trifluoroacetate The tris[4-[N-δ-benzyloxycarbonyl-L-ornithyl] aminophenyl]methane-hydrochloride obtained in Reference Example 76 (⅕ of the total amount obtained in Reference Example 76), 2-(1H-indol-3-yl)acetic acid (53 mg) and N-methylmorpholine (62 mg) were dissolved in N,N-dimethylformamide (2 ml), after which an N,N-dimethylformamide solution containing O-(7-azabenzotriazol-1-yl)-1,1,3,3-tetramethyluronium hexafluorophosphate (0.2 M, 1.5 ml) was added while cooling on ice, the temperature was raised to room temperature, and the mixture was stirred for 18 hours. The reaction mixture was poured into water (8 ml) and shaken. This was then centrifuged, and the supernatant was removed. After adding saturated sodium bicarbonate water (8 ml) to the residue and stirring, the mixture was centrifuged and the supernatant was removed. The procedure of centrifugation and removal of the supernatant was then carried out once with saturated sodium bicarbonate water (8 ml) and twice with water (8 ml). The residue was dried under reduced pressure to obtain tris[4-[N-δ-benzyloxycarbonyl-N-α-[2-(1H-indol-3-yl)acetyl]-L-ornithyl]aminophenyl]methane.

The tris[4-[N-δ-benzyloxycarbonyl-N-α-[2-(1H-indol-3-yl)acetyl]-L-ornithyl]aminophenyl]methane (70 mg) was dissolved in a mixed solvent of methanol (4 ml) and N,N-dimethylformamide (4 ml), 10% palladium carbon (25 mg) was added, and then the mixture was stirred for 3 days at room temperature under a hydrogen atmosphere. The reaction mixture was filtered and the filtrate was concentrated under reduced pressure. A portion of the residue was purified by preparative high performance liquid chromatography using methanol/trifluoroacetic acid (100/0.1) and water/trifluoroacetic acid (100/0.1) as a mixed eluent, to obtain 3.7 mg of the title compound.

The mass spectrometry (MS) data for the obtained compound were as follows.

MS: m/z 1103.7 (M$^+$+1).

Example 135

Synthesis of tris[4-[N-α-[2-(5-methoxy-2-methyl-1H-indol-3-yl)acetyl]-L-ornithyl]aminophenyl]methane trifluoroacetate Reaction was conducted in the same manner as Example 134, except that-2-(5-methoxy-2-methyl-1H-indol-3-yl)acetic acid was used instead of 2-(1H-indol-3-yl)acetic acid, to obtain 4.2 mg of the title compound.

The mass spectrometry (MS) data for the obtained compound were as follows.

MS: m/z 1235.7 (M$^+$+1).

Example 136

Synthesis of tris[4-[N-α-[2-(5-methyl-1H-indol-3-yl)acetyl]-D-lysyl]aminophenyl]methane hydrochloride The tris[4-(N-ε-benzyloxycarbonyl-D-lysyl)aminophenyl]methane (54 mg) obtained in Reference Example 25, the (5-methyl-1H-indol-3-yl)acetic acid (30 mg) obtained in Reference Example 78 and N-methylmorpholine (16 mg) were dissolved in N,N-dimethylformamide (1 ml), after which an N,N-dimethylformamide solution containing O-(7-azabenzotriazol-1-yl)-1,1,3,3-tetramethyluronium hexafluorophosphate (0.315 M, 0.5 ml) was added while cooling on ice, the temperature was raised to room temperature, and the mixture was stirred for 24 hours. The reaction mixture was poured into water (5 ml) and shaken. This was then centrifuged, and the supernatant was removed. After adding saturated sodium bicarbonate water (5 ml) to the residue and stirring, the mixture was centrifuged and the supernatant was removed. The procedure of centrifugation and removal of the supernatant was again carried out with addition of water (5 ml). The residue was dried under reduced pressure to obtain tris[4-[N-ε-benzyloxycarbonyl-N-α-[(5-methyl-1H-indol-3-yl)acetyl]-D-lysyl]aminophenyl]methane.

The tris[4-[N-ε-benzyloxycarbonyl-N-α-[(5-methyl-1H-indol-3-yl)acetyl]-D-lysyl]aminophenyl]methane (the total amount obtained in the previous reaction) was dissolved in a mixed solvent of methanol (2 ml) and N,N-dimethylformamide (2.5 ml), 10% palladium carbon (22 mg) was added, and then the mixture was stirred for 3 days at room temperature under a hydrogen atmosphere. The reaction mixture was filtered and the filtrate was concentrated under reduced pressure. A portion of the residue was purified by preparative high performance liquid chromatography using methanol/trifluoroacetic acid (100/0.1) and water/trifluoroacetic acid (100/0.1) as a mixed eluent. After dissolution in methanol (0.5 ml), an excess of 0.5 N hydrochloric acid was added and the mixture was concentrated under reduced pressure to obtain 2.5 mg of the title compound.

The mass spectrometry (MS) data for the obtained compound were as follows.

MS: m/z 1187.7 (M$^+$+1).

Example 137

Synthesis of tris[4-[N-α-[2-(4-methyl-1H-indol-3-yl)acetyl]-D-lysyl]aminophenyl]methane hydrochloride Reaction was conducted in the same manner as Example 136, except that the 2-(4-methyl-1H-indol-3-yl)acetic acid obtained in Reference Example 91 was used instead of 2-(5-methyl-1H-indol-3-yl)acetic acid, to obtain 1.2 mg of the title compound.

The mass spectrometry (MS) data for the obtained compound were as follows.

MS: m/z 1187.7 (M$^+$+1).

Example 138

Synthesis of tris[4-[N-α-[2-(5-trifluoromethyl-1H-indol-3-yl)acetyl]-D-lysyl]aminophenyl]methane hydrochloride Reaction was conducted in the same manner as Example 136, except that the 2-(5-trifluoromethyl-1H-indol-3-yl)acetic acid obtained in Reference Example 77 was used instead of 2-(5-methyl-1H-indol-3-yl)acetic acid, to obtain 1.4 mg of the title compound.

The mass spectrometry (MS) data for the obtained compound were as follows.

MS: m/z 1349.6 (M$^+$+1).

Example 139

Synthesis of tris[4-[N-α-[2-(6-trifluoromethyl-1H-indol-3-yl)acetyl]-D-lysyl]aminophenyl]methane hydrochloride Reaction was conducted in the same manner as Example 136, except that the 2-(6-trifluoromethyl-1H-indol-3-yl) acetic acid obtained in Reference Example 90 was used instead of 2-(5-methyl-1H-indol-3-yl)acetic acid, to obtain 3.3 mg of the title compound.

The mass spectrometry (MS) data for the obtained compound were as follows.

MS: m/z 1349.7 (M$^+$+1).

Example 140

Synthesis of tris[4-[N-α-[2-(2,5-dimethyl-1H-indol-3-yl)acetyl]-D-lysyl]aminophenyl]methane hydrochloride Reaction was conducted in the same manner as Example 136, except that the 2-(2,5-dimethyl-1H-indol-3-yl)acetic acid obtained in Reference Example 82 was used instead of 2-(5-methyl-1H-indol-3-yl)acetic acid, to obtain 6.9 mg of the title compound.

The mass spectrometry (MS) data for the obtained compound were as follows.

MS: m/z 1229.6 (M$^+$+1).

Example 141

Synthesis of tris[4-[N-α-[2-(2-methyl-5-trifluoromethyl-1H-indol-3-yl)acetyl]-D-lysyl]aminophenyl]methane hydrochloride Reaction was conducted in the same manner as Example 136, except that the 2-(2-methyl-5-trifluoromethyl-1H-indol-3-yl)acetic acid obtained in Reference Example 95 was used instead of 2-(5-methyl-1H-indol-3-yl)acetic acid, to obtain 7.5 mg of the title compound.

The mass spectrometry (MS) data for the obtained compound were as follows.

MS: m/z 1391.7 (M$^+$+1).

Example 142

Synthesis of tris[4-[N-α-[2-(5-isopropyl-2-methyl-1-H-indol-3-yl)acetyl]-D-lysyl]aminophenyl]methane hydrochloride Reaction was conducted in the same manner as Example 136, except that the 2-(5-isopropyl-2-methyl-1H-indol-3-yl)acetic acid obtained in Reference Example 85 was used instead of 2-(5-methyl-1H-indol-3-yl)acetic acid, to obtain 8.0 mg of the title compound.

The mass spectrometry (MS) data for the obtained compound were as follows.

MS: m/z 1313.8 (M$^+$+1).

Example 143

Synthesis of tris[4-[N-α-[2-(2-methyl-5-trifluoromethoxy-1H-indol-3-yl)acetyl]-D-lysyl]aminophenyl]methane hydrochloride Reaction was conducted in the same manner as Example 136, except that the 2-(2-methyl-5-trifluoromethoxy-1H-indol-3-yl)acetic acid obtained in Reference Example 81 was used instead of 2-(5-methyl-1H-indol-3-yl)acetic acid, to obtain 6.3 mg of the title compound.

The mass spectrometry (MS) data for the obtained compound were as follows.

MS: m/z 1439.7 (M$^+$+1).

Example 144

Synthesis of tris[4-[N-α-[2-(2,6-dimethyl-1H-indol-3-yl)acetyl]-D-lysyl]aminophenyl]methane hydrochloride Reaction was conducted in the same manner as Example 136, except that the 2-(2,6-dimethyl-1H-indol-3-yl)acetic acid obtained in Reference Example 86 was used instead of 2-(5-methyl-1H-indol-3-yl)acetic acid, to obtain 4.4 mg of the title compound.

The mass spectrometry (MS) data for the obtained compound were as follows.

MS: m/z 1229.7 (M$^+$+1).

Example 145

Synthesis of tris[4-[N-α-[2-(2-methyl-6-trifluoro-1H-indol-3-yl)acetyl]-D-lysyl]aminophenyl]methane hydrochloride Reaction was conducted in the same manner as Example 136, except that the 2-(2-methyl-6-trifluoro-1H-indol-3-yl) acetic acid obtained in Reference Example 94 was used instead of 2-(5-methyl-1H-indol-3-yl)acetic acid, to obtain 7.6 mg of the title compound.

The mass spectrometry (MS) data for the obtained compound were as follows.

MS: m/z 1391.7 (M$^+$+1).

Example 146

Synthesis of tris[4-[N-α-[2-(6-methoxy-2-methyl-1H-indol-3-yl)acetyl]-D-lysyl]aminophenyl]methane hydrochloride Reaction was conducted in the same manner as Example 136, except that the 2-(6-methoxy-2-methyl-1H-indol-3-yl) acetic acid obtained in Reference Example 88 was used instead of 2-(5-methyl-1H-indol-3-yl)acetic acid, to obtain 3.8 mg of the title compound.

The mass spectrometry (MS) data for the obtained compound were as follows.

MS: m/z 1277.6 (M$^+$+1).

Example 147

Synthesis of tris[4-[N-α-[2-(2,7-dimethyl-1H-indol-3-yl)acetyl]-D-lysyl]aminophenyl]methane hydrochloride Reaction was conducted in the same manner as Example 136, except that the 2-(2,7-dimethyl-1H-indol-3-yl)acetic acid obtained in Reference Example 83 was used instead of 2-(5-methyl-1H-indol-3-yl)acetic acid, to obtain 6.5 mg of the title compound.

The mass spectrometry (MS) data for the obtained compound were as follows.

MS: m/z 1229.7 (M$^+$+1).

Example 148

Synthesis of tris[4-[N-α-[2-(2-ethyl-1H-indol-3-yl) acetyl]-D-lysyl]aminophenyl]methane hydrochloride Reaction was conducted in the same manner as Example 136, except that the 2-(2-ethyl-1H-indol-3-yl)acetic acid obtained in Reference Example 89 was used instead of 2-(5-methyl-1H-indol-3-yl)acetic acid, to obtain 2.0 mg of the title compound.

The mass spectrometry (MS) data for the obtained compound were as follows.

MS: m/z 1229.7 (M$^+$+1).

Example 149

Synthesis of tris[4-[N-α-[2-(1H-indol-3-yl)acetyl]-D-lysyl]aminophenyl]methane hydrochloride Reaction was conducted in the same manner as Example 136, except that indole-3-acetic acid used instead of 2-(5- methyl-1H-indol-3-yl)acetic acid, to obtain 2.1 mg of the title compound.

The NMR data and mass spectrometry (MS) data for the obtained compound were as follows.

NMR: (270 MHz, CD$_3$OD) δ: 1.1–2.0 (18H,m), 2.6–2.9 (6H,m), 3.76 (6H,ABq,J=18.6 Hz,2.1 Hz), 4.4–4.7 (3H,m), 5.42 (1H,s), 6.8–7.9 (27H,m).

MS: m/z 1145.4 (M$^+$+1).

Example 150

Synthesis of tris[4-[N-α-(1H-indol-2-yl)carbonyl-D-lysyl]aminophenyl]methane hydrochloride Reaction was conducted in the same manner as Example 136, except that indole-2-carboxylic acid was used instead of 2-(5-methyl-1H-indol-3-yl)acetic acid, to obtain 4.8 mg of the title compound.

The mass spectrometry (MS) data for the obtained compound were as follows.

MS: m/z 1103.7 (M$^+$+1).

Example 151

Synthesis of tris[4-[N-α-(5-hydroxy-1H-indol-2-yl)carbonyl-D-lysyl]aminophenyl]methane hydrochloride Reaction was conducted in the same manner as Example 136, except that 5-hydroxyindole-2-carboxylic acid was used instead of 2-(5-methyl-1H-indol-3-yl)acetic acid, to obtain 4.9 mg of the title compound.

The mass spectrometry (MS) data for the obtained compound were as follows.

MS: m/z 1151.6 (M$^+$+1).

Example 152

Synthesis of tris[4-[N-α-(1H-indol-4-yl)carbonyl-D-lysyl]aminophenyl]methane hydrochloride Reaction was conducted in the same manner as Example 136, except that indole-4-carboxylic acid was used instead of 2-(5-methyl-1H-indol-3-yl)acetic acid, to obtain 4.3 mg of the title compound.

The mass spectrometry (MS) data for the obtained compound were as follows.

MS: m/z 1103.6 (M$^+$+1).

Example 153

Synthesis of tris[4-[N-α-[2-hydroxy-3-(1H-indol-3-yl) propanoyl]-D-lysyl]aminophenyl]methane hydrochloride Reaction was conducted in the same manner as Example 136, except that 2-hydroxy-3-(1H-indol-3-yl)propanoic acid was used instead of 2-(5-methyl-1H-indol-3-yl)acetic acid, to obtain 3.0 mg of the title compound.

The mass spectrometry (MS) data for the obtained compound were as follows.

MS: m/z 1235.7 (M$^+$+1).

Example 154

Synthesis of tris[4-[N-α-[2-(6-methyl-1H-indol-3-yl)acetyl]-D-lysyl]aminophenyl]methane hydrochloride Reaction was conducted in the same manner as Example 136, except that the 2-(6-methyl-1H-indol-3-yl)acetic acid obtained in Reference Example 92 was used instead of 2-(5-methyl-1H-indol-3-yl)acetic acid, to obtain 1.0 mg of the title compound.

The mass spectrometry (MS) data for the obtained compound were as follows.

MS: m/z 1187.6 (M$^+$+1).

Example 155

Synthesis of tris[4-[N-α-[2-(7-methyl-1H-indol-3-yl)acetyl]-D-lysyl]aminophenyl]methane hydrochloride Reaction was conducted in the same manner as Example 136, except that the 2-(7-methyl-1H-indol-3-yl)acetic acid obtained in Reference Example 79 was used instead of 2-(5-methyl-1H-indol-3-yl)acetic acid, to obtain 0.8 mg of the title compound.

The mass spectrometry (MS) data for the obtained compound were as follows.

MS: m/z 1187.6 (M$^+$+1).

Example 156

Synthesis of tris[4-[N-α-(5-methyl-1-phenylpyrazol-4-yl)carbonyl-D-lysyl]aminophenyl]methane hydrochloride The tris[4-(N-ε-t-butoxycarbonyl-D-lysyl)aminophenyl]methane (49 mg) obtained in Reference Example 28, 5-methyl-1-phenylpyrazole-4-carboxylic acid (32 mg) and N-methylmorpholine (16 mg) were dissolved in N,N-dimethylformamide (1 ml), after which an N,N-dimethylformamide solution containing O-(7-azabenzotriazol-1-yl)-1,1,3,3-tetramethyluronium hexafluorophosphate (0.315 M, 0.5 ml) was added while cooling on ice, the temperature was raised to room temperature, and the mixture was stirred for 24 hours. The reaction mixture was poured into water (5 ml) and shaken. This was then centrifuged, and the supernatant was removed. After adding saturated sodium bicarbonate water (5 ml) to the residue and stirring, the mixture was centrifuged and the supernatant was removed. The procedure of centrifugation and removal of the supernatant was again carried out with addition of water (5 ml). The residue was dried under reduced pressure to obtain tris[4-[N-ε-t-butoxycarbonyl-N-α-(5-methyl-1-phenylpyrazol-4-yl) carbonyl-D-lysyl]aminophenyl]methane.

The tris[4-[N-ε-t-butoxycarbonyl-N-α-(5-methyl-1-phenylpyrazol-4-yl)carbonyl-D-lysyl]aminophenyl] methane (the total amount obtained in the previous reaction) was dissolved in methanol (1.5 ml), a 4 N hydrochloric acid/dioxane solution (1.5 ml) was added dropwise while cooling on ice, the temperature was raised to room temperature, and the mixture was shaken for 4 hours. The reaction mixture was concentrated under reduced pressure, and a portion of the residue was purified by preparative high performance liquid chromatography using methanol/trifluoroacetic acid (100/0.1) and water/trifluoroacetic acid (100/0.1) as a mixed eluent. After dissolution in methanol (0.5 ml), an excess of 0.5 N hydrochloric acid was added and the mixture was concentrated under reduced pressure to obtain 3.3 mg of the title compound.

The mass spectrometry (MS) data for the obtained compound were as follows.

MS: m/z 1226.7 (M$^+$+1).

Example 157

Synthesis of tris[4-[N-α-(pyrazin-2-yl)carbonyl-D-lysyl]aminophenyl]methane hydrochloride Reaction was conducted in the same manner as Example 156, except that 2-pyrazinecarboxylic acid was used instead of 5-methyl-1-phenylpyrazole-4-carboxylic acid, to obtain 7.7 mg of the title compound.

The mass spectrometry (MS) data for the obtained compound were as follows.

MS: m/z 992.6 (M$^+$+1).

Example 158

Synthesis of tris[4-[N-α-[4-(3-methyl-5-oxo-2-pyrazolin-1-yl)benzoyl]carbonyl-D-lysyl]aminophenyl]methane hydrochloride Reaction was conducted in the same manner as Example 156, except that 4-(3-methyl-5-oxo-2-pyrazolin-1-yl) benzoic acid was used instead of 5-methyl-1-phenylpyrazole-4-carboxylic acid, to obtain 6.2 mg of the title compound.

The mass spectrometry (MS) data for the obtained compound were as follows.

MS: m/z 1274.6 (M$^+$+1).

Example 159

Synthesis of tris[4-[N-α-[2-(3-hydroxyphenyl)acetyl]-D-lysyl]aminophenyl]methane hydrochloride Reaction was conducted in the same manner as Example 156, except that 3-hydroxyphenylacetic acid was used instead of 5-methyl-1-phenylpyrazole-4-carboxylic acid, to obtain 6.4 mg of the title compound.

The mass spectrometry (MS) data for the obtained compound were as follows.

MS: m/z 1076.6 (M$^+$+1).

Example 160

Synthesis of tris[4-[N-α-(D-tyrosyl)-D-lysyl]aminophenyl]methane hydrochloride

Reaction w as conducted in the same manner as Example 156, except that N-t-butoxycarbonyl-D-tyrosine was used instead of 5-methyl-1-phenylpyrazole-4-carboxylic acid, to obtain 7.1 mg of the title compound.

The mass spectrometry (MS) data for the obtained compound were as follows.

MS: m/z 1163.8 (M$^+$+1).

Example 161

Synthesis of tris[4-[N-α-(D-tryptophyl)-D-lysyl]aminophenyl]methane hydrochloride Reaction was conducted in the same manner as Example 156, except that N-t-butoxycarbonyl-D-tryptophan was used instead of 5-methyl-1-phenylpyrazole-4-carboxylic acid, to obtain 15.2 mg of the title compound.

The mass spectrometry (MS) data for the obtained compound were as follows.

MS: m/z 1232.7 (M$^+$+1).

Example 162

Synthesis of tris[4-[N-α-[2-(tetrazol-1-yl)acetyl]-D-lysyl]aminophenyl]methane hydrochloride Reaction was conducted in the same manner as Example 156, except that 1-tetrazoleacetic acid was used instead of 5-methyl-1-phenylpyrazole-4-carboxylic acid, to obtain 3.5 mg of the title compound.

The mass spectrometry (MS) data for the obtained compound were as follows.

MS: m/z 1004.5 (M$^+$+1).

Example 163

Synthesis of tris[4-[N-α-[2-(3-methylisooxazol-5-yl)acetyl]-D-lysyl]aminophenyl]methane hydrochloride Reaction was conducted in the same manner as Example 156, except that 2-(3-methylisooxazol-5-yl)acetic acid was used instead of 5-methyl-1-phenylpyrazole-4-carboxylic acid, to obtain 7.2 mg of the title compound.

The mass spectrometry (MS) data for the obtained compound were as follows.

MS: m/z 1043.6 (M$^+$+1).

Example 164

Synthesis of tris[4-[N-α-[2-(thiophen-2-yl)acetyl]-D-lysyl]aminophenyl]methane hydrochloride Reaction was conducted in the same manner as Example 156, except that 2-(thiophen-2-yl)acetic acid was used instead of 5-methyl-1-phenylpyrazole-4-carboxylic acid, to obtain 10.3 mg of the title compound.

The mass spectrometry (MS) data for the obtained compound were as follows.

MS: m/z 1046.5 (M$^+$+1).

Example 165

Synthesis of tris[4-[N-α-[2-(hydantoin-5-yl)acetyl]-D-lysyl]aminophenyl]methane hydrochloride Reaction was conducted in the same manner as Example 156, except that 2-(hydantoin-5-yl)acetic acid was used instead of 5-methyl-1-phenylpyrazole-4-carboxylic acid, to obtain 3.0 mg of the title compound.

The mass spectrometry (MS) data for the obtained compound were as follows.

MS: m/z 1094.6 (M$^+$+1).

Example 166

Synthesis of tris[4-[N-α-[2-(uracil-4-yl)acetyl]-D-lysyl]aminophenyl]methane hydrochloride Reaction was conducted in the same manner as Example 156, except that 2-(uracil-4-yl)acetic acid was used instead of 5-methyl-1-phenylpyrazole-4-carboxylic acid, to obtain 2.7 mg of the title compound.

The mass spectrometry (MS) data for the obtained compound were as follows.

MS: m/z 1130.6 (M$^+$+1).

Example 167

Synthesis of tris[4-[N-α-[2-(rhodanin-3-yl)acetyl]-D-lysyl]aminophenyl]methane hydrochloride Reaction was conducted in the same manner as Example 156, except that N-carboxymethylrhodanine was used instead of 5-methyl-1-phenylpyrazole-4-carboxylic acid, to obtain 11.2 mg of the title compound.

Example 168

Synthesis of tris[4-[N-α-(4-acetylaminobutanoyl)-D-lysyl]aminophenyl]methane hydrochloride Reaction was conducted in the same manner as Example 156, except that 4-acetylaminobutanoic acid was used instead of 5-methyl-1-phenylpyrazole-4-carboxylic acid, to obtain 6.0 mg of the title compound.

The mass spectrometry (MS) data for the obtained compound were as follows.

MS: m/z 1055.7 ($M^+$+1).

Example 169

Synthesis of tris[4-[N-α-(2-aminoacetyl)-D-lysyl]aminophenyl]methane hydrochloride Reaction was conducted in the same manner as Example 156, except that N-t-butoxycarbonylglycine was used instead of 5-methyl-1-phenylpyrazole-4-carboxylic acid, to obtain 4.0 mg of the title compound.

The mass spectrometry (MS) data for the obtained compound were as follows.

MS: m/z 845.6 ($M^+$+1).

Example 170

Synthesis of tris[4-[N-α-(4-aminobutanoyl)-D-lysyl]aminophenyl]methane hydrochloride Reaction was conducted in the same manner as Example 156, except that N-t-butoxycarbonyl-4-aminobutanoic acid was used instead of 5-methyl-1-phenylpyrazole-4-carboxylic acid, to obtain 2.4 mg of the title compound.

The mass spectrometry (MS) data for the obtained compound were as follows.

MS: m/z 929.6 ($M^+$+1).

Example 171

Synthesis of tris[4-[N-α-(4-hydroxymethylbenzoyl)-D-lysyl]aminophenyl]methane hydrochloride Reaction was conducted in the same manner as Example 156, except that 4-hydroxymethylbenzoic acid was used instead of 5-methyl-1-phenylpyrazole-4-carboxylic acid, to obtain 1.0 mg of the title compound.

The mass spectrometry (MS) data for the obtained compound were as follows.

MS: m/z 1076.5 ($M^+$+1).

Example 172

Synthesis of tris[4-[N-α-[2-(pyridin-2-yl)acetyl]-D-lysyl]aminophenyl]methane hydrochloride Reaction was conducted in the same manner as Example 156, except that 2-(pyridin-2-yl)acetic acid hydrochloride was used instead of 5-methyl-1-phenylpyrazole-4-carboxylic acid, to obtain 1.9 mg of the title compound.

The mass spectrometry (MS) data for the obtained compound were as follows.

MS: m/z 1031.6 ($M^+$+1).

Example 173

Synthesis of tris[4-[N-α-[2-(pyridin-4-yl)acetyl]-D-lysyl]aminophenyl]methane hydrochloride Reaction was conducted in the same manner as Example 156, except that 2-(pyridin-4-yl)acetic acid hydrochloride was used instead of 5-methyl-1-phenylpyrazole-4-carboxylic acid, to obtain 1.0 mg of the title compound.

The mass spectrometry (MS) data for the obtained compound were as follows.

MS: m/z 763.5, 1031.5 ($M^+$+1).

Example 174

Synthesis of tris[4-[N-α-(3-aminopropanoyl)-D-lysyl]aminophenyl]methane hydrochloride Reaction was conducted in the same manner as Example 156, except that N-t-butoxycarbonyl-β-alanine was used instead of 5-methyl-1-phenylpyrazole-4-carboxylic acid, to obtain 4.0 mg of the title compound.

The mass spectrometry (MS) data for the obtained compound were as follows.

MS: m/z 887.6 ($M^+$+1).

Example 175

Synthesis of tris[4-[N-α-(2-hydroxycarbonylacetyl)-D-lysyl]aminophenyl]methane hydrochloride Reaction was conducted in the same manner as Example 156, except that mono-t-butyl malonate was used instead of 5-methyl-1-phenylpyrazole-4-carboxylic acid, to obtain 1.3 mg of the title compound.

The mass spectrometry (MS) data for the obtained compound were as follows.

MS: m/z 932.3 ($M^+$+1).

Example 176

Synthesis of tris[4-[N-α-[2-(5-chloro-1H-indol-3-yl)acetyl]-D-lysyl]aminophenyl]methane hydrochloride Reaction was conducted in the same manner as Example 156, except that the 2-(5-chloro-1H-indol-3-yl)acetic acid obtained in Reference Example 80 was used instead of 5-methyl-1-phenylpyrazole-4-carboxylic acid, to obtain 4.8 mg of the title compound.

The mass spectrometry (MS) data for the obtained compound were as follows.

MS: m/z 1247.5 ($M^+$+1), 1249.4.

Example 177

Synthesis of tris[4-[N-α-[2-(6-chloro-1H-indol-3-yl)acetyl]-D-lysyl]aminophenyl]methane hydrochloride Reaction was conducted in the same manner as Example 156, except that the 2-(6-chloro-1H-indol-3-yl)acetic acid obtained in Reference Example 93 was used instead of 5-methyl-1-phenylpyrazole-4-carboxylic acid, to obtain 4.2 mg of the title compound.

The mass spectrometry (MS) data for the obtained compound were as follows.

MS: m/z 1247.4 ($M^+$+1), 1249.4.

Example 178

Synthesis of tris[4-[N-α-[2-(5-chloro-2-methyl-1-H-indol-3-yl)acetyl]-D-lysyl]aminophenyl]methane hydrochloride Reaction was conducted in the same manner as Example 156, except that the 2-(5-chloro-2-methyl-1H-indol-3-yl)

---

The mass spectrometry (MS) data for the obtained compound were as follows.

MS: m/z 1193.4 ($M^+$+1).

acetic acid obtained in Reference Example 84 was used instead of 5-methyl-1-phenylpyrazole-4-carboxylic acid, to obtain 4.3 mg of the title compound.

The mass spectrometry (MS) data for the obtained compound were as follows.

MS: m/z 1289.5 ($M^+$+1), 1291.5.

Example 179

Synthesis of tris[4-[N-α-[2-(6-chloro-2-methyl-1H-indol-3-yl)acetyl]-D-lysyl]aminophenyl]methane hydrochloride Reaction was conducted in the same manner as Example 156, except that the 2-(2-(6-chloro-2-methyl-1H-indol-3-yl) acetic acid obtained in Reference Example 87 was used instead of 5-methyl-1-phenylpyrazole-4-carboxylic acid, to obtain 4.5 mg of the title compound.

The mass spectrometry (MS) data for the obtained compound were as follows.

MS: m/z 1289.5 ($M^+$+1), 1291.5.

Example 180

Synthesis of tris[4-[N-α-(1,4-benzodioxan-2-yl) carbonyl-D-lysyl]aminophenyl]methane hydrochloride Reaction was conducted in the same manner as Example 156, except that 1,4-benzodioxane-2-carboxylic acid was used instead of 5-methyl-1-phenylpyrazole-4-carboxylic acid, to obtain 5.2 mg of the title compound.

The mass spectrometry (MS) data for the obtained compound were as follows.

MS: m/z 1160.5 ($M^+$+1).

Example 181

Synthesis of tris[4-(N-α-benzenesulfonyl-D-lysyl) aminophenyl]methane hydrochloride The tris[4-(N-ε-t-butoxycarbonyl-D-lysyl)aminophenyl] methane (49 mg) obtained in Reference Example 28 and benzenesulfonyl chloride (53 mg) were dissolved in N,N-dimethylformamide (1 ml), after which N-methylmorpholine (31 mg) was added while cooling on ice, the temperature was raised to room temperature, and the mixture was stirred for 92 hours. The reaction mixture was poured into water (5 ml) and shaken. This was then centrifuged, and the supernatant was removed. After adding saturated sodium bicarbonate water (5 ml) to the residue and stirring, the mixture was centrifuged and the supernatant was removed. The procedure of centrifugation and removal of the supernatant was again carried out with water (5 ml). The residue was dried under reduced pressure to obtain tris[4-(N-α-benzenesulfonyl-N-ε-t-butoxycarbonyl-D-lysyl)aminophenyl]methane.

The tris[4-(N-α-benzenesulfonyl-N-α-t-butoxycarbonyl-D-lysyl)aminophenyl]methane (the total amount obtained in the previous reaction) was dissolved in methanol (1.5 ml), a 4 N hydrochloric acid/dioxane solution (1.5 ml) was added dropwise while cooling on ice, the temperature was raised to room temperature, and the mixture was shaken for 3 hours. The reaction mixture was concentrated under reduced pressure, and a portion of the residue was purified by preparative high performance liquid chromatography using methanol/trifluoroacetic acid (100/0.1) and water/trifluoroacetic acid (100/0.1) as a mixed eluent. After dissolution in methanol (0.5 ml), an excess of 0.5 N hydrochloric acid was added and the mixture was concentrated under reduced pressure to obtain 3.4 mg of the title compound.

The mass spectrometry (MS) data for the obtained compound were as follows.

MS: m/z 1094.5 ($M^+$+1).

Example 182

Synthesis of tris[4-[N-α-(thiophen-2-yl)sulfonyl-D-lysyl]aminophenyl]methane hydrochloride Reaction was conducted in the same manner as Example 181, except that 2-thiophenesulfonyl chloride was used instead of benzenesulfonyl chloride, to obtain 5.0 mg of the title compound.

The mass spectrometry (MS) data for the obtained compound were as follows.

MS: m/z 1112.3 ($M^+$+1).

Example 183

Synthesis of tris[4-(N-α-benzylsulfonyl-D-lysyl) aminophenyl]methane hydrochloride Reaction was conducted in the same manner as Example 181, except that benzylsulfonyl chloride was used instead of benzenesulfonyl chloride, to obtain 4.4 mg of the title compound.

The mass spectrometry (MS) data for the obtained compound were as follows.

MS: m/z 1136.5 ($M^+$+1).

Example 184

Synthesis of tris[4-[N-α-(2-acetylamino-4-methylthiazol-5-yl)sulfonyl-D-lysyl]aminophenyl] methane hydrochloride Reaction was conducted in the same manner as Example 181, except that (2-acetylamino-4-methylthiazol-5-yl) sulfonyl chloride was used instead of benzenesulfonyl chloride, to obtain 1.5 mg of the title compound.

The mass spectrometry (MS) data for the obtained compound were as follows.

MS: m/z 1328.2 ($M^+$+1).

Example 185

Synthesis of tris[4-[N-α-(2-hydroxybenzoyl)-D-lysyl]aminophenyl]methane trifluoroacetate The tris[4-(N-ε-t-butoxycarbonyl-D-lysyl)aminophenyl] methane (29 mg) obtained in Reference Example 28, 2-hydroxybenzoic acid (15 mg) and N-methylmorpholine (30 mg) were dissolved in N,N-dimethylformamide (1 ml), after which an N,N-dimethylformamide solution containing O-(7-azabenzotriazol-1-yl)-1,1,3,3-tetramethyluronium hexafluorophosphate (0.54 M, 0.2 ml) was added while cooling on ice, the temperature was raised to room temperature, and the mixture was stirred for 14 hours. The reaction mixture was poured into water (4 ml) and shaken. This was then centrifuged, and the supernatant was removed. After adding saturated sodium bicarbonate water (4 ml) to the residue and stirring, the mixture was centrifuged and the supernatant was removed. The procedure of centrifugation and removal of the supernatant was then carried out once with saturated sodium bicarbonate water (4 ml) and twice with water (4 ml). The residue was dried under reduced pressure to obtain tris[4-[N-ε-t-butoxycarbonyl-N-α-(2-hydroxybenzoyl)-D-lysyl]aminophenyl]methane.

The tris[4-[N-ε-t-butoxycarbonyl-N-α-(2-hydroxybenzoyl)-D-lysyl]aminophenyl]methane (the total amount obtained in the previous reaction) was dissolved in methanol (1 ml), a 4 N hydrochloric acid/dioxane solution (1 ml) was added dropwise while cooling on ice, the temperature was raised to room temperature, and the mixture was shaken for 1 hour. The reaction mixture was concentrated under reduced pressure, and a portion of the residue was purified by preparative high performance liquid chromatography using methanol/trifluoroacetic acid (100/0.1) and water/trifluoroacetic acid (100/0.1) as a mixed eluent, to obtain 1.1 mg of the title compound.

The mass spectrometry (MS) data for the obtained compound were as follows.

MS: m/z 1034.5 ($M^+$+1).

Example 186

Synthesis of tris[4-[N-α-(3-hydroxybenzoyl)-D-lysyl]aminophenyl]methane trifluoroacetate Reaction was conducted in the same manner as Example 185, except that 3-hydroxybenzoic acid was used instead of 2-hydroxybenzoic acid, to obtain 9.1 mg of the title compound.

The mass spectrometry (MS) data for the obtained compound were as follows.

MS: m/z 1034.5 ($M^+$+1).

Example 187

Synthesis of tris[4-[N-ε-(2-phenylacetyl)-D-lysyl]aminophenyl]methane trifluoroacetate Reaction was conducted in the same manner as Example 185, except that phenylacetic acid was used instead of 2-hydroxybenzoic acid, to obtain 16.6 mg of the title compound.

The mass spectrometry (MS) data for the obtained compound were as follows.

MS: m/z 1028.5 ($M^+$+1).

Example 188

Synthesis of tris[4-[N-α-[2-(3,4-dihydroxyphenyl)acetyl]-D-lysyl]aminophenyl]methane trifluoroacetate Reaction was conducted in the same manner as Example 185, except that 3,4-dihydroxyphenylacetic acid was used instead of 2-hydroxybenzoic acid, to obtain 14.5 mg of the title compound.

The mass spectrometry (MS) data for the obtained compound were as follows.

MS: m/z 1124.6 ($M^+$+1).

Example 189

Synthesis of tris[4-[N-α-[3-(2-hydroxyphenyl)propanoyl]-D-lysyl]aminophenyl]methane trifluoroacetate Reaction was conducted in the same manner as Example 185, except that 3-(2-hydroxyphenyl)propanoic acid was used instead of 2-hydroxybenzoic acid, to obtain 7.5 mg of the title compound.

The mass spectrometry (MS) data for the obtained compound were as follows.

MS: m/z 1118.6 ($M^+$+1).

Example 190

Synthesis of tris[4-[N-α-[3-(3-hydroxyphenyl)propanoyl]-D-lysyl]aminophenyl]methane trifluoroacetate Reaction was conducted in the same manner as Example 185, except that 3-(3-hydroxyphenyl)propanoic acid was used instead of 2-hydroxybenzoic acid, to obtain 17.2 mg of the title compound.

The mass spectrometry (MS) data for the obtained compound were as follows.

MS: m/z 1118.6 ($M^+$+1).

Example 191

Synthesis of tris[4-[N-α-[3-(4-hydroxyphenyl)propanoyl]-D-lysyl]aminophenyl]methane trifluoroacetate Reaction was conducted in the same manner as Example 185, except that 3-(4-hydroxyphenyl)propanoic acid was used instead of 2-hydroxybenzoic acid, to obtain 17.7 mg of the title compound.

The mass spectrometry (MS) data for the obtained compound were as follows.

MS: m/z 1118.6 ($M^+$+1).

Example 192

Synthesis of tris[4-[N-α-(6-hydroxynaphthalen-1-yl)carbonyl-D-lysyl]aminophenyl]methane trifluoroacetate Reaction was conducted in the same manner as Example 185, except that 6-hydroxynaphthalene-1-carboxylic acid was used instead of 2-hydroxybenzoic acid, to obtain 11.7 mg of the title compound.

The mass spectrometry (MS) data for the obtained compound were as follows.

MS: m/z 1184.5 ($M^+$+1).

Example 193

Synthesis of tris[4-(N-α-benzoyl-D-lysyl)aminophenyl]methane trifluoroacetate

Reaction was conducted in the same manner as Example 185, except that benzoic acid was used instead of 2-hydroxybenzoic acid, to obtain 2.3 mg of the title compound.

The NMR data and mass spectrometry (MS) data for the obtained compound were as follows.

NMR: (270 MHz, $CD_3OD$) δ: 1.5–1.85 (12H,m), 1.852.15 (6H,m), 2.45–3.05 (6H,m), 4.55–4.80 (3H,m), 5.55 (1H,s), 7.09 (6H,d,J=8.5 Hz), 7.45–7.65 (15H,m), 7.91 (6H,d,J=8.5 Hz).

MS: m/z 986.6 ($M^+$+1).

Example 194

Synthesis of tris[4-[N-α-(1-naphthoyl)-D-lysyl]aminophenyl]methane trifluoroacetate Reaction was conducted in the same manner as Example 185, except that 1-naphthalenecarboxylic acid was used instead of 2-hydroxybenzoic acid, to obtain 3.9 mg of the title compound.

The mass spectrometry (MS) data for the obtained compound were as follows.

MS: m/z 1136.6 (M$^+$+1).

Example 195

Synthesis of tris[4-[N-1-(2-naphthoyl)-D-lysyl]aminophenyl]methane trifluoroacetate Reaction was conducted in the same manner as Example 185, except that 2-naphthalenecarboxylic acid was used instead of 2-hydroxybenzoic acid, to obtain 2.7 mg of the title compound.

The mass spectrometry (MS) data for the obtained compound were as follows.

MS: m/z 1136.6 (M$^+$+1).

Example 196

Synthesis of tris[4-[N-α-[2-(1H-indol-3-yl)acetyl]-D-lysyl]aminophenyl]methane trifluoroacetate Reaction was conducted in the same manner as Example 185, except that 2-(1H-indol-3-yl)acetic acid was used instead of 2-hydroxybenzoic acid, to obtain 2.4 mg of the title compound.

The NMR data and mass spectrometry (MS) data for the obtained compound were as follows.

NMR: (270 MHz, CD$_3$OD) δ: 1.1–2.0 (18H,m), 2.6–2.9 (6H,m), 3.74 (6H,ABq,J=15.4 Hz,1.6 Hz), 4.4–4.7 (3H,m), 5.45 (1H,s), 6.8–7.9 (27H,m).

MS: m/z 1145.6 (M$^+$+1).

Example 197

Synthesis of tris[4-[N-α-(1H-indol-7-yl)carbonyl-D-lysyl]aminophenyl]methane trifluoroacetate Reaction was conducted in the same manner as Example 185, except that indole-7-carboxylic acid was used instead of 2-hydroxybenzoic acid, to obtain 2.5 mg of the title compound.

The mass spectrometry (MS) data for the obtained compound were as follows.

MS: m/z 1103.6 (M$^+$+1).

Example 198

Synthesis of tris[4-(N-α-benzoyl-L-lysyl)aminophenyl]methane trifluoroacetate

The tris[4-(N-ε-t-butoxycarbonyl-L-lysyl)aminophenyl]methane (29 mg) obtained in Reference Example 2, benzoic acid (13 mg) and N-methylmorpholine (30 mg) were dissolved in N,N-dimethylformamide (1 ml), after which an N,N-dimethylformamide solution containing O-(7-azabenzotriazol-1-yl)-1,1,3,3-tetramethyluronium hexafluorophosphate (0.54 M, 0.2 ml) was added while cooling on ice, the temperature was raised to room temperature, and the mixture was stirred for 16 hours. The reaction mixture was poured into water (4 ml) and shaken. This was then centrifuged, and the supernatant was removed. After adding saturated sodium bicarbonate water (4 ml) to the residue and stirring, the mixture was centrifuged and the supernatant was removed. The procedure of centrifugation and removal of the supernatant was then carried out once with saturated sodium bicarbonate water (4 ml) and twice with water (4 ml). The residue was dried under reduced pressure to obtain tris[4-(N-α-benzoyl-N-ε-t-butoxycarbonyl-L-lysyl)aminophenyl]methane.

The tris[4-(N-α-benzoyl-N-ε-t-butoxycarbonyl-L-lysyl)aminophenyl]methane (the total amount obtained in the previous reaction) was dissolved in methanol (1.5 ml), a 4 N hydrochloric acid/dioxane solution (1.5 ml) was added dropwise while cooling on ice, the temperature was raised to room temperature, and the mixture was shaken for 1 hour. The reaction mixture was concentrated under reduced pressure, and a portion of the residue was purified by preparative high performance liquid chromatography using methanol/trifluoroacetic acid (100/0.1) and water/trifluoroacetic acid (100/0.1) as a mixed eluent, to obtain 10.4 mg of the title compound.

The NMR data and mass spectrometry (MS) data for the obtained compound were as follows.

NMR: (270 MHz, CD$_3$OD) δ: 1.5–1.85 (12H,m), 1.852.15 (6H,m), 2.45–3.05 (6H,m), 4.55–4.80 (3H,m), 5.55 (1H,s), 7.09 (6H,d,J=8.5 Hz), 7.45–7.65 (15H,m), 7.91 (6H,d,J=8.5 Hz).

MS: m/z 986.6 (M$^+$+1).

Example 199

Synthesis of tris[4-[N-α-(2-phenylacetyl)-L-lysyl]aminophenyl]methane trifluoroacetate Reaction was conducted in the same manner as Example 198, except that phenylacetic acid was used instead of benzoic acid, to obtain 6.0 mg of the title compound.

The NMR data and mass spectrometry (MS) data for the obtained compound were as follows.

NMR: (270 MHz, CD$_3$OD) δ: 1.40–1.60 (6H,m), 1.60–2.00 (12H,m), 2.80–2.95 (6H,m), 3.63 (6H,s), 4.45–4.55 (3H,m), 5.53 (1H,s), 7.06 (6H,d,J=8.4 Hz), 7.20–7.35 (15H,m), 7.47 (6H,d,J=8.4 Hz).

MS: m/z 1028.7 (M$^+$+1).

Example 200

Synthesis of tris[4-[N-α-(6-hydroxynaphthalen-1-yl)carbonyl-L-lysyl]aminophenyl]methane trifluoroacetate Reaction was conducted in the same manner as Example 198, except that 6-hydroxynaphthalene-1-carboxylic acid was used instead of benzoic acid, to obtain 4.4 mg of the title compound.

The NMR data and mass spectrometry (MS) data for the obtained compound were as follows.

NMR: (270 MHz, CD$_3$OD) δ: 1.55–1.85 (12H,m), 1.852.15 (6H,m), 2.90–3.05 (6H,m), 4.70–4.85 (3H,m), 5.60 (1H,s), 7.05–7.20 (12H,m), 7.40–7.55 (6H,m), 7.59 (6H,d, J=8.6 Hz), 7.80 (3H,d,J=7.7 Hz), 8.14 (3H,d,J=9.1 Hz).

MS: m/z 1184.6 (M$^+$+1).

Example 201

Synthesis of tris[4-[N-α-[2-(1H-indol-3-yl)acetyl]-D-lysyl]aminophenyl]amine trifluoroacetate The tris(4-aminophenyl)amine (8.7 mg) obtained in Reference Example 97, the N-α-[2-(1H-indol-3-yl)acetyl]-N-ε-t-butoxycarbonyl-D-lysine (48 mg) obtained in Reference Example 96 and N-methylmorpholine (33 μl) were dissolved in N,N-dimethylformamide (1 ml), after which O-(7-azabenzotriazol-1-yl)-1,1,3,3-tetramethyluronium hexafluorophosphate (46 mg) was added while cooling on ice, the temperature was raised to room temperature, and the mixture was stirred for 16 hours. The reaction mixture was poured into saturated sodium bicarbonate water (10 ml) and the product was extracted twice with ethyl acetate (10 ml). After combining the organic layer and washing with saturated saline (10 ml), drying was performed over magnesium sulfate. The organic layer was filtered and the filtrate was concentrated under reduced pressure to obtain tris[4-[N-ε-t-butoxycarbonyl-N-α-[2-(1H-indol-3-yl)acetyl]-D-lysyl]aminophenyl]amine as a powder.

The mass spectrometry (MS) data for the obtained compound were as follows.

MS: m/z 1469.6 (M$^+$+23).

The tris[4-[N-ε-t-butoxycarbonyl-N-α-[2-(1H-indol-3-yl)acetyl]-D-lysyl]aminophenyl]amine (the total amount obtained in the previous reaction) was dissolved in methanol (1 ml), a 4 N hydrochloric acid/dioxane solution (1 ml) was added dropwise while cooling on ice, the temperature was raised to room temperature, and the mixture was shaken for 1 hour. The reaction mixture was concentrated under reduced pressure, and a portion of the residue was purified by preparative high performance liquid chromatography using methanol/trifluoroacetic acid (100/0.1) and water/trifluoroacetic acid (100/0.1) as a mixed eluent, to obtain 5.8 mg of the title compound.

The NMR data and mass spectrometry (MS) data for the obtained compound were as follows.

NMR: (270 MHz, CD$_3$OD) δ: 1.22–1.43 (6H,m), 1.431.78 (9H,m), 1.78–1.98 (3H,m), 2.7–2.9 (6H,m), 3.75 (3H,d,J=15.4 Hz), 3.82 (3H,d,J=15.4 Hz), 4.45–4.60 (3H, m), 6.95 (6H,d,J=8.6 Hz), 7.0–7.17 (6H,m), 7.26 (3H,s), 7.36 (6H,d,J=8.6 Hz), 7.39 (3H,d,J=7.9 Hz), 7.61 (3H,d,J=7.9 Hz).

MS: m/z 1146.5 (M$^+$+1).

Experiment Example

The TPO activities of the compounds of the invention obtained in the aforementioned examples were measured by the procedure described below, for evaluation of their thrombopoietic effects.

Establishment of Mpl-expressing Ba/F3 Cell Line

The human mpl gene was cloned from cDNAs of the human erythroleukemia cell line HEL by PCR, and was incorporated into pCOS1 to construct an expression vector. The expression vector was transfected into Ba/F3 cells by electroporation method, and an Mpl-expressing Ba/F3 clone was established.

Measurement of Thrombopoietin (TPO) Activity

The cytokine-eliminated Mpl-expressing Ba/F3 line was plated in a 96-well plate at 25,000 cells/well. DMSO solutions containing the compounds obtained in each of the examples were then prepared to different specified concentration ranges, and each solution was added to the Mpl-expressing Ba/F3 cell line (final DMSO concentration: ≦0.1%), and the cell were cultured at 37° C. for one day. Human TPO (by R&D Systems or Genzyme) was used as a positive control.

Each of the cultured Mpl-expressing Ba/F3 cell lines was subjected to absorbance measurement at a wavelength of 450 nm (reference wavelength: 620 nm), corresponding to the viable cell count, using Cell Count Reagent SF (by Nacalai Tesque Inc.). The TPO activity of each compound for the Mpl-expressing Ba/F3 cell line was determined based on the following formula.

TPO activity (%)=ODt/ODs×100

ODs: Absorbance at maximum reaction of human TPO (wavelength: 450–620 nm).

ODt: Absorbance of test solution (wavelength: 450–620 nm).

Tables 1 and 2 show the maximum TPO activity values and the corresponding concentrations of each compound, as obtained by the test described above.

TABLE 1

| Compound | Concentration (μM) | TPO activity (%) |
|---|---|---|
| Example 1 | 25 | 37.6 |
| Example 6 | 25 | 17.4 |
| Example 7 | 21 | 24.7 |
| Example 10 | 50 | 11.7 |
| Example 13 | 25 | 25.7 |
| Example 15 | 50 | 12.8 |
| Example 17 | 50 | 16.5 |
| Example 18 | 50 | 46.5 |
| Example 19 | 50 | 19.1 |
| Example 21 | 25 | 60.1 |
| Example 23 | 25 | 48.0 |
| Example 29 | 25 | 98.5 |
| Example 30 | 25 | 108 |
| Example 31 | 25 | 96.4 |
| Example 32 | 25 | 87.1 |
| Example 33 | 50 | 17.4 |
| Example 38 | 25 | 124 |
| Example 39 | 12.5 | 80.4 |
| Example 40 | 12.5 | 59.0 |

TABLE 2

| Compound | Concentration (μM) | TPO activity (%) |
|---|---|---|
| Example 131 | 50 | 88.0 |
| Example 132 | 50 | 22.3 |
| Example 133 | 50 | 89.6 |
| Example 134 | 50 | 67.2 |
| Example 135 | 50 | 15.8 |
| Example 146 | 25 | 83.6 |
| Example 148 | 25 | 73.6 |
| Example 151 | 50 | 90.8 |
| Example 152 | 25 | 62.0 |
| Example 155 | 25 | 44.3 |
| Example 157 | 50 | 36.1 |
| Example 159 | 25 | 18.6 |
| Example 160 | 100 | 22.5 |
| Example 161 | 25 | 65.6 |
| Example 164 | 25 | 24.9 |
| Example 172 | 100 | 24.4 |
| Example 173 | 100 | 35.4 |
| Example 186 | 25 | 35.8 |
| Example 187 | 25 | 60.2 |
| Example 188 | 100 | 10.1 |
| Example 192 | 25 | 71.3 |
| Example 193 | 12.5 | 25.4 |
| Example 198 | 12.5 | 87.8 |
| Example 199 | 12.5 | 47.0 |
| Example 200 | 25 | 144 |
| Example 201 | 25 | 110 |

As shown in Tables 1 and 2, the compounds of the invention obtained in the examples described above all exhibited sufficiently high TPO activity, thus confirming their excellent thrombopoietic effects.

Industrial Applicability

As explained above, the triphenylmethane derivatives of the present invention are low molecular compounds which exhibit excellent thrombopoietic effects, have acceptably low antigenicity, and can be obtained by the simple and inexpensive production process of the invention; their use will therefore make it possible to obtain pharmaceutical compositions useful for medical purposes including thrombopoietic agents and thrombocytopenia treatment agents.

What is claimed is:

1. A compound represented by the following general formula (1), or a pharmacologically acceptable salt thereof

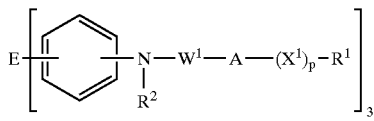

(1)

wherein E represents one selected from the group consisting of a methylidyne group a nitrilo group, $R^1$ represents one selected from the group consisting of a hydrogen atom, a hydroxy group, a carboxy group, optionally substituted amino groups, optionally substituted aryl groups and optionally substituted heterocyclic groups, $R^2$ represents one selected from the group consisting of a hydrogen atom and alkyl groups, $W^1$ represents an amino acid residue, A represents one selected from the group consisting of a carbonyl group and a sulfonyl group, $X^1$ represents one selected from the group consisting of optionally substituted alkylene groups and optionally substituted alkenylene groups, and p represents 0 or 1.

2. A compound according to claim 1 or its pharmacologically acceptable salt, wherein $R_1$ in general formula (1) is one selected from the group consisting of a hydrogen atom, a hydroxy group, a carboxy group, optionally substituted amino groups, optionally substituted aryl groups of 6–14 carbons and optionally substituted 5- to 14-membered heterocyclic groups, $R^2$ is one selected from the group consisting of a hydrogen atom and alkyl groups of 1–6 carbons, $W^1$ is an amino acid residue with a polar side chain, $X^1$ is one selected from the group consisting of optionally substituted alkylene groups of 1–6 carbons and optionally substituted alkenylene groups of 2–6 carbons, and p represents 0 or 1.

3. A compound according to claim 1 or its pharmacologically acceptable salt, wherein $R^1$ in general formula (1) is one selected from the group consisting of a hydrogen atom, optionally substituted monocyclic or fused ring aryl groups of 6–10 carbons and optionally substituted 5- to 9-membered monocyclic or fused ring heterocyclic groups, $R^2$ is one selected from the group consisting of a hydrogen atom and linear or branched alkyl groups of 1–6 carbons, $W^1$ is a basic amino acid residue, and $X^1$ is one selected from the group consisting of alkylene groups of 1–3 carbons and alkenylene groups of 2–4 carbons.

4. A compound according to claim 1 or its pharmacologically acceptable salt, wherein $W^1$ in general formula (1) is an amino acid residue having on the side chain at least one selected from the group consisting of an amino group, a guanidyl group, alkylamino groups of 1–6 carbons and dialkylamino groups of 2–12 carbons.

5. A compound according to claim 1 or its pharmacologically acceptable salt, wherein A in general formula (1) is a carbonyl group, $X^1$ is a methylene group and p is 0 or 1.

6. A compound according to claim 1 or its pharmacologically acceptable salt, wherein said compound is one selected from the group consisting of
tris[4-[N-α[2-(1H-indol-3-yl)acetyl]-L-lysyl]aminophenyl]methane hydrochloride,
tris[4-[N-α-[2-(5-methoxy-2-methyl-1H-indol-3-yl)acetyl]-L-lysyl]aminophenyl]methane hydrochloride,
tris[4-[N-α-[2-(2-methyl-1H-indol-3-yl)acetyl]-L-lysyl]aminophenyl]methane hydrochloride,
tris[4-[N-α-L-tryptophyl-L-lysyl]aminophenyl]methane hydrochloride,
tris[4-[N-α-[2-(thiophen-3-yl)acetyl]-L-lysyl]aminophenyl]methane hydrochloride,
tris[4-(N-α-L-phenylalanyl-L-lysyl)aminophenyl]methane hydrochloride,
tris[4-[N-α-(3-pyridylcarbonyl)-L-lysyl]aminophenyl]methane hydrochloride,
tris[4-[N-α-[2-(5-hydroxy-1H-indol-3-yl)acetyl]-L-lysyl]aminophenyl]methane hydrochloride,
tris[4-[N-α-[2-(4-hydroxyphenyl)acetyl]-L-lysyl]aminophenyl]methane hydrochloride,
tris[4-[N-α-[2-(2-methyl-1H-indol-3-yl)acetyl]-D-lysyl]aminophenyl]methane,
tris[4-[N-α-[2-(thiophen-3-yl)acetyl]-D-lysyl]aminophenyl]methane hydrochloride,
tris[4-[N-α-[2-(1H-indol-3-yl)acetyl]-N-ε-dimethyl-L-lysyl]aminophenyl]methane,
tris[4-[N-α-[2-(2-methyl-1H-indol-3-yl)acetyl]-N-ε-dimethyl-L-lysyl]aminophenyl]methane,
tris[4-[N-α-[2-(5-methoxy-2-methyl-1H-indol-3-yl)acetyl]-N-ε-dimethyl-L-lysyl]aminophenyl]methane,
tris[4-[N-α-[2-(thiophen-3-yl)acetyl]-N-ε-dimethyl-L-lysyl]aminophenyl]methane,
tris[4-[N-α-[2-(1H-indol-3-yl)acetyl]-S-(3-aminopropyl)-L-cystyl]aminophenyl]methane hydorchloride,
tris[4-[N-α-[2-(thiophen-3-yl)acetyl]-L-arginyl]aminophenyl]methane hydrochloride,
tris[4-[N-α-[2-(2-methyl-1H-indol-3-yl)acetyl]-D-arginyl]aminophenyl]methane hydrochloride,
tris[4-[N-α-[2-(thiophen-3-yl)acetyl]-D-arginyl]aminophenyl]methane hydrochloride,
tris[4-[β-aminomethyl-N-[2-(1H-indol-3-yl)acetyl]-L-alanyl]aminophenyl]methane trifluoroacetate,
tris[4-[β-aminomethyl-N-[2-(2-methyl-1H-indol-3-yl)acetyl]-L-alanyl]aminophenyl]methane trifluoroacetate,
tris[4-[N-β-aminomethyl-N-[2-(5-methoxy-2-methyl-1H-indol-3-yl)acetyl]-L-alanyl]aminophenyl]methane trifluoroacetate,
tris[4-[N-α-[2-(1H-indol-3-yl)acetyl]-L-ornithyl]aminophenyl]methane trifluoroacetate,
tris[4-[N-α-[2-(5-methoxy-2-methyl-1H-indol-3-yl)acetyl]-L-omithy]aminophenyl]methane trifluoroacetate,
tris[4-[N-α-[2-(6-methoxy-2-methyl-1H-indol-3-yl)acetyl]-D-lysyl]aminophenyl]methane hydrochloride,
tris[4-[N-α-[2-(2-ethyl-1H-indol-3-yl)acetyl]-D-lysyl]aminophenyl]methane hydrochloride,
tris[4-[N-α-(5-hydroxy-1H-indol-2-yl)carbonyl-D-lysyl]aminophenyl]methane hydrochloride,
tris[4-[N-α-(1H-indol-4-yl)carbonyl-D-lysyl]aminophenyl]methane hydrochloride,
tris[4-[N-α-[2-(7-methyl-1H-indol-3-yl)acetyl]-D-lysyl]aminophenyl]methane hydrochloride,
tris[4-[N-α-(pyrazin-2-yl)carbonyl-D-lysyl]aminophenyl]methane hydrochloride,
tris[4-[N-α-[2-(3-hydroxyphenyl)acetyl]-D-lysyl]aminophenyl]methane hydrochloride,
tris[4-[N-α-(D-tyrosyl)-D-lysyl]aminophenyl]methane hydrochloride,
tris[4-[N-α-(D-tryptophyl)-D-lysyl]aminophenyl]methane hydrochloride,
tris[4-[N-α-[2-(thiophen-2-yl)acetyl]-D-lysyl]aminophenyl]methane hydrochloride,
tris[4-[N-α-[2-pyridin-2-yl)acetyl]-D-lysyl]aminophenyl]methane hydrochloride, tris[4-[N-α-[2-pyridin-4-yl)acetyl]-D-lysyl]aminophenyl]
methane hydrochloride,
tris[4-[N-α-(3-hydroxybenzoyl)-D-lysyl]aminophenyl]
methane trifluoroacetate,
tris[4-[N-α-(2-phenylacetyl)-D-lysyl]aminophenyl]
methane trifluoroacetate,
tris[4-[N-α-[2-(3,4-dihydroxyphenyl)acetyl]-D-lysyl]
aminophenyl]methane trifluoroacetate,
tris[4-[N-α-(6-hydroxynaphthalen-1-yl)carbonyl-D-lysyl]
aminophenyl]methane trifluoroacetate,
tris[4-(N-α-benzoyl-D-lysyl)aminophenyl]methane trifluoroacetate
tris[4-(N-α-benzoyl-L-lysyl)aminophenyl]methane
trifluoroacetate,
tris[4-[N-α-(2-phenylacetyl)-L-lysyl]aminophenyl]methane
trifluoroacetate,
tris[4-[N-α(6-hydroxynaphthalen-1-yl)carbonyl-L-lysyl]
aminophenyl]methane trifluoroacetate, and
tris[4-[N-α-[2-(1H-indol-3-yl)acetyl]-D-lysyl]
aminophenyl]amine trifluoroacetate.

7. A compound production process which comprises a first step of reacting a compound represented by the following general formula (2):

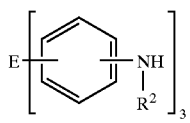 (2)

wherein E represents one selected from the group consisting of a methylidyne group and a nitrilo group and R¹ represents one selected from the group consisting of a hydrogen atom and alky groups, with at least one selected from the group consisting of N^α-9-fluorenylmethoxycarbonylamino acid derivatives represented by the following general formula (3):

Fmoc-W¹ (3)

wherein W¹ represents an amino acid residue and Fmoc represents a 9-fluorenylmethoxycarbonyl group bonded to the α-amino group of said amino acid residue, with the proviso that when said amino acid residue has a side chain functional group, said side chain function group may be protected, and an N^α-t-butoxycarbonylamino acid derivative represented by the following gereral formula (4):

Boc-W^t (4)

wherein W^t represents an amino acid residue and Boc represents a t-butoxycarbonyl group bonded to the α-amino group of said amino acid residue, with the proviso that when said amino acid residue has a side chain functional group, said side chain functional group may be protected, in the presence of a condensation agent;

a second step of deprotecting the Fmoc group or Boc group of the compound obtained in said first step; and a third step of reacting the compound obtained in said second step with a compound represented by the following general formula (5):

R₁—(X¹)_p—A—Z (5)

wherein R¹ represents one selected from the group consisting of a hydrogen atom, a hydroxy group, a carboxy group, optionally substituted amino groups, optionally substituted aryl groups and optionally substituted heterocyclic groups, X¹ represents one selected from the group consisting of optionally substituted alkylene groups and optionally substituted alkenylene groups, p represents 0 or 1, A represents one selected from the group consisting of a carbonyl group and a sulfonyl group, and Z represents one selected from the group consisting of a hydroxy group and halogen groups, in the presence of a condensation agent or a base, to obtain a compound represented by the following formula (1):

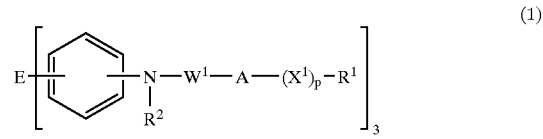 (1)

wherein E represents one selected from the group consisting of a methylidyne group and a nitrilo group, R¹ represents one selected from the group consisting of a hydrogen atom, a hydroxy group, a carboxy group, optionally substituted amino groups, optionally substituted aryl groups and optionally substituted heterocyclic groups, R² represents one selected from the group consisting of a hydrogen atom and alkyl groups, W¹ presents an amino acid residue, A represents one selected from the group consisting of a carbonyl group and a sulfonyl group, X^t represents one selected from the group consisting of optionally substituted alkylene groups and optionally substituted alkenylene groups, and p represents 0 or 1.

8. A compound production process which comprises a fourth step of reacting a amino acid derivative and a silylating agent;

a fifth step of reacting the compound obtained in said fourth step with a compound represented by the following general formula (5)

R¹—(X¹)_p—A—Z (5)

wherein R¹ represents one selected from the group consisting of a hydrogen atom, a hydroxy group, a carboxy group, optionally substituted amino groups, optionally substituted aryl groups and optionally substituted heterocyclic groups, X¹ represents one selected from the group consisting of optionally substituted alkylene groups and optionally substituted alkenylene groups, p represents 0 or 1, A represents one selected from the group consisting of a carbonyl group and a sulfonyl group, and Z represents one selected from the group consisting of a hydroxy group and halogen groups; and a sixth step of reacting the compound obtained in said fifth step with a compound represented by the following general formula (2):

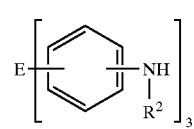 (2)

wherein E represents one selected from the group consisting of a methylidyne group and a nitrilo group and $R^2$ represents one selected from the group consisting of a hydrogen atom and alkyl groups, in the presence of a condensation agent, to obtain a compound represented by the following formula (1):

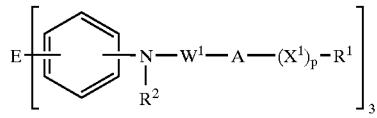

(1)

wherein E represents one selected from the group consisting of a methylidyne group and a nitrilo group, $R^1$ represents one selected from the group consisting of a hydrogen group, a hydroxy group, a carboxy group, optionally substituted amino groups, optionally substituted aryl groups and optionally substituted heterocyclic groups, $R^2$ represents one selected from the group consisting of a hydrogen atom and alkyl groups, $W^1$ represents an amino acid residue, A represents one selected from the group consisting of a carbonyl group and a sulfonyl group, $X^1$ represents one selected from the group consisting of optionally substituted alkylene groups and optionally substituted alkenylene groups, and p represents 0 or 1.

9. A pharmaceutical composition which comprises a compound according to claim 1 or a pharmacologically acceptable salt thereof.

10. A thrombopoietic agent which comprises a compound according to claim 1 or a pharmacologically acceptable salt thereof.

11. A thrombocytopenia treatment agent which comprises a compound according claim 1 or a pharmacologically acceptable salt thereof.

* * * * *